United States Patent
Peabody et al.

(10) Patent No.: US 9,365,831 B2
(45) Date of Patent: *Jun. 14, 2016

(54) PLASMIDS AND METHODS FOR PEPTIDE DISPLAY AND AFFINITY-SELECTION ON VIRUS-LIKE PARTICLES OF RNA BACTERIOPHAGES

(75) Inventors: David S. Peabody, Albuquerque, NM (US); Bryce Chackerian, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 246 days.

This patent is subject to a terminal disclaimer.

(21) Appl. No.: 13/520,057

(22) PCT Filed: Dec. 31, 2010

(86) PCT No.: PCT/US2010/062638
§ 371 (c)(1),
(2), (4) Date: Jul. 20, 2012

(87) PCT Pub. No.: WO2011/082381
PCT Pub. Date: Jul. 7, 2011

(65) Prior Publication Data
US 2012/0295813 A1      Nov. 22, 2012

Related U.S. Application Data

(60) Provisional application No. 61/335,120, filed on Dec. 31, 2009, provisional application No. 61/335,122, filed on Dec. 31, 2009, provisional application No. 61/335,121, filed on Dec. 31, 2009.

(51) Int. Cl.
*C40B 40/08*      (2006.01)
*C12N 7/00*       (2006.01)
(Continued)

(52) U.S. Cl.
CPC . *C12N 7/00* (2013.01); *A61K 39/07* (2013.01); *A61K 39/12* (2013.01);
(Continued)

(58) Field of Classification Search
None
See application file for complete search history.

(56) References Cited

U.S. PATENT DOCUMENTS

2009/0054246 A1      2/2009   Peabody et al.

OTHER PUBLICATIONS

Kunkel TA, Bebenek, McClary J. (1991) Efficient Site-Directed Mutagenesis Using Uracil-Containing DNA. Methods Enzymol. 204:125-139.
(Continued)

*Primary Examiner* — Christian Boesen
(74) *Attorney, Agent, or Firm* — Henry D. Coleman; R. Neil Sudol

(57) ABSTRACT

The present invention relates to a system and method for controlling peptide display valency on virus-like particles (VLPs), especially including MS2 VLPs. In this method, large amounts of wild-type and low quantities of single-chain dimer coat proteins may be produced from a single RNA. Valency is controlled in immunogen (vaccine) production by providing a system that allows the production of large amounts of wild-type and low quantities of single-chain dimer coating proteins from a single RNA, allowing facile adjustment of display valency levels on VLPs, especially MS2 VLPS over a wide range, from few than one—on average—to as many as ninety per particle. This facilitates the production of immunogens and vaccines, including VLPs exhibiting low valency. Nucleic acid constructs useful in the expression of virus-like particles are disclosed, comprised of a coat polypeptide of MS2 modified by insertion of a heterologous peptide, wherein the heterologous peptide is displayed on the virus-like particle and encapsidates MS2 niRNA. Nucleic acid constructs are also disclosed which are useful in the expression of virus-like particles comprised of a coat polypeptide of PP7 modified by insertion of a heterologous peptide, wherein the heterologous peptide is displayed on the virus-like particle and encapsidates PP7 mRNA.

13 Claims, 46 Drawing Sheets

(51) Int. Cl.
  *A61K 39/07* (2006.01)
  *A61K 39/12* (2006.01)
  *C12N 15/10* (2006.01)
  *A61K 39/00* (2006.01)

(52) U.S. Cl.
  CPC .... *C12N 15/1037* (2013.01); *A61K 2039/5258* (2013.01); *C12N 2710/20034* (2013.01); *C12N 2740/16034* (2013.01); *C12N 2740/16134* (2013.01); *C12N 2795/16023* (2013.01); *C12N 2795/18023* (2013.01); *C40B 40/08* (2013.01)

(56) References Cited

OTHER PUBLICATIONS

Sidhu SS, Lowman HB, Cunningham BC, Wells JA. (2000) Phage display for selection of novel binding peptides. Methods Enzymol. 328:333-363.
Kleina LG, Masson J-M, Normanly J, Abelson J, and Miller JH. (1990) Construction of *Escherichia coli* Amber Suppressor tRNA Genes. J. Mol. Biol. 213: 705-717.
Lee SK and Keasling JD. (2005) A propionate-inducible expression system for enteric bacteria. Appl. Env. Microbiol. 71:6856-6862.
Peabody, D. S., and Lim, F. (1996) Complementation of RNA binding site mutations in MS2 coat protein heterodimers. Nucleic Acids Res 24, 2352-2359.
Chang, A. C., and Cohen, S. N. (1978) Construction and Characterization of Amplifiable Multicopy DNA Cloning Vehhicles Derived from the P15A Cryptic Miniplasmid. J Bacteriol 134, 1141-1156.
Caldeira, J. C., and Peabody, D. S. (2007) Stability and assembly in vitro of bacteriophage PP7 virus-like particles. J Nanobiotechnology 5, 10.
Olsthoorn, R. C., Garde, G., Dayhuff, T., Atkins, J. F., and Van Duin, J. (1995) Nucleotide sequence of a single-stranded RNA phage from Pseudomonas aeruginosa: Kinship to coliphages and conservation of regulatory RNA structures. Virology 206, 611-625.
Tars K, F. K., Bundule M, Liljas L. (2000) The three-dimensional structure of bacteriophage PP7 from Pseudomonas aeurginosa at 3.7-A resolution. Virology 272, 331-337.
Lim, F., Downey, T. D., and Peabody, D. S. (2001) Translational repression and specific RNA binding by the coat protein of the Pseudomonas Phage PP7. Journal of Biological Chemistry 276, 22507-22513.
Peabody, D. S. (1990) Translational repression by Bacteriophage MS2 coat protein expressed from a plasmid. J Biol Chem 265, 5684-5689.
Caldeira Jdo C, Medford A, Kines RC, Lino CA, Schiller JT, Chackerian B, Peabody DS: Immunogenic display of diverse peptides, including a broadly cross-type neutralizing human papillomavirus L2 epitope, on virus-like particles of the RNA bacteriophage PP7. Vaccine 2010, 28(27):4384-4393.
Peabody DS, Manifold-Wheeler B, Medford A, Jordan SK, do Carmo Caldeira J, Chackerian B: Immunogenic display of diverse peptides on virus-like particles of RNA phage MS2. J Mol Biol 2008, 380(1):252-263.
Lowman HB, Bass SH, Simpson N, Wells JA: Selecting high-affinity binding proteins by monovalent phage display. Biochemistry 1991, 30(45):10832-10838.
Wells JA: Hormone mimicry. Science 1996, 273(5274):449-450.
Peabody DS: Subunit fusion confers tolerance to peptide insertions in a virus coat protein. Arch Biochem Biophys 1997, 347(1):85-92.
Peabody DS, Chakerian A: Asymmetric contributions to RNA binding by the Thr(45) residues of the MS2 coat protein dimer. J Biol Chem 1999, 274(36):25403-25410.
Lim F, Peabody DS: RNA recognition site of PP7 coat protein. Nucleic Acids Res 2002, 30(19):4138-4144.
Lim F, Downey TP, Peabody DS: Translational repression and specific RNA binding by the coat protein of the Pseudomonas phage PP7. J Biol Chem 2001, 276(25):22507-22513.
Normanly J, Kleina LG, Masson JM, Abelson J, Miller JH: Construction of *Escherichia coli* amber suppressor tRNA genes. III. Determination of tRNA specificity. J Mol Biol 1990, 213(4):719-726.
Kunkel TA: Rapid and efficient site-specific mutagenesis without phenotypic selection. Proc Natl Acad Sci U S A 1985, 82(2):488-492.
Maruyama IN, Maruyama HI, Brenner S: Lambda foo: a lambda phage vector for the expression of foreign proteins. Proc Natl Acad Sci U S A 1994, 91(17):8273-8277.
Mikawa YG, Maruyama IN, Brenner S: Surface display of proteins on bacteriophage lambda heads. J Mol Biol 1996, 262(1):21-30.
Dunn IS: Assembly of functional bacteriophage lambda virions incorporating C-terminal peptide or protein fusions with the major tail protein. J Mol Biol 1995, 248(3):497-506.
Chackerian, Bryce; Caldeira, Jerri Do Carmo; Peabody, Julianne, Peabody, David S. Peptide Epitope Identification by Affinity Selection on Bacteriophage MS2 Virus-Like Particles. J Mole Biol, 2011;409:225-237.
Sakamoto et al.; Site-specific incorporation of an unnatural amino acid into proteins in mammalian cells; Nucleic Acids Research 2002; 30:4692-4699.

Figure 11a

Nucleotide Sequences:

pDSP1 (SEQ ID NO: 1):
TTCTTAGAAAAACTCATCGAGCATCAAATGAAACTGCAATTTATTCATATCAGGA
TTATCAATACCATATTTTTGAAAAAGCCGTTTCTGTAATGAAGGAGAAAACTCAC
CGAGGCAGTTCCATAGGATGGCAAGATCCTGGTATCGGTCTGCGATTCCGACTCG
TCCAACATCAATACAACCTATTAATTTCCCCTCGTCAAAAATAAGGTTATCAAGT
GAGAAATCACCATGAGTGACGACTGAATCCGGTGAGAATGGCAAAAGCTTATGC
ATTTCTTTCCAGACTTGTTCAACAGGCCAGCCATTACGCTCGTCATCAAAATCACT
CGCATCAACCAAACCGTTATTCATTCGTGATTGCGCCTGAGCGAGACGAAATACG
CGATCGCTGTTAAAAGGACAATTACAAACAGGAATCGAATGCAACCGGCGCAGG
AACACTGCCAGCGCATCAACAATATTTTCACCTGAATCAGGATATTCTTCTAATA
CCTGGAATGCTGTTTTCCCGGGGATCGCAGTGGTGAGTAACCATGCATCATCAGG
AGTACGGATAAAATGCTTGATGGTCGGAAGAGGCATAAATTCCGTCAGCCAGTT
TAGTCTGACCATCTCATCTGTAACATCATTGGCAACGCTACCTTTGCCATGTTTCA
GAAACAACTCTGGCGCATCGGGCTTCCCATACAATCGATAGATTGTCGCACCTGA
TTGCCCGACATTATCGCGAGCCCATTTATACCCATATAAATCAGCATCCATGTTG
GAATTTAATCGCGGCCTCGAGCAAGACGTTTCCCGTTGAATATGGCTCATAACAC
CCCTTGTATTACTGTTTATGTAAGCAGACAGTTTTATTGTTCATGACCAAAATCCC
TTAACGTGAGTTTTCGTTCCACTGAGCGTCAGACCCCGTAGAAAAGATCAAGGA
TCTTCTTGAGATCCTTTTTTTCTGCGCGTAATCTGCTGCTTGCAAACAAAAAAACC
ACCGCTACCAGCGGTGGTTTGTTTGCCGGATCAAGAGCTACCAACTCTTTTTCCG
AAGGTAACTGGCTTCAGCAGAGCGCAGATACCAAATACTGTCCTTCTAGTGTAGC
CGTAGTTAGGCCACCACTTCAAGAACTCTGTAGCACCGCCTACATACCTCGCTCT
GCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATAC
CTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTT
GAGCGTCGATTTTTGTGATGCTCGTCAGGGGGCGGAGCCTATGGAAAAACGCC
AGCAACGCGGCCTTTTTACGGTTCCTGGCCTTTTGCTGGCCTTTTGCTCACATGTT
CTTTCCTGCGTTATCCCCTGATTCTGTGGATAACCGTATTACCGCCTTTGAGTGAG
CTGATACCGCTCGCCGCAGCCGAACGACCGAGCGCAGCGAGTCAGTGAGCGAGG
AAGCGGAAGAGCGCCTGATGCGGTATTTTCTCCTTACGCATCTGTGCGGTATTTC

Figure 11a (Con't)

```
ACACCGCATATATGGTGCACTCTCAGTACAATCTGCTCTGATGCCGCATAGTTAA
GCCAGTATACACTCCGCTATCGCTACGTGACTGGGTCATGGCTGCGCCCCGACAC
CCGCCAACACCCGCTGACGCGCCCTGACGGGCTTGTCTGCTCCCGGCATCCGCTT
ACAGACAAGCTGTGACCGTCTCCGGGAGCTGCATGTGTCAGAGGTTTTCACCGTC
ATCACCGAAACGCGCGAGGCAGCTGCGGTAAAGCTCATCAGCGTGGTCGTGAAG
CGATTCACAGATGTCTGCCTGTTCATCCGCGTCCAGCTCGTTGAGTTTCTCCAGAA
GCGTTAATGTCTGGCTTCTGATAAAGCGGGCCATGTTAAGGGCGGTTTTTTCCTG
TTTGGTCACTGATGCCTCCGTGTAAGGGGGATTTCTGTTCATGGGGGTAATGATA
CCGATGAAACGAGAGAGGATGCTCACGATACGGGTTACTGATGATGAACATGCC
CGGTTACTGGAACGTTGTGAGGGTAAACAACTGGCGGTATGGATGCGGCGGGAC
CAGAGAAAAATCACTCAGGGTCAATGCCAGCGCTTCGTTAATACAGATGTAGGT
GTTCCACAGGGTAGCCAGCAGCATCCTGCGATGCAGATCCGGAACATAATGGTG
CAGGGCGCTGACTTCCGCGTTTCCAGACTTTACGAAACACGGAAACCGAAGACC
ATTCATGTTGTTGCTCAGGTCGCAGACGTTTTGCAGCAGCAGTCGCTTCACGTTC
GCTCGCGTATCGGTGATTCATTCTGCTAACCAGTAAGGCAACCCCGCCAGCCTAG
CCGGGTCCTCAACGACAGGAGCACGATCATGCGCACCCGTGGCCAGGACCCAAC
GCTGCCCGAGATGCGCCGCGTGCGGCTGCTGGAGATGGCGGACGCGATGGATAT
GTTCTGCCAAGGGTTGGTTTGCGCATTCACAGTTCTCCGCAAGAATTGATTGGCT
CCAATTCTTGGAGTGGTGAATCCGTTAGCGAGGTGCCGCCGGCTTCCATTCAGGT
CGAGGTGGCCCGGCTCCATGCACCGCGACGCAACGCGGGGAGGCAGACAAGGTA
TAGGGCGGCGCCTACAATCCATGCCAACCCGTTCCATGTGCTCGCCGAGGCGGCA
TAAATCGCCGTGACGATCAGCGGTCCAGTGATCGAAGTTAGGCTGGTAAGAGCC
GCGAGCGATCCTTGAAGCTGTCCCTGATGGTCGTCATCTACCTGCCTGGACAGCA
TGGCCTGCAACGCGGGCATCCCGATGCCGCCGGAAGCGAGAAGAATCATAATGG
GGAAGGCCATCCAGCCTCGCGTCGCGAACGCCAGCAAGACGTAGCCCAGCGCGT
CGGCCGCCATGCCGGCGATAATGGCCTGCTTCTCGCCGAAACGTTGGTGGCGGG
ACCAGTGACGAAGGCTTGAGCGAGGGCGTGCAAGATTCCGAATACCGCAAGCGA
CAGGCCGATCATCGTCGCGCTCCAGCGAAAGCGGTCCTCGCCGAAAATGACCCA
GAGCGCTGCCGGCACCTGTCCTACGAGTTGCATGATAAAGAAGACAGTCATAAG
TGCGGCGACGATAGTCATGCCCCGCGCCCACCGGAAGGAGCTGACTGGGTTGAA
GGCTCTCAAGGGCATCGGCTCTCCCTTATGCGACTCCTGCATTAGGAAGCAGCCC
AGTAGTAGGTTGAGGCCGTTGAGCACCGCCGCCGCAAGGAATGGTGCATGCAAG
GAGATGGCGCCCAACAGTCCCCGGCCACGGGGCCTGCCACCATACCCACGCCG
AAACAAGCGCTCATGAGCCCGAAGTGGCGAGCCCGATCTTCCCCATCGGTGATG
TCGGCGATATAGGCGCCAGCAACCGCACCTGTGGCGCCGGTGATGCCGGCCACG
ATGCGTCCGGCGTAGAGGATCGAGATCTCGATCCCGCGAAATTAATACGACTCA
CTATAGGGAGACCACAACGGTTTCCCTCTAGAAATAATTTTGTTTAACTTTAAGA
AGGAGATATACCATGGCTTCTAACTTTACTCAGTTCGTTCTCGTTGACAATGGCG
GAACTGGCGACGTGACTGTCGCCCCAAGCAACTTCGCTAACGGGGTCGCTGAAT
```

Figure 11a (Con't)

```
GGATCAGCTCTAACTCGCGTTCACAGGCTTACAAAGTAACCTGTAGCGTTCGTCA
GAGCTCTGCGCAGAATCGCAAATACACCATCAAAGTCGAGGTGCCTAAAGTGGC
AACCCAGACTGTTGGTGGTGTAGAGCTTCCTGTAGCCGCATGGCGTTCGTACTTA
AATATGGAACTAACCATTCCAATTTTCGCTACGAATTCCGACTGCGAGCTTATTG
TTAAGGCAATGCAAGGTCTCCTAAAAGATGGAAACCCGATTCCCTCAGCAATCG
CAGCAAACTCCGGCCTCTACGGCAACTTTACTCAGTTCGTTCTCGTCGACAATGG
CGGTACCGGCGACGTGACTGTCGCCCCAAGCAACTTCGCTAACGGGTCGCTGA
ATGGATCAGCTCTAACTCGCGTTCACAGGCTTACAAAGTAACCTGTAGCGTTCGT
CAGAGCTCTGCGCAGAATCGCAAATACACCATCAAAGTCGAGGTGCCTAAAGTG
GCAACCCAGACTGTTGGTGGTGTAGAGCTTCCTGTAGCCGCATGGCGTTCGTACT
TAAATATGGAACTAACCATTCCAATTTTCGCTACGAATTCCGACTGCGAGCTTAT
TGTTAAGGCAATGCAAGGTCTCCTAAAAGATGGAAACCCGATTCCCTCAGCAATC
GCAGCAAACTCCGGCATCTACTAATAGACGCCGGGTTAATTAATTAAGGATCCG
GCTGCTAACAAAGCCCGAAAGGAAGCTGAGTTGGCTGCTGCCACCGCTGAGCAA
TAACTAGCATAACCCCTTGGGGCCTCTAAACGGGTCTTGAGGGGTTTTTTGCTGA
AAGGAGGAACTATATCCGGATATCCACAGGACGGGTGTGGTCGCCATGATCGCG
TAGTCGATAGTGGCTCCAAGTAGCGAAGCGAGCAGGACTGGGCGGCGGCCAAAG
CGGTCGGACAGTGCTCCGAGAACGGGTGCGCATAGAAATTGCATCAACGCATAT
AGCGCTAGCAGCACGCCATAGTGACTGGCGATGCTGTCGGAATGGACGATATCC
CGCAAGAGGCCCGGCAGTACCGGCATAACCAAGCCTATGCCTACAGCATCCAGG
GTGACGGTGCCGAGGATGACGATGAGCGCATTGTTAGATTTCATACACGGTGCCT
GACTGCGTTAGCAATTTAACTGTGATAAACTACCGCATTAAAGCTTATCGATGAT
AAGCTGTCAAACATGAA
```

Figure 11b pDSP1(am) (SEQ ID: 2)

TTCTTAGAAAAACTCATCGAGCATCAAATGAAACTGCAATTTATTCATATCAGGA
TTATCAATACCATATTTTTGAAAAAGCCGTTTCTGTAATGAAGGAGAAAACTCAC
CGAGGCAGTTCCATAGGATGGCAAGATCCTGGTATCGGTCTGCGATTCCGACTCG
TCCAACATCAATACAACCTATTAATTTCCCCTCGTCAAAAATAAGGTTATCAAGT
GAGAAATCACCATGAGTGACGACTGAATCCGGTGAGAATGGCAAAAGCTTATGC
ATTTCTTTCCAGACTTGTTCAACAGGCCAGCCATTACGCTCGTCATCAAAATCACT
CGCATCAACCAAACCGTTATTCATTCGTGATTGCGCCTGAGCGAGACGAAATACG
CGATCGCTGTTAAAAGGACAATTACAAACAGGAATCGAATGCAACCGGCGCAGG
AACACTGCCAGCGCATCAACAATATTTTCACCTGAATCAGGATATTCTTCTAATA
CCTGGAATGCTGTTTTCCCGGGGATCGCAGTGGTGAGTAACCATGCATCATCAGG
AGTACGGATAAAATGCTTGATGGTCGGAAGAGGCATAAATTCCGTCAGCCAGTT
TAGTCTGACCATCTCATCTGTAACATCATTGGCAACGCTACCTTTGCCATGTTTCA
GAAACAACTCTGGCGCATCGGGCTTCCCATACAATCGATAGATTGTCGCACCTGA
TTGCCCGACATTATCGCGAGCCCATTTATACCCATATAAATCAGCATCCATGTTG
GAATTTAATCGCGGCCTCGAGCAAGACGTTTCCCGTTGAATATGGCTCATAACAC
CCCTTGTATTACTGTTTATGTAAGCAGACAGTTTTATTGTTCATGACCAAAATCCC
TTAACGTGAGTTTTCGTTCCACTGAGCGTCAGACCCCGTAGAAAAGATCAAGGA
TCTTCTTGAGATCCTTTTTTTCTGCGCGTAATCTGCTGCTTGCAAACAAAAAAACC
ACCGCTACCAGCGGTGGTTTGTTTGCCGGATCAAGAGCTACCAACTCTTTTTCCG
AAGGTAACTGGCTTCAGCAGAGCGCAGATACCAAATACTGTCCTTCTAGTGTAGC
CGTAGTTAGGCCACCACTTCAAGAACTCTGTAGCACCGCCTACATACCTCGCTCT
GCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATAC
CTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTT
GAGCGTCGATTTTTGTGATGCTCGTCAGGGGGCGGAGCCTATGGAAAAACGCC
AGCAACGCGGCCTTTTTACGGTTCCTGGCCTTTTGCTGGCCTTTTGCTCACATGTT
CTTTCCTGCGTTATCCCCTGATTCTGTGGATAACCGTATTACCGCCTTTGAGTGAG
CTGATACCGCTCGCCGCAGCCGAACGACCGAGCGCAGCGAGTCAGTGAGCGAGG
AAGCGGAAGAGCGCCTGATGCGGTATTTTCTCCTTACGCATCTGTGCGGTATTTC
ACACCGCATATATGGTGCACTCTCAGTACAATCTGCTCTGATGCCGCATAGTTAA
GCCAGTATACACTCCGCTATCGCTACGTGACTGGGTCATGGCTGCGCCCCGACAC
CCGCCAACACCCGCTGACGCGCCCTGACGGGCTTGTCTGCTCCCGGCATCCGCTT
ACAGACAAGCTGTGACCGTCTCCGGGAGCTGCATGTGTCAGAGGTTTTCACCGTC
ATCACCGAAACGCGCGAGGCAGCTGCGGTAAAGCTCATCAGCGTGGTCGTGAAG
CGATTCACAGATGTCTGCCTGTTCATCCGCGTCCAGCTCGTTGAGTTTCTCCAGAA
GCGTTAATGTCTGGCTTCTGATAAAGCGGGCCATGTTAAGGGCGGTTTTTTCCTG
TTTGGTCACTGATGCCTCCGTGTAAGGGGGATTTCTGTTCATGGGGGTAATGATA
CCGATGAAACGAGAGAGGATGCTCACGATACGGGTTACTGATGATGAACATGCC
CGGTTACTGGAACGTTGTGAGGGTAAACAACTGGCGGTATGGATGCGGCGGGAC
CAGAGAAAAATCACTCAGGGTCAATGCCAGCGCTTCGTTAATACAGATGTAGGT
GTTCCACAGGGTAGCCAGCAGCATCCTGCGATGCAGATCCGGAACATAATGGTG
CAGGGCGCTGACTTCCGCGTTTCCAGACTTTACGAAACACGGAAACCGAAGACC
ATTCATGTTGTTGCTCAGGTCGCAGACGTTTTGCAGCAGCAGTCGCTTCACGTTC
GCTCGCGTATCGGTGATTCATTCTGCTAACCAGTAAGGCAACCCCGCCAGCCTAG

Figure 11b (Con't)

CCGGGTCCTCAACGACAGGAGCACGATCATGCGCACCCGTGGCCAGGACCCAAC
GCTGCCCGAGATGCGCCGCGTGCGGCTGCTGGAGATGGCGGACGCGATGGATAT
GTTCTGCCAAGGGTTGGTTTGCGCATTCACAGTTCTCCGCAAGAATTGATTGGCT
CCAATTCTTGGAGTGGTGAATCCGTTAGCGAGGTGCCGCCGGCTTCCATTCAGGT
CGAGGTGGCCCGGCTCCATGCACCGCGACGCAACGCGGGGAGGCAGACAAGGTA
TAGGGCGGCGCCTACAATCCATGCCAACCCGTTCCATGTGCTCGCCGAGGCGGCA
TAAATCGCCGTGACGATCAGCGGTCCAGTGATCGAAGTTAGGCTGGTAAGAGCC
GCGAGCGATCCTTGAAGCTGTCCCTGATGGTCGTCATCTACCTGCCTGGACAGCA
TGGCCTGCAACGCGGGCATCCCGATGCCGCCGGAAGCGAGAAGAATCATAATGG
GGAAGGCCATCCAGCCTCGCGTCGCGAACGCCAGCAAGACGTAGCCCAGCGCGT
CGGCCGCCATGCCGGCGATAATGGCCTGCTTCTCGCCGAAACGTTTGGTGGCGGG
ACCAGTGACGAAGGCTTGAGCGAGGGCGTGCAAGATTCCGAATACCGCAAGCGA
CAGGCCGATCATCGTCGCGCTCCAGCGAAAGCGGTCCTCGCCGAAAATGACCCA
GAGCGCTGCCGGCACCTGTCCTACGAGTTGCATGATAAAGAAGACAGTCATAAG
TGCGGCGACGATAGTCATGCCCCGCGCCCACCGGAAGGAGCTGACTGGGTTGAA
GGCTCTCAAGGGCATCGGCTCTCCCTTATGCGACTCCTGCATTAGGAAGCAGCCC
AGTAGTAGGTTGAGGCCGTTGAGCACCGCCGCCGCAAGGAATGGTGCATGCAAG
GAGATGGCGCCCAACAGTCCCCGGCCACGGGGCCTGCCACCATACCCACGCCG
AAACAAGCGCTCATGAGCCCGAAGTGGCGAGCCCGATCTTCCCCATCGGTGATG
TCGGCGATATAGGCGCCAGCAACCGCACCTGTGGCGCCGGTGATGCCGGCCACG
ATGCGTCCGGCGTAGAGGATCGAGATCTCGATCCCGCGAAATTAATACGACTCA
CTATAGGGAGACCACAACGGTTTCCCTCTAGAAATAATTTTGTTTAACTTTAAGA
AGGAGATATACAATGGCTTCTAACTTTACTCAGTTCGTTCTCGTTGACAATGGCG
GAACTGGCGACGTGACTGTCGCCCCAAGCAACTTCGCTAACGGGGTCGCTGAAT
GGATCAGCTCTAACTCGCGTTCACAGGCTTACAAAGTAACCTGTAGCGTTCGTCA
GAGCTCTGCGCAGAATCGCAAATACACCATCAAAGTCGAGGTGCCTAAAGTGGC
AACCCAGACTGTTGGTGGTGTAGAGCTTCCTGTAGCCGCATGGCGTTCGTACTTA
AATATGGAACTAACCATTCCAATTTTCGCTACGAATTCCGACTGCGAGCTTATTG
TTAAGGCAATGCAAGGTCTCCTAAAAGATGGAAACCCGATTCCCTCAGCAATCG
CAGCAAACTCCGGCATCTACTAGAACTTTACTCAGTTCGTTCTCGTCGACAATGG
CGGTACCGGCGACGTGACTGTCGCCCCAAGCAACTTCGCTAACGGGGTCGCTGA
ATGGATCAGCTCTAACTCGCGTTCACAGGCTTACAAAGTAACCTGTAGCGTTCGT
CAGAGCTCTGCGCAGAATCGCAAATACACCATCAAAGTCGAGGTGCCTAAAGTG
GCAACCCAGACTGTTGGTGGTGTAGAGCTTCCTGTAGCCGCATGGCGTTCGTACT
TAAATATGGAACTAACCATTCCAATTTTCGCTACGAATTCCGACTGCGAGCTTAT
TGTTAAGGCAATGCAAGGTCTCCTAAAAGATGGAAACCCGATTCCCTCAGCAATC
GCAGCAAACTCCGGCATCTACTAATAGACGCCGGGTTAATTAATTAAGGATCCG
GCTGCTAACAAAGCCCGAAAGGAAGCTGAGTTGGCTGCTGCCACCGCTGAGCAA
TAACTAGCATAACCCCTTGGGGCCTCTAAACGGGTCTTGAGGGGTTTTTTGCTGA
AAGGAGGAACTATATCCGGATATCCACAGGACGGGTGTGGTCGCCATGATCGCG
TAGTCGATAGTGGCTCCAAGTAGCGAAGCGAGCAGGACTGGGCGGCGGCCAAAG
CGGTCGGACAGTGCTCCGAGAACGGGTGCGCATAGAAATTGCATCAACGCATAT
AGCGCTAGCAGCACGCCATAGTGACTGGCGATGCTGTCGGAATGGACGATATCC
CGCAAGAGGCCCGGCAGTACCGGCATAACCAAGCCTATGCCTACAGCATCCAGG

Figure 11b (Con't)

GTGACGGTGCCGAGGATGACGATGAGCGCATTGTTAGATTTCATACACGGTGCCT
GACTGCGTTAGCAATTTAACTGTGATAAACTACCGCATTAAAGCTTATCGATGAT
AAGCTGTCAAACATGAA

Figure 11c pDSP62 (SEQ ID NO: 3):
TTCTTAGAAAAACTCATCGAGCATCAAATGAAACTGCAATTTATTCATATCAGGA
TTATCAATACCATATTTTTGAAAAAGCCGTTTCTGTAATGAAGGAGAAAACTCAC
CGAGGCAGTTCCATAGGATGGCAAGATCCTGGTATCGGTCTGCGATTCCGACTCG
TCCAACATCAATACAACCTATTAATTTCCCCTCGTCAAAAATAAGGTTATCAAGT
GAGAAATCACCATGAGTGACGACTGAATCCGGTGAGAATGGCAAAAGCTTATGC
ATTTCTTTCCAGACTTGTTCAACAGGCCAGCCATTACGCTCGTCATCAAAATCACT
CGCATCAACCAAACCGTTATTCATTCGTGATTGCGCCTGAGCGAGACGAAATACG
CGATCGCTGTTAAAAGGACAATTACAAACAGGAATCGAATGCAACCGGCGCAGG
AACACTGCCAGCGCATCAACAATATTTTCACCTGAATCAGGATATTCTTCTAATA
CCTGGAATGCTGTTTTCCCGGGGATCGCAGTGGTGAGTAACCATGCATCATCAGG
AGTACGGATAAAATGCTTGATGGTCGGAAGAGGCATAAATTCCGTCAGCCAGTT
TAGTCTGACCATCTCATCTGTAACATCATTGGCAACGCTACCTTTGCCATGTTTCA
GAAACAACTCTGGCGCATCGGGCTTCCCATACAATCGATAGATTGTCGCACCTGA
TTGCCCGACATTATCGCGAGCCCATTTATACCCATATAAATCAGCATCCATGTTG
GAATTTAATCGCGGCCTCGAGCAAGACGTTTCCCGTTGAATATGGCTCATAACAC
CCCTTGTATTACTGTTTATGTAAGCAGACAGTTTTATTGTTCATGACCAAAATCCC
TTAACGTGAGTTTTCGTTCCACTGAGCGTCAGACCCCGTAGAAAAGATCAAAGGA
TCTTCTTGAGATCCTTTTTTTCTGCGCGTAATCTGCTGCTTGCAAACAAAAAAACC
ACCGCTACCAGCGGTGGTTTGTTTGCCGGATCAAGAGCTACCAACTCTTTTTCCG
AAGGTAACTGGCTTCAGCAGAGCGCAGATACCAAATACTGTCCTTCTAGTGTAGC
CGTAGTTAGGCCACCACTTCAAGAACTCTGTAGCACCGCCTACATACCTCGCTCT
GCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATAC
CTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTT
GAGCGTCGATTTTTGTGATGCTCGTCAGGGGGCGGAGCCTATGGAAAAACGCC
AGCAACGCGGCCTTTTTACGGTTCCTGGCCTTTTGCTGGCCTTTTGCTCACATGTT
CTTTCCTGCGTTATCCCCTGATTCTGTGGATAACCGTATTACCGCCTTTGAGTGAG
CTGATACCGCTCGCCGCAGCCGAACGACCGAGCGCAGCGAGTCAGTGAGCGAGG
AAGCGGAAGAGCGCCTGATGCGGTATTTTCTCCTTACGCATCTGTGCGGTATTTC
ACACCGCATATATGGTGCACTCTCAGTACAATCTGCTCTGATGCCGCATAGTTAA
GCCAGTATACACTCCGCTATCGCTACGTGACTGGGTCATGGCTGCGCCCCGACAC
CCGCCAACACCCGCTGACGCGCCCTGACGGGCTTGTCTGCTCCCGGCATCCGCTT
ACAGACAAGCTGTGACCGTCTCCGGGAGCTGCATGTGTCAGAGGTTTTCACCGTC
ATCACCGAAACGCGCGAGGCAGCTGCGGTAAAGCTCATCAGCGTGGTCGTGAAG
CTTTTCAAAATTGTAAACGTTAATATTTTGTTAAAATTCGCGTTAAATTTTTGTTA
AATCAGCTCATTTTTTAACCAATAGGCCGAAATCGGCAAAATCCCTTATAAATCA
AAAGAATAGCCCGAGATAGGGTTGAGTGTTGTTCCAGTTTGGAACAAGAGTCCA

Figure 11c (Con't)

CTATTAAAGAACGTGGACTCCAACGTCAAAGGGCGAAAAACCGTCTATCAGGGC
GATGGCCCACTACGTGAACCATCACCCAAATCAAGTTTTTGGGGTCGAGGTGCCG
TAAAGCACTAAATCGGAACCCTAAAGGGAGCCCCGATTTAGAGCTTGACGGGG
AAAGCCGGCGAACGTGGCGAGAAAGGAAGGGAAGAAAGCGAAAGGAGCGGGC
GCTAGGGCGCTGGCAAGTGTAGCGGTCACGCTGCGCGTAACCACCACACCCGCC
GCGCTTAATGCGCCGCTACAGGGCGCGTACTATGGTTGCTTTGACGTCGGCCGCC
ATGCCGGCGATAATGGCCTGCTTCTCGCCGAAACGTTTGGTGGCGGGACCAGTGA
CGAAGGCTTGAGCGAGGGCGTGCAAGATTCCGAATACCGCAAGCGACAGGCCGA
TCATCGTCGCGCTCCAGCGAAAGCGGTCCTCGCCGAAAATGACCCAGAGCGCTG
CCGGCACCTGTCCTACGAGTTGCATGATAAAGAAGACAGTCATAAGTGCGGCGA
CGATAGTCATGCCCCGCGCCCACCGGAAGGAGCTGACTGGGTTGAAGGCTCTCA
AGGGCATCGGCTCTCCCTTATGCGACTCCTGCATTAGGAAGCAGCCCAGTAGTAG
GTTGAGGCCGTTGAGCACCGCCGCCGCAAGGAATGGTGCATGCAAGGAGATGGC
GCCCAACAGTCCCCCGGCCACGGGGCCTGCCACCATACCCACGCCGAAACAAGC
GCTCATGAGCCCGAAGTGGCGAGCCCGATCTTCCCCATCGGTGATGTCGGCGATA
TAGGCGCCAGCAACCGCACCTGTGGCGCCGGTGATGCCGGCCACGATGCGTCCG
GCGTAGAGGATCGAGATCTCGATCCCGCGAAATTAATACGACTCACTATAGGGA
GACCACAACGGTTTCCCTCTAGAAATAATTTTGTTTAACTTTAAGAAGGAGATAT
ACCATGGCAAGCAATTTCACGCAATTTGTATTGGTAGATAACGGGGGTACGGGG
GATGTTACGGTAGCACCTTCAAATTTTGCAAATGGTGTAGCAGAGTGGATATCAA
GCAATAGCAGAAGCCAAGCATATAAGGTTACGTGCTCAGTAAGACAATCAAGCG
CTCAAAACAGAAAGTATACGATAAAGGTAGAAGTTCCGAAGGTTGCTACGCAAA
CGGTAGGTGGTGTTGAATTGCCGGTTGCAGCTTGGAGAAGCTATCTCAACATGGA
GTTGACGATACCTATATTTGCAACCAACAGTGATTGTGAATTGATAGTAAAAGCT
ATGCAGGGGTTGTTGAAGGACGGTAATCCTATACCGAGCGCTATAGCTGCTAATA
GTGGCCTCTACGGCAACTTTACTCAGTTCGTTCTCGTCGACAATGGCGGAACTGG
CGACGTGACTGTCGCCCCAAGCAACTTCGCTAACGGGGTCGCTGAATGGATCAG
CTCTAACTCGCGTTCACAGGCTTACAAAGTAACCTGTAGCGTTCGTCAGAGCTCT
GCGCAGAATCGCAAATACACCATCAAAGTCGAGGTGCCTAAAGTGGCAACCCAG
ACTGTTGGTGGTGTAGAGCTTCCTGTAGCCGCATGGCGTTCGTACTTAAATATGG
AACTAACCATTCCAATTTTCGCTACGAATTCCGACTGCGAGCTTATTGTTAAGGC
AATGCAAGGTCTCCTAAAAGATGGAAACCCGATTCCCTCAGCAATCGCAGCAAA
CTCCGGCATCTACTAATAGACGCCGGGTTAATTAATTAGGATCCGGCTGCTAACA
AAGCCCGAAAGGAAGCTGAGTTGGCTGCTGCCACCGCTGAGCAATAACTAGCAT
AACCCCTTGGGGCCTCTAAACGGGTCTTGAGGGGTTTTTTGCTGAAAGGAGGAAC
TATATCCGGATATCCACAGGACGGGTGTGGTCGCCATGATCGCGTAGTCGATAGT
GGCTCCAAGTAGCGAAGCGAGCAGGACTGGGCGGCGGCCAAAGCGGTCGGACA
GTGCTCCGAGAACGGGTGCGCATAGAAATTGCATCAACGCATATAGCGCTAGCA

Figure 11c (Con't)

```
GCACGCCATAGTGACTGGCGATGCTGTCGGAATGGACGATATCCCGCAAGAGGC
CCGGCAGTACCGGCATAACCAAGCCTATGCCTACAGCATCCAGGGTGACGGTGC
CGAGGATGACGATGAGCGCATTGTTAGATTTCATACACGGTGCCTGACTGCGTTA
GCAATTTAACTGTGATAAACTACCGCATTAAAGCTTATCGATGATAAGCTGTCAA
ACATGAA
```

Figure 11d pDSP62(am) (SEQ ID:4)
TTCTTAGAAAAACTCATCGAGCATCAAATGAAACTGCAATTTATTCATATCAGGA
TTATCAATACCATATTTTTGAAAAAGCCGTTTCTGTAATGAAGGAGAAAACTCAC
CGAGGCAGTTCCATAGGATGGCAAGATCCTGGTATCGGTCTGCGATTCCGACTCG
TCCAACATCAATACAACCTATTAATTTCCCCTCGTCAAAAATAAGGTTATCAAGT
GAGAAATCACCATGAGTGACGACTGAATCCGGTGAGAATGGCAAAAGCTTATGC
ATTTCTTTCCAGACTTGTTCAACAGGCCAGCCATTACGCTCGTCATCAAAATCACT
CGCATCAACCAAACCGTTATTCATTCGTGATTGCGCCTGAGCGAGACGAAATACG
CGATCGCTGTTAAAGGACAATTACAAACAGGAATCGAATGCAACCGGCGCAGG
AACACTGCCAGCGCATCAACAATATTTTCACCTGAATCAGGATATTCTTCTAATA
CCTGGAATGCTGTTTTCCCGGGGATCGCAGTGGTGAGTAACCATGCATCATCAGG
AGTACGGATAAAATGCTTGATGGTCGGAAGAGGCATAAATTCCGTCAGCCAGTT
TAGTCTGACCATCTCATCTGTAACATCATTGGCAACGCTACCTTTGCCATGTTTCA
GAAACAACTCTGGCGCATCGGGCTTCCCATACAATCGATAGATTGTCGCACCTGA
TTGCCCGACATTATCGCGAGCCCATTTATACCCATATAAATCAGCATCCATGTTG
GAATTTAATCGCGGCCTCGAGCAAGACGTTTCCCGTTGAATATGGCTCATAACAC
CCCTTGTATTACTGTTTATGTAAGCAGACAGTTTTATTGTTCATGACCAAAATCCC
TTAACGTGAGTTTTCGTTCCACTGAGCGTCAGACCCCGTAGAAAAGATCAAAGGA
TCTTCTTGAGATCCTTTTTTTCTGCGCGTAATCTGCTGCTTGCAAACAAAAAAACC
ACCGCTACCAGCGGTGGTTTGTTTGCCGGATCAAGAGCTACCAACTCTTTTTCCG
AAGGTAACTGGCTTCAGCAGAGCGCAGATACCAAATACTGTCCTTCTAGTGTAGC
CGTAGTTAGGCCACCACTTCAAGAACTCTGTAGCACCGCCTACATACCTCGCTCT
GCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATAC
CTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTT
GAGCGTCGATTTTTGTGATGCTCGTCAGGGGGGCGGAGCCTATGGAAAAACGCC
AGCAACGCGGCCTTTTTACGGTTCCTGGCCTTTTGCTGGCCTTTTGCTCACATGTT
CTTTCCTGCGTTATCCCCTGATTCTGTGGATAACCGTATTACCGCCTTTGAGTGAG
CTGATACCGCTCGCCGCAGCCGAACGACCGAGCGCAGCGAGTCAGTGAGCGAGG
AAGCGGAAGAGCGCCTGATGCGGTATTTTCTCCTTACGCATCTGTGCGGTATTTC
ACACCGCATATATGGTGCACTCTCAGTACAATCTGCTCTGATGCCGCATAGTTAA
GCCAGTATACACTCCGCTATCGCTACGTGACTGGGTCATGGCTGCGCCCCGACAC
CCGCCAACACCCGCTGACGCGCCCTGACGGGCTTGTCTGCTCCCGGCATCCGCTT
ACAGACAAGCTGTGACCGTCTCCGGGAGCTGCATGTGTCAGAGGTTTTCACCGTC
ATCACCGAAACGCGCGAGGCAGCTGCGGTAAAGCTCATCAGCGTGGTCGTGAAG
CTTTTCAAAATTGTAAACGTTAATATTTTGTTAAAATTCGCGTTAAATTTTTGTTA
AATCAGCTCATTTTTTAACCAATAGGCCGAAATCGGCAAAATCCCTTATAAATCA
AAAGAATAGCCCGAGATAGGGTTGAGTGTTGTTCCAGTTTGGAACAAGAGTCCA
CTATTAAAGAACGTGGACTCCAACGTCAAAGGGCGAAAAACCGTCTATCAGGGC
GATGGCCCACTACGTGAACCATCACCCAAATCAAGTTTTTGGGGTCGAGGTGCCG
TAAAGCACTAAATCGGAACCCTAAAGGGAGCCCCCGATTTAGAGCTTGACGGGG
AAAGCCGGCGAACGTGGCGAGAAAGGAAGGGAAGAAAGCGAAAGGAGCGGGC
GCTAGGGCGCTGGCAAGTGTAGCGGTCACGCTGCGCGTAACCACCACACCCGCC
GCGCTTAATGCGCCGCTACAGGGCGCGTACTATGGTTGCTTTGACGTCGGCCGCC
ATGCCGGCGATAATGGCCTGCTTCTCGCCGAAACGTTTGGTGGCGGGACCAGTGA

Figure 11d (Con't)

```
CGAAGGCTTGAGCGAGGGCGTGCAAGATTCCGAATACCGCAAGCGACAGGCCGA
TCATCGTCGCGCTCCAGCGAAAGCGGTCCTCGCCGAAAATGACCCAGAGCGCTG
CCGGCACCTGTCCTACGAGTTGCATGATAAAGAAGACAGTCATAAGTGCGGCGA
CGATAGTCATGCCCCGCGCCCACCGGAAGGAGCTGACTGGGTTGAAGGCTCTCA
AGGGCATCGGCTCTCCCTTATGCGACTCCTGCATTAGGAAGCAGCCCAGTAGTAG
GTTGAGGCCGTTGAGCACCGCCGCCGCAAGGAATGGTGCATGCAAGGAGATGGC
GCCCAACAGTCCCCGGCCACGGGGCCTGCCACCATACCCACGCCGAAACAAGC
GCTCATGAGCCCGAAGTGGCGAGCCCGATCTTCCCCATCGGTGATGTCGGCGATA
TAGGCGCCAGCAACCGCACCTGTGGCGCCGGTGATGCCGGCCACGATGCGTCCG
GCGTAGAGGATCGAGATCTCGATCCCGCGAAATTAATACGACTCACTATAGGGA
GACCACAACGGTTTCCCTCTAGAAATAATTTTGTTTAACTTTAAGAAGGAGATAT
ACCATGGCAAGCAATTTCACGCAATTTGTATTGGTAGATAACGGGGTACGGGG
GATGTTACGGTAGCACCTTCAAATTTTGCAAATGGTGTAGCAGAGTGGATATCAA
GCAATAGCAGAAGCCAAGCATATAAGGTTACGTGCTCAGTAAGACAATCAAGCG
CTCAAAACAGAAAGTATACGATAAAGGTAGAAGTTCCGAAGGTTGCTACGCAAA
CGGTAGGTGGTGTTGAATTGCCGGTTGCAGCTTGGAGAAGCTATCTCAACATGGA
GTTGACGATACCTATATTTGCAACCAACAGTGATTGTGAATTGATAGTAAAAGCT
ATGCAGGGGTTGTTGAAGGACGGTAATCCTATACCGAGCGCTATAGCTGCTAATA
GTGGCCTCTACTAGAACTTTACTCAGTTCGTTCTCGTCGACAATGGCGGAACTGG
CGACGTGACTGTCGCCCCAAGCAACTTCGCTAACGGGGTCGCTGAATGGATCAG
CTCTAACTCGCGTTCACAGGCTTACAAAGTAACCTGTAGCGTTCGTCAGAGCTCT
GCGCAGAATCGCAAATACACCATCAAAGTCGAGGTGCCTAAAGTGGCAACCCAG
ACTGTTGGTGGTGTAGAGCTTCCTGTAGCCGCATGGCGTTCGTACTTAAATATGG
AACTAACCATTCCAATTTTCGCTACGAATTCCGACTGCGAGCTTATTGTTAAGGC
AATGCAAGGTCTCCTAAAAGATGGAAACCCGATTCCCTCAGCAATCGCAGCAAA
CTCCGGCATCTACTAATAGACGCCGGGTTAATTAATTAGGATCCGGCTGCTAACA
AAGCCCGAAAGGAAGCTGAGTTGGCTGCTGCCACCGCTGAGCAATAACTAGCAT
AACCCCTTGGGGCCTCTAAACGGGTCTTGAGGGGTTTTTTGCTGAAAGGAGGAAC
TATATCCGGATATCCACAGGACGGGTGTGGTCGCCATGATCGCGTAGTCGATAGT
GGCTCCAAGTAGCGAAGCGAGCAGGACTGGGCGGCGGCCAAAGCGGTCGGACA
GTGCTCCGAGAACGGGTGCGCATAGAAATTGCATCAACGCATATAGCGCTAGCA
GCACGCCATAGTGACTGGCGATGCTGTCGGAATGGACGATATCCCGCAAGAGGC
CCGGCAGTACCGGCATAACCAAGCCTATGCCTACAGCATCCAGGGTGACGGTGC
CGAGGATGACGATGAGCGCATTGTTAGATTTCATACACGGTGCCTGACTGCGTTA
GCAATTTAACTGTGATAAACTACCGCATTAAAGCTTATCGATGATAAGCTGTCAA
ACATGAA
```

Figure 11e

M13CM1 (SEQ ID NO. 5):
AACATCCAATAAATCATACAGGCAAGGCAAAGAATTAGCAAAATTAAGCAATAA
AGCCTCAGAGCATAAAGCTAAATCGGTTGTACCAAAAACATTATGACCCTGTAAT
ACTTTTGCGGGAGAAGCCTTTATTTCAACGCAAGGATAAAAATTTTTAGAACCCT
CATATATTTTAAATGCAATGCCTGAGTAATGTGTAGGTAAAGATTCAAAAGGGTG
AGAAAGGCCGGAGACAGTCAAATCACCATCAATATGATATTCAACCGTTCTAGC
TGATAAATTCATGCCGGAGAGGGTAGCTATTTTTGAGAGGTCTACAAAGGCTATC
AGGTCATTGCCTGAGAGTCTGGAGCAAACAAGAGAATCGATGAACGGTAATCGT
AAAACTAGCATGTCAATCATATGTACCCCGGTTGATAATCAGAAAAGCCCCAAA
AACAGGAAGATTGTATAAGCAAATATTTAAATTGTAAACGTTAATATTTTGTTAA
AATTCGCGTTAAATTTTGTTAAATCAGCTCATTTTTTAACCAATAGGCCGAAATC
GGCAAAATCCCTTATAAATCAAAAGAATAGCCCGAGACCTGCAGGGGGGGGGGG
GGAAAGCCACGTTGTGTCTCAAAATCTCTGATGTTACATTGCACAAGATAAAAAT
ATATCATCATGAACAATAAAACTGTCTGCTTACATAAACAGTAATACAAGGGGT
GTTATGAGCCATATTCAACGGGAAACGTCTTGCTCGAGTGTTGATACCGGGAAGC
CCTGGGCCAACTTTTGGCGAAAATGAGACGTTGATCGGCACGTAAGAGGTTCCA
ACTTTCACCATAATGAAATAAGATCACTACCGGGCGTATTTTTGAGTTATCGAG
ATTTTCAGGAGCTAAGGAAGCTAAAATGGAGAAAAAATCACTGGATATACCAC
CGTTGATATATCCCAATGGCATCGTAAAGAACATTTTGAGGCATTTCAGTCAGTT
GCTCAATGTACCTATAACCAGACCGTTCAGCTGGATATTACGGCCTTTTTAAAGA
CCGTAAAGAAAAATAAGCACAAGTTTTATCCGGCCTTTATTCACATTCTTGCCCG
CCTGATGAATGCTCATCCGGAATTCCGTATGGCAATGAAAGACGGTGAGCTGGT
GATATGGGATAGTGTTCACCCTTGTTACACCGTTTTCCATGAGCAAACTGAAACG
TTTTCATCGCTCTGGAGTGAATACCACGACGATTTCCGGCAGTTTCTACACATAT
ATTCGCAAGATGTGGCGTGTTACGGTGAAAACCTGGCCTATTTCCCTAAAGGGTT
TATTGAGAATATGTTTTTCGTCTCAGCCAATCCCTGGGTGAGTTTCACCAGTTTTG
ATTTAAACGTGGCCAATATGGACAACTTCTTCGCCCCCGTTTTCACCATGGGCAA
ATATTATACGCAAGGCGACAAGGTGCTGATGCCGCTGGCGATTCAGGTTCATCAT
GCCGTCTGTGATGGCTTCCATGTCGGCAGAATGCTTAATGAATTACAACAGTACT
GCGATGAGTGGCAGGGCGGGGCGTAATTTTTTAAGGCAGTTATTGGTGCCCTTA
AACGCCTGGTGCTACGCCTGAATAAGTGATAATAAGCGGATGAATGGCAGAAAT
TGAGCTCGAATCGGCTGGCTGGTTTATTGCTGATAAATCTGGAGCCGGTGAGCGT
GGGTCTCGCGGTATCATTGCAGCACTGGGGCCAGATGGTAAGCCCTCCCGTATCG
TAGTTATCTACACGACGGGGAGTCAGGCAACTATGGATGAACGAAATAGACAGA
TCGCTGAGATAGGTGCCTCACTGATTAAGCATTGGTAACTGTCAGACCAAGTTTA
CTCATATATACTTTAGATTGATTTAAAACTTCATTTTTAATTTAAAAGGATCTAGG
TGAAGATCCTTTTTGATAATCTCATGACCAAAATCCCTTAACGTGAGTTTTCGTTC
CACTGAGCGTCAGACCCCTTAATAAGATGATCTTCTTGAGATCGTTTTGGTCTGC
GCGTAATCTCTTGCTCTGAAAACGAAAAAACCGCCTTGCAGGGCGGTTTTTCGAA
GGTTCTCTGAGCTACCAACTCTTTGAACCGAGGTAACTGGCTTGGAGGAGCGCAG

Figure 11e (Con't)

```
TCACCAAAACTTGTCCTTTCAGTTTAGCCTTAACCGGCGCATGACTTCAAGACTA
ACTCCTCTAAATCAATTACCAGTGGCTGCTGCCAGTGGTGCTTTTGCATGTCTTTC
CGGGTTGGACTCAAGACGATAGTTACCGGATAAGGCGCAGCGGTCGGACTGAAC
GGGGGGTTCGTGCATACAGTCCAGCTTGGAGCGAACTGCCTACCCGGAACTGAG
TGTCAGGCGTGGAATGAGACAAACGCGGCCATAACAGCGGAATGACACCGGTAA
ACCGAAAGGCAGGAACAGGAGAGCGCACGAGGGAGCCGCCAGGGGGAAACGCC
TGGTATCTTTATAGTCCTGTCGGGTTTCGCCACCACTGATTTGAGCGTCAGATTTC
GTGATGCTTGTCAGGGGGGCGGAGCCTATGGAAAAACGGCTTTGCCGCGGCCCT
CTCACTTCCCTGTTAAGTATCTTCCTGGCATCTTCCAGGAAATCTCCGCCCCGTTC
GTAAGCCATTTCCGCTCGCCGCAGTCGAACGACCGAGCGTAGCGAGTCAGTGAG
CGAGGAAGCGGAATATATCCTGTATCACATATTCTGCTGACGCACCGGTGCAGCC
TTTTTTCTCCTGCCACATGAAGCGATCCGTCCCGAGATAGGGTTGAGTGTTGTTCC
AGTTTGGAACAAGAGTCCACTATTAAAGAACGTGGACTCCAACGTCAAAGGGCG
AAAAACCGTCTATCAGGGCGATGGCCCACTACGTGAACCATCACCCAAATCAAG
TTTTTTGGGGTCGAGGTGCCGTAAAGCACTAAATCGGAACCCTAAAGGGAGCCC
CCGATTTAGAGCTTGACGGGGAAAGCCGGCGAACGTGGCGAGAAAGGAAGGGA
AGAAAGCGAAAGGAGCGGGCGCTAGGGCGCTGGCAAGTGTAGCGGTCACGCTG
CGCGTAACCACCACACCCGCCGCGCTTAATGCGCCGCTACAGGGCGCGTACTATG
GTTGCTTTGACGAGCACGTATAACGTGCTTTCCTCGTTGGAATCAGAGCGGGAGC
TAAACAGGAGGCCGATTAAAGGGATTTTAGACAGGAACGGTACGCCAGAATCTT
GAGAAGTGTTTTTATAATCAGTGAGGCCACCGAGTAAAAGAGTCTGTCCATCACG
CAAATTAACCGTTGTAGCAATACTTCTTTGATTAGTAATAACATCACTTGCCTGA
GTAGAAGAACTCAAACTATCGGCCTTGCTGGTAATATCCAGAACAATATTACCGC
CAGCCATTGCAACAGGAAAAACGCTCATGGAAATACCTACATTTTGACGCTCAAT
CGTCTGAAATGGATTATTTACATTGGCAGATTCACCAGTCACACGACCAGTAATA
AAAGGGACATTCTGGCCAACAGAGATAGAACCCTTCTGACCTGAAAGCGTAAGA
ATACGTGGCACAGACAATATTTTTGAATGGCTATTAGTCTTTAATGCGCGAACTG
ATAGCCCTAAAACATCGCCATTAAAAATACCGAACGAACCACCAGCAGAAGATA
AAACAGAGGTGAGGCGGTCAGTATTAACACCGCCTGCAACAGTGCCACGCTGAG
AGCCAGCAGCAAATGAAAAATCTAAAGCATCACCTTGCTGAACCTCAAATATCA
AACCCTCAATCAATATCTGGTCAGTTGGCAAATCAACAGTAGAAAGGAATTGAG
GAAGGTTATCTAAAATATCTTTAGGTGCACTAACAACTAATAGATTAGAGCCGTC
AATAGATAATACATTTGAGGATTTAGAAGTATTAGACTTTACAAACAATTCGACA
ACTCGTATTAAATCCTTTGCCCGAACGTTATTAATTTTAAAAGTTTGAGTAACATT
ATCATTTTGCGGAACAAAGAAACCACCAGAAGGAGCGGAATTATCATCATATTC
CTGATTATCAGATGATGGCAATTCATCAATATAATCCTGATTGTTTGGATTATACT
TCTGAATTATGGAAGGAATTGAACCAACCATATCAAAATTATTAGCACGTAAAA
```

Figure 11e (Con't)

CAGAAATAAAGAAATTGCGTAGATTTTCAGGTTTAACGTCAGATGAATATACAGT
AACAGTACCTTTTACATCGGGAGAAACAATAACGGATTCGCCTGATTGCTTTGAA
TACCAAGTTACAAAATCGCGCAGAGGCGAATTATTCATTTCAATTACCTGAGCAA
AAGAAGATGATGAAACAAACATCAAGAAAACAAAATTAATTACATTTAACAATT
TCATTTGAATTACCTTTTTTAATGGAAACAGTACATAAATCAATATATGTGAGTG
AATAACCTTGCTTCTGTAAATCGTCGCTATTAATTAATTTTCCCTTAGAATCCTTG
AAAACATAGCGATAGCTTAGATTAAGACGCTGAGAAGAGTCAATAGTGAATTTA
TCAAAATCATAGGTCTGAGAGACTACCTTTTTAACCTCCGGCTTAGGTTGGGTTA
TATAACTATATGTAAATGCTGATGCAAATCCAATCGCAAGACAAAGAACGCGAG
AAAACTTTTTCAAATATATTTTAGTTAATTTCATCTTCTGACCTAAATTTAATGGT
TTGAAATACCGACCGTGTGATAAATAAGGCGTTAAATAAGAATAAACACCGGAA
TCATAATTACTAGAAAAGCCTGTTTAGTATCATATGCGTTATACAAATTCTTAC
CAGTATAAAGCCAACGCTCAACAGTAGGGCTTAATTGAGAATCGCCATATTTAAC
AACGCCAACATGTAATTTAGGCAGAGGCATTTTCGAGCCAGTAATAAGAGAATA
TAAAGTACCGACAAAAGGTAAAGTAATTCTGTCCAGACGACGACAATAAACAAC
ATGTTCAGCTAATGCAGAACGCGCCTGTTTATCAACAATAGATAAGTCCTGAACA
AGAAAAATAATATCCCATCCTAATTTACGAGCATGTAGAAACCAATCAATAATC
GGCTGTCTTTCCTTATCATTCCAAGAACGGGTATTAAACCAAGTACCGCACTCAT
CGAGAACAAGCAAGCCGTTTTTATTTTCATCGTAGGAATCATTACCGCGCCCAAT
AGCAAGCAAATCAGATATAGAAGGCTTATCCGGTATTCTAAGAACGCGAGGCGT
TTTAGCGAACCTCCCGACTTGCGGGAGGTTTTGAAGCCTTAAATCAAGATTAGTT
GCTATTTTGCACCCAGCTACAATTTTATCCTGAATCTTACCAACGCTAACGAGCG
TCTTTCCAGAGCCTAATTTGCCAGTTACAAAATAAACAGCCATATTATTTATCCC
AATCCAAATAAGAAACGATTTTTTGTTTAACGTCAAAAATGAAAATAGCAGCCTT
TACAGAGAGAATAACATAAAAACAGGGAAGCGCATTAGACGGGAGAATTAACT
GAACACCCTGAACAAAGTCAGAGGGTAATTGAGCGCTAATATCAGAGAGATAAC
CCACAAGAATTGAGTTAAGCCCAATAATAAGAGCAAGAAACAATGAAATAGCAA
TAGCTATCTTACCGAAGCCCTTTTTAAGAAAAGTAAGCAGATAGCCGAACAAAG
TTACCAGAAGGAAACCGAGGAAACGCAATAATAACGGAATACCCAAAAGAACT
GGCATGATTAAGACTCCTTATTACGCAGTATGTTAGCAAACGTAGAAAATACATA
CATAAAGGTGGCAACATATAAAAGAAACGCAAAGACACCACGGAATAAGTTTAT
TTTGTCACAATCAATAGAAAATTCATATGGTTTACCAGCGCTAAAGACAAAAGG
GCGACATTCAACCGATTGAGGGAGGGAAGGTAAATATTGACGGAAATTATTCAT
TAAAGGTGAATTATCACCGTCACCGACTTGAGCCATTTGGGAATTAGAGCCAGCA
AAATCACCAGTAGCACCATTACCATTAGCAAGGCCGGAAACGTCACCAATGAAA
CCATCGATAGCAGCACCGTAATCAGTAGCGACAGAATCAAGTTTGCCTTTAGCGT
CAGACTGTAGCGCGTTTTCATCGGCATTTTCGGTCATAGCCCCCTTATTAGCGTTT
GCCATCTTTTCATAATCAAAATCACCGGAACCAGAGCCACCACCGGAACCGCCTC
CCTCAGAGCCGCCACCCTCAGAACCGCCACCCTCAGAGCCACCACCCTCAGAGC
CGCCACCAGAACCACCACCAGAGCCGCCGCCAGCATTGACAGGAGGTTGAGGCA

Figure 11e (Con't)

```
GGTCAGACGATTGGCCTTGATATTCACAAACGAATGGATCCTCATTAAAGCCAGA
ATGGAAAGCGCAGTCTCTGAATTTACCGTTCCAGTAAGCGTCATACATGGCTTTT
GATGATACAGGAGTGTACTGGTAATAAGTTTTAACGGGGTCAGTGCCTTGAGTAA
CAGTGCCCGTATAAACAGTTAATGCCCCCTGCCTATTTCGGAACCTATTATTCTG
AAACATGAAAGTATTAAGAGGCTGAGACTCCTCAAGAGAAGGATTAGGATTAGC
GGGGTTTTGCTCAGTACCAGGCGGATAAGTGCCGTCGAGAGGGTTGATATAAGT
ATAGCCCGGAATAGGTGTATCACCGTACTCAGGAGGTTTAGTACCGCCACCCTCA
GAACCGCCACCCTCAGAACCGCCACCCTCAGAGCCACCACCCTCATTTTCAGGGA
TAGCAAGCCCAATAGGAACCCATGTACCGTAACACTGAGTTTCGTCACCAGTACA
AACTACAACGCCTGTAGCATTCCACAGACAACCCTCATAGTTAGCGTAACGATCT
AAAGTTTTGTCGTCTTTCCAGACGTTAGTAAATGAATTTTCTGTATGGGGTTTTGC
TAAACAACTTTCAACAGTTTCAGCGGAGTGAGAATAGAAAGGAACAACTAAAGG
AATTGCGAATAATAATTTTTTCACGTTGAAAATCTCCAAAAAAAAAGGCTCCAAA
AGGAGCCTTTAATTGTATCGGTTTATCAGCTTGCTTTCGAGGTGAATTTCTTAAAC
AGCTTGATACCGATAGTTGCGCCGACAATGACAACAACCATCGCCCACGCATAA
CCGATATATTCGGTCGCTGAGGCTTGCAGGGAGTTAAAGGCCGCTTTTGCGGGAT
CGTCACCCTCAGCAGCGAAAGACAGCATCGGAACGAGGGTAGCAACGGCTACAG
AGGCTTTGAGGACTAAAGACTTTTTCATGAGGAAGTTTCCATTAAACGGGTAAAA
TACGTAATGCCACTACGAAGGCACCAACCTAAAACGAAAGAGGCGAAAGAATAC
ACTAAAACACTCATCTTTGACCCCAGCGATTATACCAAGCGCGAAACAAAGTA
CAACGGAGATTTGTATCATCGCCTGATAAATTGTGTCGAAATCCGCGACCTGCTC
CATGTTACTTAGCCGGAACGAGGCGCAGACGGTCAATCATAAGGGAACCGAACT
GACCAACTTTGAAAGAGGACAGATGAACGGTGTACAGACCAGGCGCATAGGCTG
GCTGACCTTCATCAAGAGTAATCTTGACAAGAACCGGATATTCATTACCCAAATC
AACGTAACAAAGCTGCTCATTCAGTGAATAAGGCTTGCCCTGACGAGAAACACC
AGAACGAGTAGTAAATTGGGCTTGAGATGGTTTAATTTCAACTTTAATCATTGTG
AATTACCTTATGCGATTTTAAGAACTGGCTCATTATACCAGTCAGGACGTTGGGA
AGAAAAATCTACGTTAATAAAACGAACTAACGGAACAACATTATTACAGGTAGA
AAGATTCATCAGTTGAGATTTAGGAATACCACATTCAACTAATGCAGATACATAA
CGCCAAAAGGAATTACGAGGCATAGTAAGAGCAACACTATCATAACCCTCGTTT
ACCAGACGACGATAAAAACCAAATAGCGAGAGGCTTTTGCAAAAGAAGTTTTG
CCAGAGGGGGTAATAGTAAAATGTTTAGACTGGATAGCGTCCAATACTGCGGAA
TCGTCATAAATATTCATTGAATCCCCTCAAATGCTTTAAACAGTTCAGAAACG
AGAATGACCATAAATCAAAAATCAGGTCTTTACCCTGACTATTATAGTCAGAAGC
AAAGCGGATTGCATCAAAAGATTAAGAGGAAGCCCGAAAGACTTCAAATATCG
CGTTTTAATTCGAGCTTCAAAGCGAACCAGACCGGAAGCAAACTCCAACAGGTC
AGGATTAGAGAGTACCTTTAATTGCTCCTTTTGATAAGAGGTCATTTTTGCGGAT
GGCTTAGAGCTTAATTGCTGAATCTGGTGCTGTAGCTCAACATGTTTTAAATATG
CAACTAAAGTACGGTGTCTGGAAGTTTCATTCCATGTAACAGTTGATTCCCAATT
CTGCGAACGAGTAGATTTAGTTTGACCATTAGATACATTTCGCAAATGGTCAATA
ACCTGTTTAGCTATATTTTCATTTGGGGCGCGAGCTGAAAAGGTGGCATCAATTC
TACTAATAGTAGTAGCGTT
```

Figure 14

Wild-type PP7 coat protein N-terminal sequence: SEQ ID NO: 20

```
 1    2    3    4    5    6    7    8    9   10   11   12   13   14   15   16   17   18
ATG, GCC, AAA, ACC, ATC, GTT, CTT, TCG, GTC, GGC, GAG, GCT, ACT, CGC, ACT, CTG, ACT, GAG
Met, ala, lys, thr, ile, val, leu, ser, val, gly, glu, ala, thr, arg, thr, leu, thr, gl
``` pP7K mutant coat protein sequence (KpnI site in bold): SEQ ID NO 21

```
 1    2    3    4    5    6    7    8    9   10   11   12   13   14   15   16   17   18
ATG, GCC, AAA, ACC, ATC, GTT, CTT, TCG, GTC, GGT, ACC, GCT, ACT, CGC, ACT, CTG, ACT, GAG
Met, ala, lys, thr, ile, val, leu, ser, val, gly, thr, ala, thr, arg, thr, leu, thr, glu
```

Primers for insertion of random peptide sequences: SEQ ID NO 22
GCG GGTACC(NNY)6,GCT,ACT,CGC,ACT,CTG,ACT,GAG    1112-(NNY)$_6$
This yields exact insertions between residues thr11 and ala12.

GCG GGTACC(NNY)6,GAG,GCT,ACT,CGC,ACT,CTG,ACT,GAG    1111-(NNY)$_6$ SEQ ID NO 23
GCG GGTACC(NNY)8,GAG,GCT,ACT,CGC,ACT,CTG,ACT,GAG    1111-(NNY)$_8$ SEQ ID NO 24
GCG GGTACC(NNY)10,GAG,GCT,ACT,CGC,ACT,CTG,ACT,GAG    1111-(NNY)$_{10}$ SEQ ID NO 25

These last three primers yield insertions between thr11 and glu11, i.e.
residue 11 is repeated at the insertion boundaries, but it's thr on the N-
terminal side, and glu (the wild-type position 11 amino acid) on the C-
terminal side.

Specific peptide insertions were constructed using the following primers:

Fp7 (Flag peptide) SEQ ID NO 26
GCC,GGT,ACC,GAT,TAT,AAA,GAT,GAT,GAT,GAT,AAA,GAG,GCT,ACT,CGC,ACT,CTG,ACT,GA
G atxp7 (anthrax F20 epitope) SEQ ID NO 27
GCC,GGT,ACC,GTG,CAT,GCG,AGC,TTT,TTT,GAT,ATC,GGC,GGC,GAG,GCT,ACT,CGC,ACT,CT
G,ACT,GAG atxp7r (anthrax protective antigen F20 epitope with randomized flanking
amino acids) SEQ ID NO 28
GCC,GGT,ACC,NNS,NNS,GCG,AGC,TTT,TTT,GAT,NNS,NNS,GAG,GCT,ACT,CGC,ACT,CTG,AC
T,GAG v3p7 (HIV V3 loop) SEQ ID NO 29
GCC,GGT,ACC,ATC,CAG,CGC,GGC,CCG,GGC,CGC,GCG,TTT,GTG,GAG,GCT,ACT,CGC,ACT,CT
G,ACT,GAG L2p7 (HPV L2 peptide) SEQ ID NO 30
GCC,GGT,ACC,CAG,CTG,TAT,AAA,ACC,TGC,AAA,CAG,GCG,GGC,ACC,TGC,CCG,CCG,GAT,GA
G,GCT,ACT,CGC,ACT,CTG,ACT,GAG L2.5p7 (HPV L@ half-peptide) SEQ ID NO 31
GCC,GGT,ACC,CAG,CTG,TAT,AAA,ACC,TGC,AAA,CAG,GAG,GCT,ACT,CGC,ACT,CTG,ACT,GA
G SEQ ID NO 32 Flag epitope          DYKDDDDK
SEQ ID NO 33 HIV V3 peptide        IQRGPGRAPV
SEQ ID NO 34 HPV16 L2 peptide      QLYKTCKQAGTCPPD
SEQ ID NO 35 Anthrax Protective Antigen    VHASFFDIGG

Figure 19

Rounds 1 and 2:

| | | | | | | | | | | | | |
|---|---|---|---|---|---|---|---|---|---|---|---|---|
| SEQ ID NO: 36 | | | | K | Y | E | Y | K | E | S | V | K | P | (1/6) |
| SEQ ID NO: 37 | | T | D | S | T | R | Y | K | D | W | T | | | (1/6) |
| SEQ ID NO: 38 | | | | | | G | Y | K | E | H | T | S | Y | L | S | (1/6) |
| SEQ ID NO: 39 | | | | Y | S | G | Y | K | Y | P | E | N | Q | (1/6) |
| SEQ ID NO: 40 | | | | | A | D | Y | K | T | F | E | V | P | A | (1/6) |
| SEQ ID NO: 41 | | | | P | H | L | Y | K | E | S | W | P | | (1/6) |

Round 3:

| | | | | | | | | | | | |
|---|---|---|---|---|---|---|---|---|---|---|---|
| SEQ ID NO: 42 | | | G | D | Y | T | D | Y | K | S | D | D | (1/5) |
| SEQ ID NO: 43 | | | D | T | F | M | D | Y | K | S | R | D | (1/5) |
| SEQ ID NO: 44 | H | L | L | S | E | G | D | Y | K | S | G | D | (1/5) |
| SEQ ID NO: 45 | | | D | T | R | | D | Y | K | L | A | D | P | (1/5) |
| SEQ ID NO: 46 | | | L | D | Y | N | D | Y | K | S | R | D | (1/5) |

Round 4:

| | | | | | | | | | | | |
|---|---|---|---|---|---|---|---|---|---|---|---|
| SEQ ID NO: 47 | | G | D | Y | T | D | Y | K | S | D | D | (7/7) |

SEQ ID NO: 48  wild-type                D  Y  K   D  D  D   D  K  L

Figure 22

Figure 23a pET2P7K32 (SEQ ID:6)
TTCTTAGAAAAACTCATCGAGCATCAAATGAAACTGCAATTTATTCATATCAGGA
TTATCAATACCATATTTTTGAAAAGCCGTTTCTGTAATGAAGGAGAAAACTCAC
CGAGGCAGTTCCATAGGATGGCAAGATCCTGGTATCGGTCTGCGATTCCGACTCG
TCCAACATCAATACAACCTATTAATTTCCCCTCGTCAAAAATAAGGTTATCAAGT
GAGAAATCACCATGAGTGACGACTGAATCCGGTGAGAATGGCAAAAGCTTATGC
ATTTCTTTCCAGACTTGTTCAACAGGCCAGCCATTACGCTCGTCATCAAAATCACT
CGCATCAACCAAACCGTTATTCATTCGTGATTGCGCCTGAGCGAGACGAAATACG
CGATCGCTGTTAAAAGGACAATTACAAACAGGAATCGAATGCAACCGGCGCAGG
AACACTGCCAGCGCATCAACAATATTTTCACCTGAATCAGGATATTCTTCTAATA
CCTGGAATGCTGTTTTCCCGGGGATCGCAGTGGTGAGTAACCATGCATCATCAGG
AGTACGGATAAAATGCTTGATGGTCGGAAGAGGCATAAATTCCGTCAGCCAGTT
TAGTCTGACCATCTCATCTGTAACATCATTGGCAACGCTACCTTTGCCATGTTTCA
GAAACAACTCTGGCGCATCGGGCTTCCCATACAATCGATAGATTGTCGCACCTGA
TTGCCCGACATTATCGCGAGCCCATTTATACCCATATAAATCAGCATCCATGTTG
GAATTTAATCGCGGCCTCGAGCAAGACGTTTCCCGTTGAATATGGCTCATAACAC
CCCTTGTATTACTGTTTATGTAAGCAGACAGTTTTATTGTTCATGACCAAAATCCC
TTAACGTGAGTTTTCGTTCCACTGAGCGTCAGACCCCGTAGAAAAGATCAAAGGA
TCTTCTTGAGATCCTTTTTTTCTGCGCGTAATCTGCTGCTTGCAAACAAAAAAACC
ACCGCTACCAGCGGTGGTTTGTTTGCCGGATCAAGAGCTACCAACTCTTTTTCCG
AAGGTAACTGGCTTCAGCAGAGCGCAGATACCAAATACTGTCCTTCTAGTGTAGC
CGTAGTTAGGCCACCACTTCAAGAACTCTGTAGCACCGCCTACATACCTCGCTCT
GCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATAC
CTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTT
GAGCGTCGATTTTTGTGATGCTCGTCAGGGGGGCGGAGCCTATGGAAAAACGCC
AGCAACGCGGCCTTTTTACGGTTCCTGGCCTTTTGCTGGCCTTTTGCTCACATGTT
CTTTCCTGCGTTATCCCCTGATTCTGTGGATAACCGTATTACCGCCTTTGAGTGAG
CTGATACCGCTCGCCGCAGCCGAACGACCGAGCGCAGCGAGTCAGTGAGCGAGG
AAGCGGAAGAGCGCCTGATGCGGTATTTTCTCCTTACGCATCTGTGCGGTATTTC
ACACCGCATATATGGTGCACTCTCAGTACAATCTGCTCTGATGCCGCATAGTTAA
GCCAGTATACACTCCGCTATCGCTACGTGACTGGGTCATGGCTGCGCCCCGACAC
CCGCCAACACCCGCTGACGCGCCCTGACGGGCTTGTCTGCTCCCGGCATCCGCTT
ACAGACAAGCTGTGACCGTCTCCGGGAGCTGCATGTGTCAGAGGTTTTCACCGTC
ATCACCGAAACGCGCGAGGCAGCTGCGGTAAAGCTCATCAGCGTGGTCGTGAAG
CGATTCACAGATGTCTGCCTGTTCATCCGCGTCCAGCTCGTTGAGTTTCTCCAGAA
GCGTTAATGTCTGGCTTCTGATAAAGCGGGCCATGTTAAGGGCGGTTTTTTCCTG
TTTGGTCACTGATGCCTCCGTGTAAGGGGGATTTCTGTTCATGGGGGTAATGATA
CCGATGAAACGAGAGAGGATGCTCACGATACGGGTTACTGATGATGAACATGCC
CGGTTACTGGAACGTTGTGAGGGTAAACAACTGGCGGTATGGATGCGGCGGGAC
CAGAGAAAATCACTCAGGGTCAATGCCAGCGCTTCGTTAATACAGATGTAGGT
GTTCCACAGGGTAGCCAGCAGCATCCTGCGATGCAGATCCGGAACATAATGGTG
CAGGGCGCTGACTTCCGCGTTTCCAGACTTTACGAAACACGGAAACCGAAGACC
ATTCATGTTGTTGCTCAGGTCGCAGACGTTTTGCAGCAGCAGTCGCTTCACGTTC
GCTCGCGTATCGGTGATTCATTCTGCTAACCAGTAAGGCAACCCCGCCAGCCTAG

Figure 23a (cont.)

```
CCGGGTCCTCAACGACAGGAGCACGATCATGCGCACCCGTGGCCAGGACCCAAC
GCTGCCCGAGATGCGCCGCGTGCGGCTGCTGGAGATGGCGGACGCGATGGATAT
GTTCTGCCAAGGGTTGGTTTGCGCATTCACAGTTCTCCGCAAGAATTGATTGGCT
CCAATTCTTGGAGTGGTGAATCCGTTAGCGAGGTGCCGCCGGCTTCCATTCAGGT
CGAGGTGGCCCGGCTCCATGCACCGCGACGCAACGCGGGGAGGCAGACAAGGTA
TAGGGCGGCGCCTACAATCCATGCCAACCCGTTCCATGTGCTCGCCGAGGCGGCA
TAAATCGCCGTGACGATCAGCGGTCCAGTGATCGAAGTTAGGCTGGTAAGAGCC
GCGAGCGATCCTTGAAGCTGTCCTGATGGTCGTCATCTACCTGCCTGGACAGCA
TGGCCTGCAACGCGGGCATCCCGATGCCGCCGGAAGCGAGAAGAATCATAATGG
GGAAGGCCATCCAGCCTCGCGTCGCGAACGCCAGCAAGACGTAGCCCAGCGCGT
CGGCCGCCATGCCGGCGATAATGGCCTGCTTCTCGCCGAAACGTTTGGTGGCGGG
ACCAGTGACGAAGGCTTGAGCGAGGGCGTGCAAGATTCCGAATACCGCAAGCGA
CAGGCCGATCATCGTCGCGCTCCAGCGAAAGCGGTCCTCGCCGAAAATGACCCA
GAGCGCTGCCGGCACCTGTCCTACGAGTTGCATGATAAAGAAGACAGTCATAAG
TGCGGCGACGATAGTCATGCCCCGCGCCCACCGGAAGGAGCTGACTGGGTTGAA
GGCTCTCAAGGGCATCGGCTCTCCCTTATGCGACTCCTGCATTAGGAAGCAGCCC
AGTAGTAGGTTGAGGCCGTTGAGCACCGCCGCCGCAAGGAATGGTGCATGCAAG
GAGATGGCGCCCAACAGTCCCCGGCCACGGGGCCTGCCACCATACCCACGCCG
AAACAAGCGCTCATGAGCCCGAAGTGGCGAGCCCGATCTTCCCCATCGGTGATG
TCGGCGATATAGGCGCCAGCAACCGCACCTGTGGCGCCGGTGATGCCGGCCACG
ATGCGTCCGGCGTAGAGGATCGAGATCTCGATCCCGCGAAATTAATACGACTCA
CTATAGGGAGACCACAACGGTTTCCCTCTAGAAATAATTTTGTTTAACTTTAAGA
AGGAGATATACCATGGCCAAAACCATCGTTCTTTCGGTCGGCGAGGCTACTCGCA
CTCTGACTGAGATCCAGTCCACCGCAGACCGTCAGATCTTCGAAGAGAAGGTCG
GCCTCTGGTGGGTCGGCTGCGCCTCACGGCTTCGCTCCGTCAAAACGGAGCCAA
GACCGCGTATCGAGTCAACCTAAAACTGGATCAGGCGGACGTCGTTGATTGCTCC
ACCAGCGTCTGCGGCGAGCTTCCGAAAGTGCGCTACACTCAGGTATGGTCGCAC
GACGTGACAATCGTTGCGAATAGCACCGAGGCCTCGCGCAAATCGTTGTACGATT
TGACCAAGTCCCTCGTCGCGACCTCGCAGGTCGAAGATCTTGTCGTCAACCTTGT
GCCGCTGGGCCGTTATGGCTCCAAAACCATCGTTCTTTCGGTCGGCGAGGGTACC
CGCACTCTGACTGAGATCCAGTCCACCGCAGACCGTCAGATCTTCGAAGAGAAG
GTCGGGCCTCTGGTGGGTCGGCTGCGCCTCACGGCTTCGCTCCGTCAAAACGGAG
CCAAGACCGCGTATCGAGTCAACCTAAAACTGGATCAGGCGGACGTCGTTGATT
GCTCCACCAGCGTCTGCGGCGAGCTTCCGAAAGTGCGCTACACTCAGGTATGGTC
GCACGACGTGACAATCGTTGCGAATAGCACCGAGGCCTCGCGCAAATCGTTGTA
CGATTTGACCAAGTCCCTCGTCGCGACCTCGCAGGTCGAAGATCTTGTCGTCAAC
CTTGTGCCGCTGGGCCGTTAAGGCCCTGCGGTGTACCCGTGTGTATGGATCCGGC
TGCTAACAAAGCCCGAAAGGAAGCTGAGTTGGCTGCTGCCACCGCTGAGCAATA
ACTAGCATAACCCCTTGGGGCCTCTAAACGGGTCTTGAGGGGTTTTTTGCTGAAA
GGAGGAACTATATCCGGATATCCACAGGACGGGTGTGGTCGCCATGATCGCGTA
GTCGATAGTGGCTCCAAGTAGCGAAGCGAGCAGGACTGGGCGGCGGCCAAAGCG
GTCGGACAGTGCTCCGAGAACGGGTGCGCATAGAAATTGCATCAACGCATATAG
CGCTAGCAGCACGCCATAGTGACTGGCGATGCTGTCGGAATGGACGATATCCCG
CAAGAGGCCCGGCAGTACCGGCATAACCAAGCCTATGCCTACAGCATCCAGGGT
GACGGTGCCGAGGATGACGATGAGCGCATTGTTAGATTTCATACACGGTGCCTG
ACTGCGTTAGCAATTTAACTGTGATAAACTACCGCATTAAAGCTTATCGATGATA
AGCTGTCAAACATGAA
```

Figure 23b pET2P7K32(am) (SEQ ID:7)
TTCTTAGAAAAACTCATCGAGCATCAAATGAAACTGCAATTTATTCATATCAGGA
TTATCAATACCATATTTTTGAAAAAGCCGTTTCTGTAATGAAGGAGAAAACTCAC
CGAGGCAGTTCCATAGGATGGCAAGATCCTGGTATCGGTCTGCGATTCCGACTCG
TCCAACATCAATACAACCTATTAATTTCCCCTCGTCAAAAATAAGGTTATCAAGT
GAGAAATCACCATGAGTGACGACTGAATCCGGTGAGAATGGCAAAAGCTTATGC
ATTTCTTTCCAGACTTGTTCAACAGGCCAGCCATTACGCTCGTCATCAAAATCACT
CGCATCAACCAAACCGTTATTCATTCGTGATTGCGCCTGAGCGAGACGAAATACG
CGATCGCTGTTAAAAGGACAATTACAAACAGGAATCGAATGCAACCGGCGCAGG
AACACTGCCAGCGCATCAACAATATTTTCACCTGAATCAGGATATTCTTCTAATA
CCTGGAATGCTGTTTTCCCGGGGATCGCAGTGGTGAGTAACCATGCATCATCAGG
AGTACGGATAAAATGCTTGATGGTCGGAAGAGGCATAAATTCCGTCAGCCAGTT
TAGTCTGACCATCTCATCTGTAACATCATTGGCAACGCTACCTTTGCCATGTTTCA
GAAACAACTCTGGCGCATCGGGCTTCCCATACAATCGATAGATTGTCGCACCTGA
TTGCCCGACATTATCGCGAGCCCATTTATACCCATATAAATCAGCATCCATGTTG
GAATTTAATCGCGGCCTCGAGCAAGACGTTTCCCGTTGAATATGGCTCATAACAC
CCCTTGTATTACTGTTTATGTAAGCAGACAGTTTTATTGTTCATGACCAAAATCCC
TTAACGTGAGTTTTCGTTCCACTGAGCGTCAGACCCCGTAGAAAAGATCAAAGGA
TCTTCTTGAGATCCTTTTTTTCTGCGCGTAATCTGCTGCTTGCAAACAAAAAAACC
ACCGCTACCAGCGGTGGTTTGTTTGCCGGATCAAGAGCTACCAACTCTTTTTCCG
AAGGTAACTGGCTTCAGCAGAGCGCAGATACCAAATACTGTCCTTCTAGTGTAGC
CGTAGTTAGGCCACCACTTCAAGAACTCTGTAGCACCGCCTACATACCTCGCTCT
GCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATAC
CTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTT
GAGCGTCGATTTTTGTGATGCTCGTCAGGGGGGCGGAGCCTATGGAAAAACGCC
AGCAACGCGGCCTTTTTACGGTTCCTGGCCTTTTGCTGGCCTTTTGCTCACATGTT
CTTTCCTGCGTTATCCCCTGATTCTGTGGATAACCGTATTACCGCCTTTGAGTGAG
CTGATACCGCTCGCCGCAGCCGAACGACCGAGCGCAGCGAGTCAGTGAGCGAGG
AAGCGGAAGAGCGCCTGATGCGGTATTTTCTCCTTACGCATCTGTGCGGTATTTC
ACACCGCATATATGGTGCACTCTCAGTACAATCTGCTCTGATGCCGCATAGTTAA
GCCAGTATACACTCCGCTATCGCTACGTGACTGGGTCATGGCTGCGCCCCGACAC
CCGCCAACACCCGCTGACGCGCCCTGACGGGCTTGTCTGCTCCCGGCATCCGCTT
ACAGACAAGCTGTGACCGTCTCCGGGAGCTGCATGTGTCAGAGGTTTTCACCGTC
ATCACCGAAACGCGCGAGGCAGCTGCGGTAAAGCTCATCAGCGTGGTCGTGAAG
CGATTCACAGATGTCTGCCTGTTCATCCGCGTCCAGCTCGTTGAGTTTCTCCAGAA
GCGTTAATGTCTGGCTTCTGATAAAGCGGGCCATGTTAAGGGCGGTTTTTTCCTG
TTTGGTCACTGATGCCTCCGTGTAAGGGGGATTTCTGTTCATGGGGGTAATGATA
CCGATGAAACGAGAGAGGATGCTCACGATACGGGTTACTGATGATGAACATGCC
CGGTTACTGGAACGTTGTGAGGGTAAACAACTGGCGGTATGGATGCGGCGGGAC
CAGAGAAAAATCACTCAGGGTCAATGCCAGCGCTTCGTTAATACAGATGTAGGT
GTTCCACAGGGTAGCCAGCAGCATCCTGCGATGCAGATCCGGAACATAATGGTG
CAGGGCGCTGACTTCCGCGTTTCCAGACTTTACGAAACACGGAAACCGAAGACC
ATTCATGTTGTTGCTCAGGTCGCAGACGTTTTGCAGCAGCAGTCGCTTCACGTTC
GCTCGCGTATCGGTGATTCATTCTGCTAACCAGTAAGGCAACCCCGCCAGCCTAG

Figure 23b (cont.)

```
CCGGGTCCTCAACGACAGGAGCACGATCATGCGCACCCGTGGCCAGGACCCAAC
GCTGCCCGAGATGCGCCGCGTGCGGCTGCTGGAGATGGCGGACGCGATGGATAT
GTTCTGCCAAGGGTTGGTTTGCGCATTCACAGTTCTCCGCAAGAATTGATTGGCT
CCAATTCTTGGAGTGGTGAATCCGTTAGCGAGGTGCCGCCGGCTTCCATTCAGGT
CGAGGTGGCCCGGCTCCATGCACCGCGACGCAACGCGGGGAGGCAGACAAGGTA
TAGGGCGGCGCCTACAATCCATGCCAACCCGTTCCATGTGCTCGCCGAGGCGGCA
TAAATCGCCGTGACGATCAGCGGTCCAGTGATCGAAGTTAGGCTGGTAAGAGCC
GCGAGCGATCCTTGAAGCTGTCCCTGATGGTCGTCATCTACCTGCCTGGACAGCA
TGGCCTGCAACGCGGGCATCCCGATGCCGCCGGAAGCGAGAAGAATCATAATGG
GGAAGGCCATCCAGCCTCGCGTCGCAACGCCAGCAAGACGTAGCCCAGCGCGT
CGGCCGCCATGCCGGCGATAATGGCCTGCTTCTCGCCGAAACGTTTGGTGGCGGG
ACCAGTGACGAAGGCTTGAGCGAGGGCGTGCAAGATTCCGAATACCGCAAGCGA
CAGGCCGATCATCGTCGCGCTCCAGCGAAAGCGGTCCTCGCCGAAAATGACCCA
GAGCGCTGCCGGCACCTGTCCTACGAGTTGCATGATAAAGAAGACAGTCATAAG
TGCGGCGACGATAGTCATGCCCCGCGCCACCGGAAGGAGCTGACTGGGTTGAA
GGCTCTCAAGGGCATCGGCTCTCCCTTATGCGACTCCTGCATTAGGAAGCAGCCC
AGTAGTAGGTTGAGGCCGTTGAGCACCGCCGCCGCAAGGAATGGTGCATGCAAG
GAGATGGCGCCCAACAGTCCCCCGGCCACGGGGCCTGCCACCATACCCACGCCG
AAACAAGCGCTCATGAGCCCGAAGTGGCGAGCCCGATCTTCCCCATCGGTGATG
TCGGCGATATAGGCGCCAGCAACCGCACCTGTGGCGCCGGTGATGCCGGCCACG
ATGCGTCCGGCGTAGAGGATCGAGATCTCGATCCCGCGAAATTAATACGACTCA
CTATAGGGAGACCACAACGGTTTCCCTCTAGAAATAATTTTGTTTAACTTTAAGA
AGGAGATATACCATGGCCAAAACCATCGTTCTTTCGGTCGGCGAGGCTACTCGCA
CTCTGACTGAGATCCAGTCCACCGCAGACCGTCAGATCTTCAAGAGAAGGTCG
GGCCTCTGGTGGGTCGGCTGCGCCTCACGGCTTCGCTCCGTCAAAACGGAGCCAA
GACCGCGTATCGAGTCAACCTAAAACTGGATCAGGCGGACGTCGTTGATTGCTCC
ACCAGCGTCTGCGGCGAGCTTCCGAAAGTGCGCTACACTCAGGTATGGTCGCAC
GACGTGACAATCGTTGCGAATAGCACCGAGGCCTCGCGCAAATCGTTGTACGATT
TGACCAAGTCCCTCGTCGCGACCTCGCAGGTCGAAGATCTTGTCGTCAACCTTGT
GCCGCTGGGCCGTTAGGGCTCCAAAACCATCGTTCTTTCGGTCGGCGAGGGTACC
CGCACTCTGACTGAGATCCAGTCCACCGCAGACCGTCAGATCTTCAAGAGAAG
GTCGGGCCTCTGGTGGGTCGGCTGCGCCTCACGGCTTCGCTCCGTCAAAACGGAG
CCAAGACCGCGTATCGAGTCAACCTAAAACTGGATCAGGCGGACGTCGTTGATT
GCTCCACCAGCGTCTGCGGCGAGCTTCCGAAAGTGCGCTACACTCAGGTATGGTC
GCACGACGTGACAATCGTTGCGAATAGCACCGAGGCCTCGCGCAAATCGTTGTA
CGATTTGACCAAGTCCCTCGTCGCGACCTCGCAGGTCGAAGATCTTGTCGTCAAC
CTTGTGCCGCTGGGCCGTTAAGGCCCTGCGGTGTACCCGTGTGTATGGATCCGGC
TGCTAACAAAGCCCGAAAGGAAGCTGAGTTGGCTGCTGCCACCGCTGAGCAATA
ACTAGCATAACCCCTTGGGGCCTCTAAACGGGTCTTGAGGGGTTTTTTGCTGAAA
GGAGGAACTATATCCGGATATCCACAGGACGGGTGTGGTCGCCATGATCGCGTA
GTCGATAGTGGCTCCAAGTAGCGAAGCGAGCAGGACTGGGCGGCGGCCAAAGCG
GTCGGACAGTGCTCCGAGAACGGGTGCGCATAGAAATTGCATCAACGCATATAG
CGCTAGCAGCACGCCATAGTGACTGGCGATGCTGTCGGAATGGACGATATCCCG
CAAGAGGCCCGGCAGTACCGGCATAACCAAGCCTATGCCTACAGCATCCAGGGT
GACGGTGCCGAGGATGACGATGAGCGCATTGTTAGATTTCATACACGGTGCCTG
ACTGCGTTAGCAATTTAACTGTGATAAACTACCGCATTAAAGCTTATCGATGATA
AGCTGTCAAACATGAA
```

Figure 23c pDSP7 (SEQ ID:8)
TTCTTAGAAAAACTCATCGAGCATCAAATGAAACTGCAATTTATTCATATCAGGA
TTATCAATACCATATTTTTGAAAAAGCCGTTTCTGTAATGAAGGAGAAAACTCAC
CGAGGCAGTTCCATAGGATGGCAAGATCCTGGTATCGGTCTGCGATTCCGACTCG
TCCAACATCAATACAACCTATTAATTTCCCCTCGTCAAAAATAAGGTTATCAAGT
GAGAAATCACCATGAGTGACGACTGAATCCGGTGAGAATGGCAAAAGCTTATGC
ATTTCTTTCCAGACTTGTTCAACAGGCCAGCCATTACGCTCGTCATCAAAATCACT
CGCATCAACCAAACCGTTATTCATTCGTGATTGCGCCTGAGCGAGACGAAATACG
CGATCGCTGTTAAAAGGACAATTACAAACAGGAATCGAATGCAACCGGCGCAGG
AACACTGCCAGCGCATCAACAATATTTTCACCTGAATCAGGATATTCTTCTAATA
CCTGGAATGCTGTTTTCCCGGGGATCGCAGTGGTGAGTAACCATGCATCATCAGG
AGTACGGATAAAATGCTTGATGGTCGGAAGAGGCATAAATTCCGTCAGCCAGTT
TAGTCTGACCATCTCATCTGTAACATCATTGGCAACGCTACCTTTGCCATGTTTCA
GAAACAACTCTGGCGCATCGGGCTTCCCATACAATCGATAGATTGTCGCACCTGA
TTGCCCGACATTATCGCGAGCCCATTTATACCCATATAAATCAGCATCCATGTTG
GAATTTAATCGCGGCCTCGAGCAAGACGTTTCCCGTTGAATATGGCTCATAACAC
CCCTTGTATTACTGTTTATGTAAGCAGACAGTTTTATTGTTCATGACCAAAATCCC
TTAACGTGAGTTTTCGTTCCACTGAGCGTCAGACCCCGTAGAAAAGATCAAAGGA
TCTTCTTGAGATCCTTTTTTTCTGCGCGTAATCTGCTGCTTGCAAACAAAAAAACC
ACCGCTACCAGCGGTGGTTTGTTTGCCGGATCAAGAGCTACCAACTCTTTTTCCG
AAGGTAACTGGCTTCAGCAGAGCGCAGATACCAAATACTGTCCTTCTAGTGTAGC
CGTAGTTAGGCCACCACTTCAAGAACTCTGTAGCACCGCCTACATACCTCGCTCT
GCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATAC
CTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTT
GAGCGTCGATTTTTGTGATGCTCGTCAGGGGGGCGGAGCCTATGGAAAAACGCC
AGCAACGCGGCCTTTTTACGGTTCCTGGCCTTTTGCTGGCCTTTTGCTCACATGTT
CTTTCCTGCGTTATCCCCTGATTCTGTGGATAACCGTATTACCGCCTTTGAGTGAG
CTGATACCGCTCGCCGCAGCCGAACGACCGAGCGCAGCGAGTCAGTGAGCGAGG
AAGCGGAAGAGCGCCTGATGCGGTATTTTCTCCTTACGCATCTGTGCGGTATTTC
ACACCGCATATATGGTGCACTCTCAGTACAATCTGCTCTGATGCCGCATAGTTAA
GCCAGTATACACTCCGCTATCGCTACGTGACTGGGTCATGGCTGCGCCCCGACAC
CCGCCAACACCCGCTGACGCGCCCTGACGGGCTTGTCTGCTCCCGGCATCCGCTT
ACAGACAAGCTGTGACCGTCTCCGGGAGCTGCATGTGTCAGAGGTTTTCACCGTC
ATCACCGAAACGCGCGAGGCAGCTGCGGTAAAGCTCATCAGCGTGGTCGTGAAG
CTTTTCAAAATTGTAAACGTTAATATTTTGTTAAAATTCGCGTTAAATTTTTGTTA
AATCAGCTCATTTTTTAACCAATAGGCCGAAATCGGCAAAATCCCTTATAAATCA
AAAGAATAGCCCGAGATAGGGTTGAGTGTTGTTCCAGTTTGGAACAAGAGTCCA
CTATTAAAGAACGTGGACTCCAACGTCAAAGGGCGAAAAACCGTCTATCAGGGC
GATGGCCCACTACGTGAACCATCACCCAAATCAAGTTTTGGGGTCGAGGTGCCG
TAAAGCACTAAATCGGAACCCTAAAGGGAGCCCCCGATTTAGAGCTTGACGGGG
AAAGCCGGCGAACGTGGCGAGAAAGGAAGGGAAGAAAGCGAAAGGAGCGGGC
GCTAGGGCGCTGGCAAGTGTAGCGGTCACGCTGCGCGTAACCACCACACCCGCC
GCGCTTAATGCGCCGCTACAGGGCGCGTACTATGGTTGCTTTGACGTCGGCCGCC
ATGCCGGCGATAATGGCCTGCTTCTCGCCGAAACGTTTGGTGGCGGGACCAGTGA

Figure 23c (cont.)

CGAAGGCTTGAGCGAGGGCGTGCAAGATTCCGAATACCGCAAGCGACAGGCCGA
TCATCGTCGCGCTCCAGCGAAAGCGGTCCTCGCCGAAAATGACCCAGAGCGCTG
CCGGCACCTGTCCTACGAGTTGCATGATAAAGAAGACAGTCATAAGTGCGGCGA
CGATAGTCATGCCCCGCGCCCACCGGAAGGAGCTGACTGGGTTGAAGGCTCTCA
AGGGCATCGGCTCTCCCTTATGCGACTCCTGCATTAGGAAGCAGCCCAGTAGTAG
GTTGAGGCCGTTGAGCACCGCCGCCGCAAGGAATGGTGCATGCAAGGAGATGGC
GCCCAACAGTCCCCCGGCCACGGGGCCTGCCACCATACCCACGCCGAAACAAGC
GCTCATGAGCCCGAAGTGGCGAGCCCGATCTTCCCCATCGGTGATGTCGGCGATA
TAGGCGCCAGCAACCGCACCTGTGGCGCCGGTGATGCCGGCCACGATGCGTCCG
GCGTAGAGGATCGAGATCTCGATCCCGCGAAATTAATACGACTCACTATAGGGA
GACCACAACGGTTTCCCTCTAGAAATAATTTTGTTTAACTTTAAGAAGGAGATAT
ACCATGGCAAAGACGATAGTATTGAGCGTAGGGGAAGCAACGAGAACGTTAACG
GAAATACAAAGTACGGCTGATAGACAAATATTTGAGGAAAAAGTAGGTCCGTTA
GTTGGGAGATTAAGATTGACCGCAAGCTTGAGACAGAATGGTGCAAAAACGGCT
TACAGGGTAAATTTGAAGTTAGACCAAGCTGATGTAGTAGACTGTAGTACGTCA
GTATGTGGGGAATTGCCTAAGGTTAGATATACGCAAGTTTGGAGCCATGATGTTA
CCATAGTAGCTAACTCAACGGAAGCAAGCAGAAAGAGCCTCTATGACCTCACGA
AAAGTTTGGTAGCTACGAGCCAAGTAGAGGACTTGGTAGTAAATTTGGTTCCTTT
AGGCCGTTATGGCTCCAAAACCATCGTTCTTTCGGTCGGCGAGGGTACCCGCACT
CTGACTGAGATCCAGTCCACCGCAGACCGTCAGATCTTCGAAGAGAAGGTCGGG
CCTCTGGTGGGTCGGCTGCGCCTCACGGCTTCGCTCCGTCAAAACGGAGCCAAGA
CCGCGTATCGAGTCAACCTAAAACTGGATCAGGCGGACGTCGTTGATTGCTCCAC
CAGCGTCTGCGGCGAGCTTCCGAAAGTGCGCTACACTCAGGTATGGTCGCACGA
CGTGACAATCGTTGCGAATAGCACCGAGGCCTCGCGCAAATCGTTGTACGATTTG
ACCAAGTCCCTCGTCGCGACCTCGCAGGTCGAAGATCTTGTCGTCAACCTTGTGC
CGCTGGGCCGTTAAGGCCCTGCGGTGTACCCGTGTGTATGGATCCGGCTGCTAAC
AAAGCCCGAAAGGAAGCTGAGTTGGCTGCTGCCACCGCTGAGCAATAACTAGCA
TAACCCCTTGGGGCCTCTAAACGGGTCTTGAGGGGTTTTTTGCTGAAAGGAGGAA
CTATATCCGGATATCCACAGGACGGGTGTGGTCGCCATGATCGCGTAGTCGATAG
TGGCTCCAAGTAGCGAAGCGAGCAGGACTGGGCGGCGGCCAAAGCGGTCGGAC
AGTGCTCCGAGAACGGGTGCGCATAGAAATTGCATCAACGCATATAGCGCTAGC
AGCACGCCATAGTGACTGGCGATGCTGTCGGAATGGACGATATCCCGCAAGAGG
CCCGGCAGTACCGGCATAACCAAGCCTATGCCTACAGCATCCAGGGTGACGGTG
CCGAGGATGACGATGAGCGCATTGTTAGATTTCATACACGGTGCCTGACTGCGTT
AGCAATTTAACTGTGATAAACTACCGCATTAAAGCTTATCGATGATAAGCTGTCA
AACATGAA

Figure 23d pDSP7(am) (SEQ ID: 9)
TTCTTAGAAAAACTCATCGAGCATCAAATGAAACTGCAATTTATTCATATCAGGA
TTATCAATACCATATTTTTGAAAAAGCCGTTTCTGTAATGAAGGAGAAAACTCAC
CGAGGCAGTTCCATAGGATGGCAAGATCCTGGTATCGGTCTGCGATTCCGACTCG
TCCAACATCAATACAACCTATTAATTTCCCCTCGTCAAAAATAAGGTTATCAAGT
GAGAAATCACCATGAGTGACGACTGAATCCGGTGAGAATGGCAAAAGCTTATGC
ATTTCTTTCCAGACTTGTTCAACAGGCCAGCCATTACGCTCGTCATCAAAATCACT
CGCATCAACCAAACCGTTATTCATTCGTGATTGCGCCTGAGCGAGACGAAATACG
CGATCGCTGTTAAAAGGACAATTACAAACAGGAATCGAATGCAACCGGCGCAGG
AACACTGCCAGCGCATCAACAATATTTTCACCTGAATCAGGATATTCTTCTAATA
CCTGGAATGCTGTTTTCCCGGGGATCGCAGTGGTGAGTAACCATGCATCATCAGG
AGTACGGATAAAATGCTTGATGGTCGGAAGAGGCATAAATTCCGTCAGCCAGTT
TAGTCTGACCATCTCATCTGTAACATCATTGGCAACGCTACCTTTGCCATGTTTCA
GAAACAACTCTGGCGCATCGGGCTTCCCATACAATCGATAGATTGTCGCACCTGA
TTGCCCGACATTATCGCGAGCCCATTTATACCCATATAAATCAGCATCCATGTTG
GAATTTAATCGCGGCCTCGAGCAAGACGTTTCCCGTTGAATATGGCTCATAACAC
CCCTTGTATTACTGTTTATGTAAGCAGACAGTTTTATTGTTCATGACCAAAATCCC
TTAACGTGAGTTTTCGTTCCACTGAGCGTCAGACCCCGTAGAAAAGATCAAAGGA
TCTTCTTGAGATCCTTTTTTTCTGCGCGTAATCTGCTGCTTGCAAACAAAAAAACC
ACCGCTACCAGCGGTGGTTTGTTTGCCGGATCAAGAGCTACCAACTCTTTTTCCG
AAGGTAACTGGCTTCAGCAGAGCGCAGATACCAAATACTGTCCTTCTAGTGTAGC
CGTAGTTAGGCCACCACTTCAAGAACTCTGTAGCACCGCCTACATACCTCGCTCT
GCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATAC
CTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTT
GAGCGTCGATTTTTGTGATGCTCGTCAGGGGGGCGGAGCCTATGGAAAAACGCC
AGCAACGCGGCCTTTTTACGGTTCCTGGCCTTTTGCTGGCCTTTTGCTCACATGTT
CTTTCCTGCGTTATCCCCTGATTCTGTGGATAACCGTATTACCGCCTTTGAGTGAG
CTGATACCGCTCGCCGCAGCCGAACGACCGAGCGCAGCGAGTCAGTGAGCGAGG
AAGCGGAAGAGCGCCTGATGCGGTATTTTCTCCTTACGCATCTGTGCGGTATTTC
ACACCGCATATATGGTGCACTCTCAGTACAATCTGCTCTGATGCCGCATAGTTAA
GCCAGTATACACTCCGCTATCGCTACGTGACTGGGTCATGGCTGCGCCCCGACAC
CCGCCAACACCCGCTGACGCGCCCTGACGGGCTTGTCTGCTCCCGGCATCCGCTT
ACAGACAAGCTGTGACCGTCTCCGGGAGCTGCATGTGTCAGAGGTTTTCACCGTC
ATCACCGAAACGCGCGAGGCAGCTGCGGTAAAGCTCATCAGCGTGGTCGTGAAG
CTTTTCAAAATTGTAAACGTTAATATTTTGTTAAAATTCGCGTTAAATTTTGTTA
AATCAGCTCATTTTTTAACCAATAGGCCGAAATCGGCAAAATCCCTTATAAATCA
AAAGAATAGCCCGAGATAGGGTTGAGTGTTGTTCCAGTTTGGAACAAGAGTCCA
CTATTAAAGAACGTGGACTCCAACGTCAAAGGGCGAAAAACCGTCTATCAGGGC
GATGGCCCACTACGTGAACCATCACCCAAATCAAGTTTTTGGGGTCGAGGTGCCG
TAAAGCACTAAATCGGAACCCTAAAGGGAGCCCCGATTTAGAGCTTGACGGGG
AAAGCCGGCGAACGTGGCGAGAAAGGAAGGGAAGAAAGCGAAAGGAGCGGGC
GCTAGGGCGCTGGCAAGTGTAGCGGTCACGCTGCGCGTAACCACCACACCCGCC
GCGCTTAATGCGCCGCTACAGGGCGCGTACTATGGTTGCTTTGACGTCGGCCGCC
ATGCCGGCGATAATGGCCTGCTTCTCGCCGAAACGTTTGGTGGCGGGACCAGTGA

Figure 23d (cont.)

CGAAGGCTTGAGCGAGGGCGTGCAAGATTCCGAATACCGCAAGCGACAGGCCGA
TCATCGTCGCGCTCCAGCGAAAGCGGTCCTCGCCGAAAATGACCCAGAGCGCTG
CCGGCACCTGTCCTACGAGTTGCATGATAAAGAAGACAGTCATAAGTGCGGCGA
CGATAGTCATGCCCCGCGCCCACCGGAAGGAGCTGACTGGGTTGAAGGCTCTCA
AGGGCATCGGCTCTCCCTTATGCGACTCCTGCATTAGGAAGCAGCCCAGTAGTAG
GTTGAGGCCGTTGAGCACCGCCGCCGCAAGGAATGGTGCATGCAAGGAGATGGC
GCCCAACAGTCCCCCGGCCACGGGGCCTGCCACCATACCCACGCCGAAACAAGC
GCTCATGAGCCCGAAGTGGCGAGCCCGATCTTCCCCATCGGTGATGTCGGCGATA
TAGGCGCCAGCAACCGCACCTGTGGCGCCGGTGATGCCGGCCACGATGCGTCCG
GCGTAGAGGATCGAGATCTCGATCCCGCGAAATTAATACGACTCACTATAGGGA
GACCACAACGGTTTCCCTCTAGAAATAATTTTGTTTAACTTTAAGAAGGAGATAT
ACCATGGCAAAGACGATAGTATTGAGCGTAGGGGAAGCAACGAGAACGTTAACG
GAAATACAAAGTACGGCTGATAGACAAATATTTGAGGAAAAAGTAGGTCCGTTA
GTTGGGAGATTAAGATTGACCGCAAGCTTGAGACAGAATGGTGCAAAAACGGCT
TACAGGGTAAATTTGAAGTTAGACCAAGCTGATGTAGTAGACTGTAGTACGTCA
GTATGTGGGGAATTGCCTAAGGTTAGATATACGCAAGTTTGGAGCCATGATGTTA
CCATAGTAGCTAACTCAACGGAAGCAAGCAGAAAGAGCCTCTATGACCTCACGA
AAAGTTTGGTAGCTACGAGCCAAGTAGAGGACTTGGTAGTAAATTTGGTTCCTTT
AGGCCGTTAGGGCTCCAAAACCATCGTTCTTTCGGTCGGCGAGGGTACCCGCACT
CTGACTGAGATCCAGTCCACCGCAGACCGTCAGATCTTCGAAGAGAAGGTCGGG
CCTCTGGTGGGTCGGCTGCGCCTCACGGCTTCGCTCCGTCAAAACGGAGCCAAGA
CCGCGTATCGAGTCAACCTAAAACTGGATCAGGCGGACGTCGTTGATTGCTCCAC
CAGCGTCTGCGGCGAGCTTCCGAAAGTGCGCTACACTCAGGTATGGTCGCACGA
CGTGACAATCGTTGCGAATAGCACCGAGGCCTCGCGCAAATCGTTGTACGATTTG
ACCAAGTCCCTCGTCGCGACCTCGCAGGTCGAAGATCTTGTCGTCAACCTTGTGC
CGCTGGGCCGTTAAGGCCCTGCGGTGTACCCGTGTGTATGGATCCGGCTGCTAAC
AAAGCCCGAAAGGAAGCTGAGTTGGCTGCTGCCACCGCTGAGCAATAACTAGCA
TAACCCCTTGGGGCCTCTAAACGGGTCTTGAGGGGTTTTTTGCTGAAAGGAGGAA
CTATATCCGGATATCCACAGGACGGGTGTGGTCGCCATGATCGCGTAGTCGATAG
TGGCTCCAAGTAGCGAAGCGAGCAGGACTGGGCGGCGGCCAAAGCGGTCGGAC
AGTGCTCCGAGAACGGGTGCGCATAGAAATTGCATCAACGCATATAGCGCTAGC
AGCACGCCATAGTGACTGGCGATGCTGTCGGAATGGACGATATCCCGCAAGAGG
CCCGGCAGTACCGGCATAACCAAGCCTATGCCTACAGCATCCAGGGTGACGGTG
CCGAGGATGACGATGAGCGCATTGTTAGATTTCATACACGGTGCCTGACTGCGTT
AGCAATTTAACTGTGATAAACTACCGCATTAAAGCTTATCGATGATAAGCTGTCA
AACATGAA

SEQUENCE LISTING

```
<160> NUMBER OF SEQ ID NOS: 48

<210> SEQ ID NO 1
<211> LENGTH: 5096
<212> TYPE: DNA
<213> ORGANISM: Artificial Sequence
<220> FEATURE:
<223> OTHER INFORMATION: pDSP1 plasmid

<400> SEQUENCE: 1
ttcttagaaa aactcatcga gcatcaaatg aaactgcaat ttattcatat caggattatc      60
aataccatat ttttgaaaaa gccgtttctg taatgaagga gaaaactcac cgaggcagtt     120
ccataggatg gcaagatcct ggtatcggtc tgcgattccg actcgtccaa catcaataca     180
acctattaat ttcccctcgt caaaaataag gttatcaagt gagaaatcac catgagtgac     240
gactgaatcc ggtgagaatg gcaaaagctt atgcatttct ttccagactt gttcaacagg     300
ccagccatta cgctcgtcat caaaatcact cgcatcaacc aaaccgttat tcattcgtga     360
ttgcgcctga gcgagacgaa atacgcgatc gctgttaaaa ggacaattac aaacaggaat     420
cgaatgcaac cggcgcagga acactgccag cgcatcaaca atattttcac ctgaatcagg     480
atattcttct aatacctgga atgctgtttt cccggggatc gcagtggtga gtaaccatgc     540
atcatcagga gtacggataa aatgcttgat ggtcggaaga gcataaatt ccgtcagcca     600 gtttagtctg accatctcat ctgtaacatc attggcaacg ctacctttgc catgtttcag     660
aaacaactct ggcgcatcgg gcttcccata caatcgatag attgtcgcac ctgattgccc     720
gacattatcg cgagcccatt tatacccata taaatcagca tccatgttgg aatttaatcg     780
cggcctcgag caagacgttt cccgttgaat atggctcata cacccccttg tattactgtt     840
tatgtaagca gacagtttta ttgttcatga ccaaaatccc ttaacgtgag ttttcgttcc     900
actgagcgtc agacccgta gaaagatca aaggatcttc ttgagatcct ttttttctgc     960
```

```
gcgtaatctg ctgcttgcaa acaaaaaaac caccgctacc agcggtggtt tgtttgccgg    1020
atcaagagct accaactctt tttccgaagg taactggctt cagcagagcg cagataccaa    1080
atactgtcct tctagtgtag ccgtagttag gccaccactt caagaactct gtagcaccgc    1140
ctacatacct cgctctgcta atcctgttac cagtggctgc tgccagtggc gataagtcgt    1200
gtcttaccgg gttggactca agacgatagt taccggataa ggcgcagcgg tcgggctgaa    1260
cggggggttc gtgcacacag cccagcttgg agcgaacgac ctacaccgaa ctgagatacc    1320
tacagcgtga gctatgagaa agcgccacgc ttcccgaagg agaaaggcg acaggtatc      1380 cggtaagcgg cagggtcgga acaggagagc gcacgaggga gcttccaggg ggaaacgcct    1440
ggtatcttta tagtcctgtc gggtttcgcc acctctgact tgagcgtcga ttttgtgat     1500 gctcgtcagg ggggcggagc ctatggaaaa acgccagcaa cgcggccttt ttacggttcc    1560
tggccttttg ctggcctttt gctcacatgt tctttcctgc gttatcccct gattctgtgg    1620
ataaccgtat taccgccttt gagtgagctg ataccgctcg ccgcagccga acgaccgagc    1680
gcagcgagtc agtgagcgag gaagcggaag agcgcctgat gcggtatttt ctccttacgc    1740
atctgtgcgg tatttcacac cgcatatatg gtgcactctc agtacaatct gctctgatgc    1800
cgcatagtta agccagtata cactccgcta tcgctacgtg actgggtcat ggctgcgccc    1860
cgacacccgc caacacccgc tgacgcgccc tgacgggctt gtctgctccc ggcatccgct    1920
tacagacaag ctgtgaccgt ctccgggagc tgcatgtgtc agaggttttc accgtcatca    1980
ccgaaacgcg cgaggcagct gcggtaaagc tcatcagcgt ggtcgtgaag cgattcacag    2040
atgtctgcct gttcatccgc gtccagctcg ttgagtttct ccagaagcgt taatgtctgg    2100
cttctgataa agcgggccat gttaagggcg gttttttcct gtttggtcac tgatgcctcc    2160
gtgtaagggg gatttctgtt catggggta atgataccga tgaaacgaga gaggatgctc     2220
acgatacggg ttactgatga tgaacatgcc cggttactgg aacgttgtga gggtaaacaa    2280
ctggcggtat ggatgcggcg ggaccagaga aaaatcactc agggtcaatg ccagcgcttc    2340
gttaatacag atgtaggtgt tccacagggt agccagcagc atcctgcgat gcagatccgg    2400
aacataatgg tgcagggcgc tgacttccgc gtttccagac tttacgaaac acggaaaccg    2460
aagaccattc atgttgttgc tcaggtcgca gacgttttgc agcagcagtc gcttcacgtt    2520
cgctcgcgta tcggtgattc attctgctaa ccagtaaggc aaccccgcca gcctagccgg    2580
gtcctcaacg acaggagcac gatcatgcgc acccgtggcc aggacccaac gctgcccgag    2640
atgcgccgcg tgcggctgct ggagatggcg gacgcgatgg atatgttctg ccaagggttg    2700
gtttgcgcat tcacagttct ccgcaagaat tgattggctc caattcttgg agtggtgaat    2760
ccgttagcga ggtgccgccg gcttccattc aggtcgaggt ggcccggctc catgcaccgc    2820
gacgcaacgc ggggaggcag acaaggtata gggcggcgcc tacaatccat gccaacccgt    2880
tccatgtgct cgccgaggcg gcataaatcg ccgtgacgat cagcggtcca gtgatcgaag    2940
ttaggctggt aagagccgcg agcgatcctt gaagctgtcc ctgatggtcg tcatctacct    3000
gcctggacag catggcctgc aacgcgggca tcccgatgcc gccggaagcg agaagaatca    3060 taatgggaa ggccatccag cctcgcgtcg cgaacgccag caagacgtag cccagcgcgt     3120
cggccgccat gccggcgata atggcctgct tctcgccgaa acgtttggtg cgggaccag     3180 tgacgaaggc ttgagcgagg gcgtgcaaga ttccgaatac cgcaagcgac aggccgatca    3240
tcgtcgcgct ccagcgaaag cggtcctcgc cgaaaatgac ccagagcgct gccggcacct    3300
```

-continued

```
gtcctacgag ttgcatgata agaagacag tcataagtgc ggcgacgata gtcatgcccc    3360
gcgcccaccg gaaggagctg actgggttga aggctctcaa gggcatcggc tctcccttat    3420
gcgactcctg cattaggaag cagcccagta gtaggttgag gccgttgagc accgccgccg    3480
caaggaatgg tgcatgcaag gagatggcgc ccaacagtcc cccggccacg gggcctgcca    3540
ccatacccac gccgaaacaa gcgctcatga gcccgaagtg gcgagcccga tcttccccat    3600
cggtgatgtc ggcgatatag gcgccagcaa ccgcacctgt ggcgccggtg atgccggcca    3660
cgatgcgtcc ggcgtagagg atcgagatct cgatcccgcg aaattaatac gactcactat    3720
agggagacca caacggtttc cctctagaaa taattttgtt taactttaag aaggagatat    3780
accatggctt ctaactttac tcagttcgtt ctcgttgaca atggcggaac tggcgacgtg    3840
actgtcgccc caagcaactt cgctaacggg gtcgctgaat ggatcagctc taactcgcgt    3900
tcacaggctt acaaagtaac ctgtagcgtt cgtcagagct ctgcgcagaa tcgcaaatac    3960
accatcaaag tcgaggtgcc taaagtggca acccagactg ttggtggtgt agagcttcct    4020
gtagccgcat ggcgttcgta cttaaatatg gaactaacca ttccaatttt cgctacgaat    4080
tccgactgcg agcttattgt taaggcaatg caaggtctcc taaaagatgg aaacccgatt    4140
ccctcagcaa tcgcagcaaa ctccggcctc tacggcaact ttactcagtt cgttctcgtc    4200
gacaatggcg gtaccggcga cgtgactgtc gccccaagca acttcgctaa cggggtcgct    4260
gaatggatca gctctaactc gcgttcacag gcttacaaag taacctgtag cgttcgtcag    4320
agctctgcgc agaatcgcaa atacaccatc aaagtcgagg tgcctaaagt ggcaacccag    4380
actgttggtg gtgtagagct tcctgtagcc gcatggcgtt cgtacttaaa tatgaaacta    4440
accattccaa ttttcgctac gaattccgac tgcgagctta ttgttaaggc aatgcaaggt    4500
ctcctaaaag atgaaacccc gattccctca gcaatcgcag caaactccgg catctactaa    4560
tagacgccgg gttaattaat taaggatccg gctgctaaca aagcccgaaa ggaagctgag    4620
ttggctgctg ccaccgctga gcaataacta gcataacccc ttggggcctc taaacgggtc    4680
ttgaggggtt ttttgctgaa aggaggaact atatccggat atccacagga cgggtgtggt    4740
cgccatgatc gcgtagtcga tagtggctcc aagtagcgaa gcgagcagga ctgggcggcg    4800
gccaaagcgg tcggacagtg ctccgagaac gggtgcgcat agaaattgca tcaacgcata    4860
tagcgctagc agcacgccat agtgactggc gatgctgtcg gaatggacga tatcccgcaa    4920
gaggcccggc agtaccggca taaccaagcc tatgcctaca gcatccaggg tgacggtgcc    4980
gaggatgacg atgagcgcat tgttagattt catacacggt gcctgactgc gttagcaatt    5040
taactgtgat aaactaccgc attaaagctt atcgatgata agctgtcaaa catgaa       5096
```

<210> SEQ ID NO 2
<211> LENGTH: 5096
<212> TYPE: DNA
<213> ORGANISM: Artificial Sequence
<220> FEATURE:
<223> OTHER INFORMATION: pDSP1(am) plasmid

<400> SEQUENCE: 2

```
ttcttagaaa aactcatcga gcatcaaatg aaactgcaat ttattcatat caggattatc      60
aataccatat ttttgaaaaa gccgtttctg taatgaagga gaaaactcac cgaggcagtt     120
ccataggatg gcaagatcct ggtatcggtc tgcgattccg actcgtccaa catcaataca     180
acctattaat ttcccctcgt caaaaataag gttatcaagt gagaaatcac catgagtgac     240
gactgaatcc ggtgagaatg gcaaaagctt atgcatttct ttccagactt gttcaacagg     300
```

```
ccagccatta cgctcgtcat caaaatcact cgcatcaacc aaaccgttat tcattcgtga      360
ttgcgcctga gcgagacgaa atacgcgatc gctgttaaaa ggacaattac aaacaggaat      420
cgaatgcaac cggcgcagga acactgccag cgcatcaaca atattttcac ctgaatcagg      480
atattcttct aatacctgga atgctgtttt cccggggatc gcagtggtga gtaaccatgc      540
atcatcagga gtacggataa aatgcttgat ggtcggaaga ggcataaatt ccgtcagcca      600
gtttagtctg accatctcat ctgtaacatc attggcaacg ctaccttgc catgtttcag       660 aaacaactct ggcgcatcgg gcttcccata caatcgatag attgtcgcac ctgattgccc      720
gacattatcg cgagcccatt tatacccata taaatcagca tccatgttgg aatttaatcg      780
cggcctcgag caagacgttt cccgttgaat atggctcata cacccttg tattactgtt        840 tatgtaagca gacagttta ttgttcatga ccaaaatccc ttaacgtgag ttttcgttcc       900
actgagcgtc agacccgta gaaaagatca aggatcttc ttgagatcct ttttctgc          960 gcgtaatctg ctgcttgcaa acaaaaaaac caccgctacc agcggtggtt tgtttgccgg     1020
atcaagagct accaactctt tttccgaagg taactggctt cagcagagcg cagataccaa     1080
atactgtcct tctagtgtag ccgtagttag gccaccactt caagaactct gtagcaccgc     1140
ctacatacct cgctctgcta atcctgttac cagtggctgc tgccagtggc gataagtcgt     1200
gtcttaccgg gttggactca agacgatagt taccggataa ggcgcagcgg tcgggctgaa     1260
cggggggttc gtgcacacag cccagcttgg agcgaacgac ctacaccgaa ctgagatacc     1320
tacagcgtga gctatgagaa agcgccacgc ttcccgaagg gagaaaggcg acaggtatc      1380 cggtaagcgg cagggtcgga acaggagagc gcacgaggga gcttccaggg ggaaacgcct     1440
ggtatcttta tagtcctgtc gggtttcgcc acctctgact tgagcgtcga ttttgtgat     1500 gctcgtcagg ggggcggagc ctatggaaaa acgccagcaa cgcggccttt ttacggttcc     1560
tggccttttg ctggccttt gctcacatgt tctttcctgc gttatcccct gattctgtgg     1620
ataaccgtat taccgccttt gagtgagctg ataccgctcg ccgcagccga acgaccgagc     1680
gcagcgagtc agtgagcgag gaagcggaag agcgcctgat gcggtatttt ctccttacgc     1740
atctgtgcgg tatttcacac cgcatatatg gtgcactctc agtacaatct gctctgatgc     1800
cgcatagtta agccagtata cactccgcta tcgctacgtg actgggtcat ggctgcgccc     1860
cgacacccgc caacacccgc tgacgcgccc tgacgggctt gtctgctccc ggcatccgct     1920
tacagacaag ctgtgaccgt ctccgggagc tgcatgtgtc agaggttttc accgtcatca     1980
ccgaaacgcg cgaggcagct gcggtaaagc tcatcagcgt ggtcgtgaag cgattcacag     2040
atgtctgcct gttcatccgc gtccagctcg ttgagtttct ccagaagcgt taatgtctgg     2100
cttctgataa agcgggccat gttaaggcg gttttttcct gtttggtcac tgatgcctcc      2160
gtgtaagggg gatttctgtt catggggta atgataccga tgaaacgaga gaggatgctc      2220
acgatacggg ttactgatga tgaacatgcc cggttactgg aacgttgtga gggtaaacaa     2280
ctggcggtat ggatgcggcg ggaccagaga aaaatcactc agggtcaatg ccagcgcttc     2340
gttaatacag atgtaggtgt tccacagggt agccagcagc atcctgcgat gcagatccgg     2400
aacataatgg tgcagggcgc tgacttccgc gtttccagac tttacgaaac acggaaaccg     2460
aagaccattc atgttgttgc tcaggtcgca gacgttttgc agcagcagtc gcttcacgtt     2520
cgctcgcgta tcggtgattc attctgctaa ccagtaaggc aaccccgcca gcctagccgg     2580
gtcctcaacg acaggagcac gatcatgcgc acccgtggcc aggacccaac gctgcccgag     2640
```

-continued

```
atgcgccgcg tgcggctgct ggagatggcg gacgcgatgg atatgttctg ccaagggttg    2700
gtttgcgcat tcacagttct ccgcaagaat tgattggctc caattcttgg agtggtgaat    2760
ccgttagcga ggtgccgccg gcttccattc aggtcgaggt ggcccggctc catgcaccgc    2820
gacgcaacgc ggggaggcag acaaggtata gggcggcgcc tacaatccat gccaacccgt    2880
tccatgtgct cgccgaggcg gcataaatcg ccgtgacgat cagcggtcca gtgatcgaag    2940
ttaggctggt aagagccgcg agcgatcctt gaagctgtcc ctgatggtcg tcatctacct    3000
gcctggacag catggcctgc aacgcgggca tcccgatgcc gccggaagcg agaagaatca    3060
taatggggaa ggccatccag cctcgcgtcg cgaacgccag caagacgtag cccagcgcgt    3120
cggccgccat gccggcgata atggcctgct tctcgccgaa acgtttggtg gcgggaccag    3180
tgacgaaggc ttgagcgagg gcgtgcaaga ttccgaatac cgcaagcgac aggccgatca    3240
tcgtcgcgct ccagcgaaag cggtcctcgc cgaaaatgac ccagagcgct gccggcacct    3300
gtcctacgag ttgcatgata agaagacag tcataagtgc ggcgacgata gtcatgcccc    3360
gcgcccaccg gaaggagctg actgggttga aggctctcaa gggcatcggc tctcccttat    3420
gcgactcctg cattaggaag cagcccagta gtaggttgag gccgttgagc accgccgccg    3480
caaggaatgg tgcatgcaag gagatggcgc ccaacagtcc cccggccacg gggcctgcca    3540
ccatacccac gccgaaacaa gcgctcatga gcccgaagtg gcgagcccga tcttccccat    3600
cggtgatgtc ggcgatatag gcgccagcaa ccgcacctgt ggcgccggtg atgccggcca    3660
cgatgcgtcc ggcgtagagg atcgagatct cgatcccgcg aaattaatac gactcactat    3720
agggagacca acgcgtttc cctctagaaa taattttgtt taactttaag aaggagatat    3780
acaatggctt ctaactttac tcagttcgtt ctcgttgaca atggcggaac tggcgacgtg    3840
actgtcgccc caagcaactt cgctaacggg gtcgctgaat ggatcagctc taactcgcgt    3900
tcacaggctt acaaagtaac ctgtagcgtt cgtcagagct ctgcgcagaa tcgcaaatac    3960
accatcaaag tcgaggtgcc taaagtggca cccagactg ttggtggtgt agagcttcct    4020
gtagccgcat ggcgttcgta cttaaatatg gaactaacca ttccaatttt cgctacgaat    4080
tccgactgcg agcttattgt taaggcaatg caaggtctcc taaagatgg aaacccgatt    4140 ccctcagcaa tcgcagcaaa ctccggcatc tactagaact ttactcagtt cgttctcgtc    4200
gacaatggcg gtaccggcga cgtgactgtc gccccaagca acttcgctaa cggggtcgct    4260
gaatggatca gctctaactc gcgttcacag gcttacaaag taacctgtag cgttcgtcag    4320
agctctgcgc agaatcgcaa atacaccatc aaagtcgagg tgcctaaagt ggcaacccag    4380
actgttggtg gtgtagagct tcctgtagcc gcatggcgtt cgtacttaaa tatggaacta    4440
accattccaa ttttcgctac gaattccgac tgcgagctta ttgttaaggc aatgcaaggt    4500
ctcctaaaag atggaaaccc gattccctca gcaatcgcag caaactccgg catctactaa    4560
tagacgccgg gttaattaat taaggatccg gctgctaaca aagcccgaaa ggaagctgag    4620
ttggctgctg ccaccgctga gcaataacta gcataacccc ttggggcctc taaacgggtc    4680
ttgaggggtt ttttgctgaa aggaggaact atatccggat atccacagga cgggtgtggt    4740
cgccatgatc gcgtagtcga tagtggctcc aagtagcgaa gcgagcagga ctgggcggcg    4800
gccaaagcgg tcggacagtg ctccgagaac gggtgcgcat agaaattgca tcaacgcata    4860
tagcgctagc agcacgccat agtgactggc gatgctgtcg gaatggacga tatcccgcaa    4920
gaggcccggc agtaccggca taaccaagcc tatgcctaca gcatccaggg tgacggtgcc    4980
gaggatgacg atgagcgcat tgttagattt catacacggt gcctgactgc gttagcaatt    5040
```

```
taactgtgat aaactaccgc attaaagctt atcgatgata agctgtcaaa catgaa      5096
```

<210> SEQ ID NO 3
<211> LENGTH: 4486
<212> TYPE: DNA
<213> ORGANISM: Artificial Sequence
<220> FEATURE:
<223> OTHER INFORMATION: pDSP62 plasmid

<400> SEQUENCE: 3

```
ttcttagaaa aactcatcga gcatcaaatg aaactgcaat ttattcatat caggattatc      60
aataccatat ttttgaaaaa gccgtttctg taatgaagga gaaaactcac cgaggcagtt     120
ccataggatg gcaagatcct ggtatcggtc tgcgattccg actcgtccaa catcaataca     180
acctattaat ttcccctcgt caaaaataag gttatcaagt gagaaatcac catgagtgac     240
gactgaatcc ggtgagaatg gcaaaagctt atgcatttct ttccagactt gttcaacagg     300
ccagccatta cgctcgtcat caaaatcact cgcatcaacc aaaccgttat tcattcgtga     360
ttgcgcctga gcgagacgaa atacgcgatc gctgttaaaa ggacaattac aaacaggaat     420
cgaatgcaac cggcgcagga acactgccag cgcatcaaca atattttcac ctgaatcagg     480
atattcttct aatacctgga atgctgtttt cccggggatc gcagtggtga gtaaccatgc     540
atcatcagga gtacggataa aatgcttgat ggtcggaaga ggcataaatt ccgtcagcca     600
gtttagtctg accatctcat ctgtaacatc attggcaacg ctacctttgc catgtttcag     660
aaacaactct ggcgcatcgg gcttcccata caatcgatag attgtcgcac ctgattgccc     720
gacattatcg cgagcccatt tatacccata taaatcagca tccatgttgg aatttaatcg     780
cggcctcgag caagacgttt cccgttgaat atggctcata cacccccttg tattactgtt     840
tatgtaagca gacagtttta ttgttcatga ccaaaatccc ttaacgtgag ttttcgttcc     900
actgagcgtc agaccccgta gaaaagatca aaggatcttc ttgagatcct ttttttctgc     960
gcgtaatctg ctgcttgcaa acaaaaaaac caccgctacc agcggtggtt tgtttgccgg    1020
atcaagagct accaactctt tttccgaagg taactggctt cagcagagcg cagataccaa    1080
atactgtcct tctagtgtag ccgtagttag gccaccactt caagaactct gtagcaccgc    1140
ctacatacct cgctctgcta atcctgttac cagtggctgc tgccagtggc gataagtcgt    1200
gtcttaccgg gttggactca agacgatagt taccggataa ggcgcagcgg tcgggctgaa    1260
cggggggttc gtgcacacag cccagcttgg agcgaacgac ctacaccgaa ctgagatacc    1320
tacagcgtga gctatgagaa agcgccacgc ttcccgaagg gagaaaggcg gacaggtatc    1380
cggtaagcgg cagggtcgga acaggagagc gcacgaggga gcttccaggg ggaaacgcct    1440
ggtatcttta tagtcctgtc gggtttcgcc acctctgact tgagcgtcga ttttttgtgat   1500
gctcgtcagg ggggcggagc ctatggaaaa acgccagcaa cgcggccttt ttacggttcc    1560
tggccttttg ctggcctttt gctcacatgt tctttcctgc gttatcccct gattctgtgg    1620
ataaccgtat taccgccttt gagtgagctg ataccgctcg ccgcagccga acgaccgagc    1680
gcagcgagtc agtgagcgag gaagcggaag agcgcctgat gcggtatttt ctccttacgc    1740
atctgtgcgg tatttcacac cgcatatatg gtgcactctc agtacaatct gctctgatgc    1800
cgcatagtta agccagtata cactccgcta tcgctacgtg actgggtcat ggctgcgccc    1860
cgacacccgc caaacccgc tgacgcgccc tgacgggctt gtctgctccc ggcatccgct    1920
tacagacaag ctgtgaccgt ctccgggagc tgcatgtgtc agaggttttc accgtcatca    1980
```

-continued

```
ccgaaacgcg cgaggcagct gcggtaaagc tcatcagcgt ggtcgtgaag cttttcaaaa    2040
ttgtaaacgt taatattttg ttaaaattcg cgttaaattt ttgttaaatc agctcatttt    2100
ttaaccaata ggccgaaatc ggcaaaatcc cttataaatc aaaagaatag cccgagatag    2160
ggttgagtgt tgttccagtt tggaacaaga gtccactatt aaagaacgtg gactccaacg    2220
tcaaagggcg aaaaaccgtc tatcagggcg atggcccact acgtgaacca tcacccaaat    2280 caagttttg gggtcgaggt gccgtaaagc actaaatcgg aaccctaaag ggagcccccg     2340
atttagagct tgacggggaa agccggcgaa cgtggcgaga aggaaggga agaaagcgaa     2400 aggagcgggc gctagggcgc tggcaagtgt agcggtcacg ctgcgcgtaa ccaccacacc    2460
cgccgcgctt aatgcgccgc tacagggcgc gtactatggt tgctttgacg tcggccgcca    2520
tgccggcgat aatggcctgc ttctcgccga aacgtttggt ggcgggacca gtgacgaagg    2580
cttgagcgag ggcgtgcaag attccgaata ccgcaagcga caggccgatc atcgtcgcgc    2640
tccagcgaaa gcggtcctcg ccgaaaatga cccagagcgc tgccggcacc tgtcctacga    2700
gttgcatgat aaagaagaca gtcataagtg cggcgacgat agtcatgccc cgcgcccacc    2760
ggaaggagct gactgggttg aaggctctca agggcatcgg ctctccctta tgcgactcct    2820
gcattaggaa gcagcccagt agtaggttga ggccgttgag caccgccgcc gcaaggaatg    2880
gtgcatgcaa ggagatggcg cccaacagtc ccccggccac ggggcctgcc accatacccca   2940 cgccgaaaca agcgctcatg agcccgaagt ggcgagcccg atcttcccca tcggtgatgt    3000
cggcgatata ggcgccagca accgcacctg tggcgccggt gatgccggcc acgatgcgtc    3060
cggcgtagag gatcgagatc tcgatcccgc gaaattaata cgactcacta tagggagacc    3120
acaacggttt ccctctagaa ataattttgt ttaactttaa gaaggagata taccatggca    3180
agcaatttca cgcaatttgt attggtagat aacgggggta cggggatgt tacggtagca     3240 ccttcaaatt ttgcaaatgg tgtagcagag tggatatcaa gcaatagcag aagccaagca    3300
tataaggtta cgtgctcagt aagacaatca agcgctcaaa acagaaagta tacgataaag    3360
gtagaagttc cgaaggttgc tacgcaaacg gtaggtggtg ttgaattgcc ggttgcagct    3420
tggagaagct atctcaacat ggagttgacg atacctatat ttgcaaccaa cagtgattgt    3480
gaattgatag taaaagctat gcaggggttg ttgaaggacg gtaatcctat accgagcgct    3540
atagctgcta atagtggcct ctacggcaac tttactcagt tcgttctcgt cgacaatggc    3600
ggaactggcg acgtgactgt cgccccaagc aacttcgcta acggggtcgc tgaatggatc    3660
agctctaact cgcgttcaca ggcttacaaa gtaacctgta gcgttcgtca gagctctgcg    3720
cagaatcgca aatacaccat caaagtcgag gtgcctaaag tggcaaccca gactgttggt    3780
ggtgtagagc ttcctgtagc cgcatggcgt tcgtacttaa atatggaact aaccattcca    3840
attttcgcta cgaattccga ctgcgagctt attgttaagg caatgcaagg tctcctaaaa    3900
gatgaaaacc cgattccctc agcaatcgca gcaaactccg gcatctacta atagacgccg    3960
ggttaattaa ttaggatccg gctgctaaca aagcccgaaa ggaagctgag ttggctgctg    4020
ccaccgctga gcaataacta gcataacccc ttggggcctc taaacgggtc ttgaggggtt    4080
ttttgctgaa aggaggaact atatccggat atccacagga cggtgtggt cgccatgatc     4140 gcgtagtcga tagtggctcc aagtagcgaa gcgagcagga ctgggcggcg ccaaagcgg     4200 tcggacagtg ctccgagaac gggtgcgcat agaaattgca tcaacgcata tagcgctagc    4260
agcacgccat agtgactggc gatgctgtcg gaatggacga tatcccgcaa gaggcccggc    4320
agtaccggca taaccaagcc tatgcctaca gcatccaggg tgacggtgcc gaggatgacg    4380
```

-continued

| | |
|---|---|
| atgagcgcat tgttagattt catacacggt gcctgactgc gttagcaatt taactgtgat | 4440 |
| aaactaccgc attaaagctt atcgatgata agctgtcaaa catgaa | 4486 |

<210> SEQ ID NO 4
<211> LENGTH: 4486
<212> TYPE: DNA
<213> ORGANISM: Artificial Sequence
<220> FEATURE:
<223> OTHER INFORMATION: pDSP62(am) plasmid

<400> SEQUENCE: 4

| | |
|---|---|
| ttcttagaaa aactcatcga gcatcaaatg aaactgcaat ttattcatat caggattatc | 60 |
| aataccatat ttttgaaaaa gccgtttctg taatgaagga gaaaactcac cgaggcagtt | 120 |
| ccataggatg gcaagatcct ggtatcggtc tgcgattccg actcgtccaa catcaataca | 180 |
| acctattaat ttcccctcgt caaaaataag gttatcaagt gagaaatcac catgagtgac | 240 |
| gactgaatcc ggtgagaatg gcaaaagctt atgcatttct ttccagactt gttcaacagg | 300 |
| ccagccatta cgctcgtcat caaaatcact cgcatcaacc aaaccgttat tcattcgtga | 360 |
| ttgcgcctga gcgagacgaa atacgcgatc gctgttaaaa ggacaattac aaacaggaat | 420 |
| cgaatgcaac cggcgcagga cactgccag cgcatcaaca atattttcac ctgaatcagg | 480 |
| atattcttct aatacctgga atgctgtttt cccggggatc gcagtggtga gtaaccatgc | 540 |
| atcatcagga gtacggataa aatgcttgat ggtcggaaga ggcataaatt ccgtcagcca | 600 |
| gtttagtctg accatctcat ctgtaacatc attggcaacg ctacctttgc catgtttcag | 660 |
| aaacaactct ggcgcatcgg gcttcccata caatcgatag attgtcgcac ctgattgccc | 720 |
| gacattatcg cgagcccatt tatacccata taaatcagca tccatgttgg aatttaatcg | 780 |
| cggcctcgag caagacgttt cccgttgaat atggctcata caccccttg tattactgtt | 840 |
| tatgtaagca gacagttta ttgttcatga ccaaaatccc ttaacgtgag ttttcgttcc | 900 |
| actgagcgtc agaccccgta gaaaagatca aggatcttc ttgagatcct ttttttctgc | 960 |
| gcgtaatctg ctgcttgcaa acaaaaaaac caccgctacc agcggtggtt tgtttgccgg | 1020 |
| atcaagagct accaactctt tttccgaagg taactggctt cagcagagcg cagataccaa | 1080 |
| atactgtcct tctagtgtag ccgtagttag gccaccactt caagaactct gtagcaccgc | 1140 |
| ctacatacct cgctctgcta atcctgttac cagtggctgc tgccagtggc gataagtcgt | 1200 |
| gtcttaccgg gttggactca agacgatagt taccggataa ggcgcagcgg tcgggctgaa | 1260 |
| cggggggttc gtgcacacag cccagcttgg agcgaacgac ctacaccgaa ctgagatacc | 1320 |
| tacagcgtga gctatgagaa agcgccacgc ttcccgaagg gagaaaggcg acaggtatc | 1380 |
| cggtaagcgg cagggtcgga acaggagagc gcacgaggga gcttccaggg ggaaacgcct | 1440 |
| ggtatcttta tagtcctgtc gggtttcgcc acctctgact tgagcgtcga ttttgtgat | 1500 |
| gctcgtcagg gggcggagc ctatggaaaa acgccagcaa cgcggccttt ttacggttcc | 1560 |
| tggccttttg ctggcctttt gctcacatgt tctttcctgc gttatcccct gattctgtgg | 1620 |
| ataaccgtat taccgccttt gagtgagctg ataccgctcg ccgcagccga acgaccgagc | 1680 |
| gcagcgagtc agtgagcgag gaagcggaag agcgcctgat gcggtatttt ctccttacgc | 1740 |
| atctgtgcgg tatttcacac cgcatatatg gtgcactctc agtacaatct gctctgatgc | 1800 |
| cgcatagtta agccagtata cactccgcta tcgctacgtg actgggtcat ggctgcgccc | 1860 |
| cgacacccgc caacacccgc tgacgcgccc tgacgggctt gtctgctccc ggcatccgct | 1920 |

```
tacagacaag ctgtgaccgt ctccgggagc tgcatgtgtc agaggttttc accgtcatca    1980
ccgaaacgcg cgaggcagct gcggtaaagc tcatcagcgt ggtcgtgaag cttttcaaaa    2040
ttgtaaacgt taatattttg ttaaaattcg cgttaaattt ttgttaaatc agctcatttt    2100
ttaaccaata ggccgaaatc ggcaaaatcc cttataaatc aaaagaatag cccgagatag    2160
ggttgagtgt tgttccagtt tggaacaaga gtccactatt aaagaacgtg gactccaacg    2220
tcaaagggcg aaaaccgtc tatcagggcg atggcccact acgtgaacca tcacccaaat    2280
caagttttg gggtcgaggt gccgtaaagc actaaatcgg aaccctaaag ggagcccccg    2340
atttagagct tgacggggaa agccggcgaa cgtggcgaga aaggaaggga agaaagcgaa    2400
aggagcgggc gctagggcgc tggcaagtgt agcggtcacg ctgcgcgtaa ccaccacacc    2460
cgccgcgctt aatgcgccgc tacagggcgc gtactatggt tgctttgacg tcggccgcca    2520
tgccggcgat aatggcctgc ttctcgccga aacgtttggt ggcgggacca gtgacgaagg    2580
cttgagcgag ggcgtgcaag attccgaata ccgcaagcga caggccgatc atcgtcgcgc    2640
tccagcgaaa gcggtcctcg ccgaaaatga cccagagcgc tgccggcacc tgtcctacga    2700
gttgcatgat aaagaagaca gtcataagtg cggcgacgat agtcatgccc cgcgcccacc    2760
ggaaggagct gactgggttg aaggctctca agggcatcgg ctctcccta tgcgactcct    2820
gcattaggaa gcagcccagt agtaggttga ggccgttgag caccgccgcc gcaaggaatg    2880
gtgcatgcaa ggagatggcg cccaacagtc ccccggccac ggggcctgcc accataccca    2940
cgccgaaaca agcgctcatg agcccgaagt ggcgagcccg atcttcccca tcggtgatgt    3000
cggcgatata ggcgccagca accgcacctg tggcgccggt gatgccggcc acgatgcgtc    3060
cggcgtagag gatcgagatc tcgatcccgc gaaattaata cgactcacta tagggagacc    3120
acaacggttt ccctctagaa ataattttgt ttaactttaa gaaggagata taccatggca    3180
agcaatttca cgcaatttgt attggtagat aacggggta cggggatgt tacggtagca    3240
ccttcaaatt ttgcaaatgg tgtagcagag tggatatcaa gcaatagcag aagccaagca    3300
tataaggtta cgtgctcagt aagacaatca agcgctcaaa acagaaagta tacgataaag    3360
gtagaagttc cgaaggttgc tacgcaaacg gtaggtggtg ttgaattgcc ggttgcagct    3420
tggagaagct atctcaacat ggagttgacg atacctatat ttgcaaccaa cagtgattgt    3480
gaattgatag taaagctat gcaggggttg ttgaaggacg gtaatcctat accgagcgct    3540
atagctgcta atagtggcct ctactagaac tttactcagt tcgttctcgt cgacaatggc    3600
ggaactggcg acgtgactgt cgccccaagc aacttcgcta acgggtcgc tgaatggatc    3660
agctctaact cgcgttcaca ggcttacaaa gtaacctgta gcgttcgtca gagctctgcg    3720
cagaatcgca aatacaccat caaagtcgag gtgcctaaag tggcaaccca gactgttggt    3780
ggtgtagagc ttcctgtagc cgcatggcgt tcgtacttaa atatggaact aaccattcca    3840
attttcgcta cgaattccga ctgcgagctt attgttaagg caatgcaagg tctcctaaaa    3900
gatgaaaacc cgattccctc agcaatcgca gcaaactccg gcatctacta atagacgccg    3960
ggttaattaa ttaggatccg gctgctaaca aagcccgaaa ggaagctgag ttggctgctg    4020
ccaccgctga gcaataacta gcataacccc ttggggcctc taaacgggtc ttgaggggtt    4080
ttttgctgaa aggaggaact atatccggat atccacagga cgggtgtggt cgccatgatc    4140
gcgtagtcga tagtggctcc aagtagcgaa gcgagcagga ctgggcggcg gccaaagcgg    4200
tcggacagtg ctccgagaac gggtgcgcat agaaattgca tcaacgcata tagcgctagc    4260
agcacgccat agtgactggc gatgctgtcg gaatggacga tatcccgcaa gaggcccggc    4320
```

| | | |
|---|---|---|
| agtaccggca taaccaagcc tatgcctaca gcatccaggg tgacggtgcc gaggatgacg | 4380 |
| atgagcgcat tgttagattt catacacggt gcctgactgc gttagcaatt taactgtgat | 4440 |
| aaactaccgc attaaagctt atcgatgata agctgtcaaa catgaa | 4486 |

<210> SEQ ID NO 5
<211> LENGTH: 8599
<212> TYPE: DNA
<213> ORGANISM: Artificial Sequence
<220> FEATURE:
<223> OTHER INFORMATION: M13CM1 (derivative of M13KO7)

<400> SEQUENCE: 5

| | | |
|---|---|---|
| aacatccaat aaatcataca ggcaaggcaa agaattagca aaattaagca ataaagcctc | 60 |
| agagcataaa gctaaatcgg ttgtaccaaa aacattatga ccctgtaata ctttttgcggg | 120 |
| agaagccttt atttcaacgc aaggataaaa attttttagaa ccctcatata ttttaaatgc | 180 |
| aatgcctgag taatgtgtag gtaaagattc aaaagggtga aaaggccgg agacagtcaa | 240 |
| atcaccatca atatgatatt caaccgttct agctgataaa ttcatgccgg agagggtagc | 300 |
| tattttttgag aggtctacaa aggctatcag gtcattgcct gagagtctgg agcaaacaag | 360 |
| agaatcgatg aacggtaatc gtaaaactag catgtcaatc atatgtaccc cggttgataa | 420 |
| tcagaaaagc cccaaaaaca ggaagattgt ataagcaaat atttaaattg taacgttaa | 480 |
| tattttgtta aaattcgcgt taaattttttg ttaaatcagc tcattttttta accaataggc | 540 |
| cgaaatcggc aaaatccctt ataaatcaaa agaatagccc gagacctgca gggggggggg | 600 |
| gggaaagcca cgttgtgtct caaaatctct gatgttacat tgcacaagat aaaaatatat | 660 |
| catcatgaac aataaaactg tctgcttaca taaacagtaa tacaaggggt gttatgagcc | 720 |
| atattcaacg ggaaacgtct tgctcgagtg ttgataccgg gaagccctgg gccaactttt | 780 |
| ggcgaaaatg agacgttgat cggcacgtaa gaggttccaa cttttcaccat aatgaaataa | 840 |
| gatcactacc gggcgtattt tttgagttat cgagattttc aggagctaag gaagctaaaa | 900 |
| tggagaaaaa aatcactgga tataccaccg ttgatatatc ccaatggcat cgtaaagaac | 960 |
| attttgaggc atttcagtca gttgctcaat gtacctataa ccagaccgtt cagctggata | 1020 |
| ttacggcctt tttaaagacc gtaaagaaaa ataagcacaa gttttatccg gcctttattc | 1080 |
| acattcttgc ccgcctgatg aatgctcatc cggaattccg tatggcaatg aaagacggtg | 1140 |
| agctggtgat atgggatagt gttcacccctt gttacaccgt tttccatgag caaactgaaa | 1200 |
| cgttttcatc gctctggagt gaataccacg acgatttccg gcagtttcta cacatatatt | 1260 |
| cgcaagatgt ggcgtgttac ggtgaaaacc tggcctattt ccctaaaggg tttattgaga | 1320 |
| atatgttttt cgtctcagcc aatccctggg tgagtttcac cagttttgat ttaaacgtgg | 1380 |
| ccaatatgga caacttcttc gcccccgttt tcaccatggg caaatattat acgcaaggcg | 1440 |
| acaaggtgct gatgccgctg gcgattcagg ttcatcatgc cgtctgtgat ggcttccatg | 1500 |
| tcggcagaat gcttaatgaa ttacaacagt actgcgatga gtggcagggc ggggcgtaat | 1560 |
| tttttttaagg cagttattgg tgcccttaaa cgcctggtgc tacgcctgaa taagtgataa | 1620 |
| taagcggatg aatggcagaa attgagctcg aatcggctgg ctggtttatt gctgataaat | 1680 |
| ctggagccgg tgagcgtggg tctcgcggta tcattgcagc actggggcca gatggtaagc | 1740 |
| cctcccgtat cgtagttatc tacacgacgg gagtcaggc aactatggat gaacgaaata | 1800 |
| gacagatcgc tgagataggt gcctcactga ttaagcattg gtaactgtca gaccaagttt | 1860 |

```
actcatatat actttagatt gatttaaaac ttcatttta atttaaaagg atctaggtga      1920
agatccttt tgataatctc atgaccaaaa tcccttaacg tgagttttcg ttccactgag      1980
cgtcagaccc cttaataaga tgatcttctt gagatcgttt tggtctgcgc gtaatctctt    2040
gctctgaaaa cgaaaaaacc gccttgcagg gcggttttc gaaggttctc tgagctacca    2100
actctttgaa ccgaggtaac tggcttggag gagcgcagtc accaaaactt gtcctttcag   2160
tttagcctta accggcgcat gacttcaaga ctaactcctc taaatcaatt accagtggct   2220
gctgccagtg gtgcttttgc atgtctttcc gggttggact caagacgata gttaccggat   2280
aaggcgcagc ggtcggactg aacgggggt tcgtgcatac agtccagctt ggagcgaact    2340
gcctacccgg aactgagtgt caggcgtgga atgagacaaa cgcggccata acagcggaat   2400
gacaccggta aaccgaaagg caggaacagg agagcgcacg agggagccgc caggggaaa    2460
cgcctggtat ctttatagtc ctgtcgggtt tcgccaccac tgatttgagc gtcagatttc   2520
gtgatgcttg tcaggggggc ggagcctatg gaaaaacggc tttgccgcgg ccctctcact   2580
tccctgttaa gtatcttcct ggcatcttcc aggaaatctc cgccccgttc gtaagccatt   2640
tccgctcgcc gcagtcgaac gaccgagcgt agcgagtcag tgagcgagga agcggaatat   2700
atcctgtatc acatattctg ctgacgcacc ggtgcagcct tttttctcct gccacatgaa   2760
gcgatccgtc ccgagatagg gttgagtgtt gttccagttt ggaacaagag tccactatta   2820
aagaacgtgg actccaacgt caaagggcga aaaccgtct atcagggcga tgccccacta    2880
cgtgaaccat cacccaaatc aagttttttg gggtcgaggt gccgtaaagc actaaatcgg   2940
aaccctaaag ggagccccg atttagagct tgacggggaa agccggcgaa cgtggcgaga   3000
aaggaaggga agaaagcgaa aggagcgggc gctagggcgc tggcaagtgt agcggtcacg   3060
ctgcgcgtaa ccaccacacc cgccgcgctt aatgcgccgc tacagggcgc gtactatggt   3120
tgctttgacg agcacgtata acgtgctttc ctcgttggaa tcagagcggg agctaaacag   3180
gaggccgatt aaagggattt tagacaggaa cggtacgcca gaatcttgag aagtgttttt   3240
ataatcagtg aggccaccga gtaaaagagt ctgtccatca cgcaaattaa ccgttgtagc   3300
aatacttctt tgattagtaa taacatcact tgcctgagta aagaactca aactatcggc    3360
cttgctggta atatccagaa caatattacc gccagccatt gcaacaggaa aaacgctcat   3420
ggaaatacct acattttgac gctcaatcgt ctgaaatgga ttatttacat tggcagattc   3480
accagtcaca cgaccagtaa taaagggac attctggcca acagagatag aacccttctg    3540
acctgaaagc gtaagaatac gtggcacaga caatattttt gaatggctat tagtcttaa    3600
tgcgcgaact gatagcccta aacatcgcc attaaaaata ccgaacgaac caccagcaga   3660
agataaaaca gaggtgaggc ggtcagtatt aacaccgcct gcaacagtgc cacgctgaga   3720
gccagcagca aatgaaaaat ctaaagcatc accttgctga acctcaaata tcaaaccctc   3780
aatcaatatc tggtcagttg gcaaatcaac agtagaaagg aattgaggaa ggttatctaa   3840
aatatcttta ggtgcactaa caactaatag attagagccg tcaatagata atacatttga   3900
ggatttagaa gtattagact ttacaaacaa ttcgacaact cgtattaaat cctttgcccg   3960
aacgttatta attttaaaag tttgagtaac attatcattt tgcggaacaa agaaaccacc   4020
agaaggagcg gaattatcat catattcctg attatcagat gatggcaatt catcaatata   4080
atcctgattg tttggattat acttctgaat tatggaagga attgaaccaa ccatatcaaa   4140
attattagca cgtaaaacag aaataaagaa attgcgtaga ttttcaggtt taacgtcaga   4200
tgaatataca gtaacagtac cttttacatc gggagaaaca ataacggatt cgcctgattg   4260
```

```
ctttgaatac caagttacaa aatcgcgcag aggcgaatta ttcatttcaa ttacctgagc    4320
aaaagaagat gatgaaacaa acatcaagaa aacaaaatta attacattta acaatttcat    4380
ttgaattacc tttttttaatg gaaacagtac ataaatcaat atatgtgagt gaataacctt   4440
```

```
ctttgaatac caagttacaa aatcgcgcag aggcgaatta ttcatttcaa ttacctgagc    4320
aaaagaagat gatgaaacaa acatcaagaa aacaaaatta attacattta acaatttcat    4380
ttgaattacc ttttttaatg gaaacagtac ataaatcaat atatgtgagt gaataacctt    4440
gcttctgtaa atcgtcgcta ttaattaatt ttcccttaga atccttgaaa acatagcgat    4500
agcttagatt aagacgctga gaagagtcaa tagtgaattt atcaaaatca taggtctgag    4560
agactacctt tttaacctcc ggcttaggtt gggttatata actatatgta aatgctgatg    4620
caaatccaat cgcaagacaa agaacgcgag aaaactttt caaatatatt ttagttaatt     4680
tcatcttctg acctaaattt aatggtttga aataccgacc gtgtgataaa taaggcgtta    4740
aataagaata acaccggaa tcataattac tagaaaaagc ctgtttagta tcatatgcgt     4800
tatacaaatt cttaccagta taaagccaac gctcaacagt agggcttaat tgagaatcgc    4860
catatttaac aacgccaaca tgtaatttag gcagaggcat tttcgagcca gtaataagag    4920
aatataaagt accgacaaaa ggtaaagtaa ttctgtccag acgacgacaa taaacaacat    4980
gttcagctaa tgcagaacgc gcctgtttat caacaataga taagtcctga caagaaaaa    5040
taatatccca tcctaattta cgagcatgta gaaaccaatc aataatcggc tgtcttttcct   5100
tatcattcca agaacgggta ttaaaccaag taccgcactc atcgagaaca agcaagccgt    5160
ttttattttc atcgtaggaa tcattaccgc gcccaatagc aagcaaatca gatatagaag    5220
gcttatccgg tattctaaga acgcgaggcg ttttagcgaa cctcccgact tgcgggaggt    5280
tttgaagcct taaatcaaga ttagttgcta ttttgcaccc agctacaatt ttatcctgaa    5340
tcttaccaac gctaacgagc gtcttttccag agcctaattt gccagttaca aaataaacag    5400
ccatattatt tatcccaatc caaataagaa acgattttttt gtttaacgtc aaaaatgaaa   5460
atagcagcct ttacagagag aataacataa aaacagggaa gcgcattaga cgggagaatt    5520
aactgaacac cctgaacaaa gtcagagggt aattgagcgc taatatcaga gagataaccc    5580
acaagaattg agttaagccc aataataaga gcaagaaaca atgaaatagc aatagctatc    5640
ttaccgaagc ccttttttaag aaaagtaagc agatagccga acaaagttac cagaaggaaa   5700
ccgaggaaac gcaataataa cggaatacccc aaaagaactg gcatgattaa gactccttat   5760
tacgcagtat gttagcaaac gtagaaaata catacataaa ggtggcaaca tataaaagaa    5820
acgcaaagac accacggaat aagtttattt tgtcacaatc aatagaaaat tcatatggtt    5880
taccagcgct aaagacaaaa gggcgacatt caaccgattg agggagggaa ggtaaatatt    5940
gacgaaaatt attcattaaa ggtgaattat caccgtcacc gacttgagcc atttgggaat    6000
tagagccagc aaaatcacca gtagcaccat taccattagc aaggccggaa acgtcaccaa    6060
tgaaaccatc gatagcagca ccgtaatcag tagcgacaga atcaagtttg cctttagcgt    6120
cagactgtag cgcgttttca tcggcatttt cggtcatagc ccccttatta gcgtttgcca    6180
tcttttcata atcaaaatca ccggaaccag agccaccacc ggaaccgcct ccctcagagc    6240
cgccaccctc agaaccgcca ccctcagagc caccaccctc agagccgcca ccagaaccac    6300
caccagagcc gccgccagca ttgacaggag gttgaggcag gtcagacgat tggccttgat    6360
attcacaaac gaatggatcc tcattaaagc cagaatggaa agcgcagtct ctgaatttac    6420
cgttccagta agcgtcatac atggcttttg atgatacagg agtgtactgg taataagttt    6480
taacggggtc agtgccttga gtaacagtgc ccgtataaac agttaatgcc ccctgcctat    6540
ttcggaacct attattctga aacatgaaag tattaagagg ctgagactcc tcaagagaag    6600
```

```
gattaggatt agcggggttt tgctcagtac caggcggata agtgccgtcg agagggttga    6660
tataagtata gcccggaata ggtgtatcac cgtactcagg aggtttagta ccgccaccct    6720
cagaaccgcc accctcagaa ccgccaccct cagagccacc accctcattt tcagggatag    6780
caagcccaat aggaacccat gtaccgtaac actgagtttc gtcaccagta caaactacaa    6840
cgcctgtagc attccacaga caaccctcat agttagcgta acgatctaaa gttttgtcgt    6900 cttttccagac gttagtaaat gaattttctg tatggggttt tgctaaacaa ctttcaacag    6960
tttcagcgga gtgagaatag aaaggaacaa ctaaaggaat tgcgaataat aattttttca    7020
cgttgaaaat ctccaaaaaa aaaggctcca aaaggagcct ttaattgtat cggtttatca    7080
gcttgctttc gaggtgaatt tcttaaacag cttgataccg atagttgcgc cgacaatgac    7140
aacaaccatc gcccacgcat aaccgatata ttcggtcgct gaggcttgca gggagttaaa    7200
ggccgctttt gcgggatcgt caccctcagc agcgaaagac agcatcggaa cgagggtagc    7260
aacggctaca gaggctttga ggactaaaga cttttttcatg aggaagtttc cattaaacgg    7320
gtaaaatacg taatgccact acgaaggcac caacctaaaa cgaaagaggc gaaagaatac    7380
actaaaacac tcatctttga cccccagcga ttataccaag cgcgaaacaa agtacaacgg    7440
agatttgtat catcgcctga taaattgtgt cgaaatccgc gacctgctcc atgttactta    7500
gccggaacga ggcgcagacg gtcaatcata agggaaccga actgaccaac tttgaaagag    7560
gacagatgaa cggtgtacag accaggcgca taggctggct gaccttcatc aagagtaatc    7620
ttgacaagaa ccggatattc attacccaaa tcaacgtaac aaagctgctc attcagtgaa    7680
taaggcttgc cctgacgaga acaccagaa cgagtagtaa attgggcttg agatggttta    7740
atttcaactt taatcattgt gaattacctt atgcgatttt aagaactggc tcattatacc    7800
agtcaggacg ttgggaagaa aaatctacgt taataaaacg aactaacgga acaacattat    7860
tacaggtaga agattcatc agttgagatt taggaatacc acattcaact aatgcagata    7920
cataacgcca aaaggaatta cgaggcatag taagagcaac actatcataa ccctcgttta    7980
ccagacgacg ataaaaacca aaatagcgag aggcttttgc aaaagaagtt ttgccagagg    8040
gggtaatagt aaaatgttta gactggatag cgtccaatac tgcggaatcg tcataaatat    8100
tcattgaatc cccctcaaat gctttaaaca gttcagaaaa cgagaatgac cataaatcaa    8160
aaatcaggtc tttaccctga ctattatagt cagaagcaaa gcggattgca tcaaaaagat    8220
taagaggaag cccgaaagac ttcaaatatc gcgttttaat tcgagcttca aagcgaacca    8280
gaccggaagc aaactccaac aggtcaggat tagagagtac ctttaattgc tccttttgat    8340
aagaggtcat ttttgcggat ggcttagagc ttaattgctg aatctggtgc tgtagctcaa    8400
catgttttaa atatgcaact aaagtacggt gtctggaagt ttcattccat gtaacagttg    8460
attcccaatt ctgcgaacga gtagatttag tttgaccatt agatacattt cgcaaatggt    8520
caataacctg tttagctata ttttcatttg gggcgcgagc tgaaaaggtg gcatcaattc    8580
tactaatagt agtagcgtt                                                 8599

<210> SEQ ID NO 6
<211> LENGTH: 5095
<212> TYPE: DNA
<213> ORGANISM: Artificial Sequence
<220> FEATURE:
<223> OTHER INFORMATION: pET2P7K32

<400> SEQUENCE: 6
ttcttagaaa aactcatcga gcatcaaatg aaactgcaat ttattcatat caggattatc    60
```

```
aataccatat ttttgaaaaa gccgtttctg taatgaagga gaaaactcac cgaggcagtt      120
ccataggatg gcaagatcct ggtatcggtc tgcgattccg actcgtccaa catcaataca      180
acctattaat ttcccctcgt caaaaataag gttatcaagt gagaaatcac catgagtgac      240
gactgaatcc ggtgagaatg gcaaaagctt atgcatttct ttccagactt gttcaacagg      300
ccagccatta cgctcgtcat caaaatcact cgcatcaacc aaaccgttat tcattcgtga      360
ttgcgcctga gcgagacgaa atacgcgatc gctgttaaaa ggacaattac aaacaggaat      420
cgaatgcaac cggcgcagga acactgccag cgcatcaaca atattttcac ctgaatcagg      480
atattcttct aatacctgga atgctgtttt cccggggatc gcagtggtga gtaaccatgc      540
atcatcagga gtacggataa aatgcttgat ggtcggaaga ggcataaatt ccgtcagcca      600
gtttagtctg accatctcat ctgtaacatc attggcaacg ctacctttgc catgtttcag      660
aaacaactct ggcgcatcgg gcttcccata caatcgatag attgtcgcac ctgattgccc      720
gacattatcg cgagcccatt tatacccata taaatcagca tccatgttgg aatttaatcg      780
cggcctcgag caagacgttt cccgttgaat atggctcata cacccccttg tattactgtt      840
tatgtaagca gacagttttta ttgttcatga ccaaaatccc ttaacgtgag ttttcgttcc      900
actgagcgtc agaccccgta gaaaagatca aaggatcttc ttgagatcct ttttttctgc      960
gcgtaatctg ctgcttgcaa acaaaaaaac caccgctacc agcggtggtt tgtttgccgg     1020
atcaagagct accaactctt tttccgaagg taactggctt cagcagagcg cagataccaa     1080
atactgtcct tctagtgtag ccgtagttag gccaccactt caagaactct gtagcaccgc     1140
ctacatacct cgctctgcta atcctgttac cagtggctgc tgccagtggc gataagtcgt     1200
gtcttaccgg gttggactca agacgatagt taccggataa ggcgcagcgg tcgggctgaa     1260
cggggggttc gtgcacacag cccagcttgg agcgaacgac ctacaccgaa ctgagatacc     1320
tacagcgtga gctatgagaa agcgccacgc ttcccgaagg gagaaaggcg gacaggtatc     1380
cggtaagcgg cagggtcgga acaggagagc gcacgaggga gcttccaggg ggaaacgcct     1440
ggtatcttta tagtcctgtc gggtttcgcc acctctgact tgagcgtcga ttttttgtgat    1500 gctcgtcagg ggggcggagc ctatggaaaa acgccagcaa cgcggccttt ttacggttcc     1560
tggccttttg ctggcctttt gctcacatgt tctttcctgc gttatcccct gattctgtgg     1620
ataaccgtat taccgccttt gagtgagctg ataccgctcg ccgcagccga acgaccgagc     1680
gcagcgagtc agtgagcgag gaagcggaag agcgcctgat gcggtatttt ctccttacgc     1740
atctgtgcgg tatttcacac cgcatatatg gtgcactctc agtacaatct gctctgatgc     1800
cgcatagtta agccagtata cactccgcta tcgctacgtg actgggtcat ggctgcgccc     1860
cgacacccgc caaacccgc tgacgcgccc tgacgggctt gtctgctccc ggcatccgct     1920
tacagacaag ctgtgaccgt ctccgggagc tgcatgtgtc agaggttttc accgtcatca     1980
ccgaaacgcg cgaggcagct gcggtaaagc tcatcagcgt ggtcgtgaag cgattcacag     2040
atgtctgcct gttcatccgc gtccagctcg ttgagtttct ccagaagcgt taatgtctgg     2100
cttctgataa agcgggccat gttaagggcg gttttttcct gtttggtcac tgatgcctcc     2160
gtgtaagggg gatttctgtt catggggta atgataccga tgaaacgaga gaggatgctc     2220
acgatacggg ttactgatga tgaacatgcc cggttactgg aacgttgtga gggtaaacaa     2280
ctggcggtat ggatgcggcg ggaccagaga aaaatcactc agggtcaatg ccagcgcttc     2340
gttaatacag atgtaggtgt tccacagggt agccagcagc atcctgcgat gcagatccgg     2400
```

-continued

```
aacataatgg tgcagggcgc tgacttccgc gtttccagac tttacgaaac acggaaaccg    2460
aagaccattc atgttgttgc tcaggtcgca gacgttttgc agcagcagtc gcttcacgtt    2520
cgctcgcgta tcggtgattc attctgctaa ccagtaaggc aaccccgcca gcctagccgg    2580
gtcctcaacg acaggagcac gatcatgcgc acccgtggcc aggacccaac gctgcccgag    2640
atgcgccgcg tgcggctgct ggagatggcg gacgcgatgg atatgttctg ccaagggttg    2700
gtttgcgcat tcacagttct ccgcaagaat tgattggctc caattcttgg agtggtgaat    2760
ccgttagcga ggtgccgccg gcttccattc aggtcgaggt ggcccggctc catgcaccgc    2820
gacgcaacgc ggggaggcag acaaggtata gggcggcgcc tacaatccat gccaacccgt    2880
tccatgtgct cgccgaggcg gcataaatcg ccgtgacgat cagcggtcca gtgatcgaag    2940
ttaggctggt aagagccgcg agcgatcctt gaagctgtcc ctgatggtcg tcatctacct    3000
gcctggacag catggcctgc aacgcgggca tcccgatgcc gccggaagcg agaagaatca    3060
taatggggaa ggccatccag cctcgcgtcg cgaacgccag caagacgtag cccagcgcgt    3120
cggccgccat gccggcgata atggcctgct tctcgccgaa acgtttggtg gcgggaccag    3180
tgacgaaggc ttgagcgagg gcgtgcaaga ttccgaatac cgcaagcgac aggccgatca    3240
tcgtcgcgct ccagcgaaag cggtcctcgc cgaaaatgac ccagagcgct gccggcacct    3300
gtcctacgag ttgcatgata aagaagacag tcataagtgc ggcgacgata gtcatgcccc    3360
gcgcccaccg gaaggagctg actgggttga aggctctcaa gggcatcggc tctcccttat    3420
gcgactcctg cattaggaag cagcccagta gtaggttgag gccgttgagc accgccgccg    3480
caaggaatgg tgcatgcaag gagatggcgc ccaacagtcc cccggccacg gggcctgcca    3540
ccatacccac gccgaaacaa gcgctcatga gcccgaagtg gcgagcccga tcttccccat    3600
cggtgatgtc ggcgatatag gcgccagcaa ccgcacctgt ggcgccggtg atgccggcca    3660
cgatgcgtcc ggcgtagagg atcgagatct cgatcccgcg aaattaatac gactcactat    3720
agggagacca caacggtttc cctctagaaa taattttgtt taactttaag aaggagatat    3780
accatggcca aaaccatcgt tctttcggtc ggcgaggcta ctcgcactct gactgagatc    3840
cagtccaccg cagaccgtca gatcttcgaa gagaaggtcg ggcctctggt gggtcggctg    3900
cgcctcacgg cttcgctccg tcaaaacgga gccaagaccg cgtatcgagt caacctaaaa    3960
ctggatcagg cggacgtcgt tgattgctcc accagcgtct cggcgagct tccgaaagtg    4020 cgctacactc aggtatggtc gcacgacgtg acaatcgttg cgaatagcac cgaggcctcg    4080
cgcaaatcgt tgtacgattt gaccaagtcc ctcgtcgcga cctcgcaggt cgaagatctt    4140
gtcgtcaacc ttgtgccgct gggccgttat ggctccaaaa ccatcgttct ttcggtcggc    4200
gagggtaccc gcactctgac tgagatccag tccaccgcag accgtcagat cttcgaagag    4260
aaggtcgggc tctggtgggt cggctgcgc ctcacggctt cgctccgtca aaacggagcc    4320
aagaccgcgt atcgagtcaa cctaaaactg gatcaggcgg acgtcgttga ttgctccacc    4380
agcgtctgcg gcgagcttcc gaaagtgcgc tacactcagg tatggtcgca cgacgtgaca    4440
atcgttgcga atagcaccga ggcctcgcgc aaatcgttgt acgatttgac caagtccctc    4500
gtcgcgacct cgcaggtcga agatcttgtc gtcaacttg tgccgctggg ccgttaaggc    4560
cctgcggtgt acccgtgtgt atggatccgg ctgctaacaa agcccgaaag gaagctgagt    4620
tggctgctgc caccgctgag caataactag cataacccct tggggcctct aaacgggtct    4680
tgaggggttt tttgctgaaa ggaggaacta tatccggata tccacaggac gggtgtggtc    4740
gccatgatcg cgtagtcgat agtggctcca agtagcgaag cgagcaggac tgggcggcgg    4800
```

-continued

| | |
|---|---|
| ccaaagcggt cggacagtgc tccgagaacg ggtgcgcata gaaattgcat caacgcatat | 4860 |
| agcgctagca gcacgccata gtgactggcg atgctgtcgg aatggacgat atcccgcaag | 4920 |
| aggcccggca gtaccggcat aaccaagcct atgcctacag catccagggt gacggtgccg | 4980 |
| aggatgacga tgagcgcatt gttagatttc atacacggtg cctgactgcg ttagcaattt | 5040 |
| aactgtgata aactaccgca ttaaagctta tcgatgataa gctgtcaaac atgaa | 5095 |

<210> SEQ ID NO 7
<211> LENGTH: 5095
<212> TYPE: DNA
<213> ORGANISM: Artificial Sequence
<220> FEATURE:
<223> OTHER INFORMATION: pET2P7K32(am)

<400> SEQUENCE: 7

| | |
|---|---|
| ttcttagaaa aactcatcga gcatcaaatg aaactgcaat ttattcatat caggattatc | 60 |
| aataccatat ttttgaaaaa gccgtttctg taatgaagga gaaaactcac cgaggcagtt | 120 |
| ccataggatg gcaagatcct ggtatcggtc tgcgattccg actcgtccaa catcaataca | 180 |
| acctattaat ttcccctcgt caaaaataag gttatcaagt gagaaatcac catgagtgac | 240 |
| gactgaatcc ggtgagaatg gcaaaagctt atgcatttct ttccagactt gttcaacagg | 300 |
| ccagccatta cgctcgtcat caaaatcact cgcatcaacc aaaccgttat tcattcgtga | 360 |
| ttgcgcctga gcgagacgaa atacgcgatc gctgttaaaa ggacaattac aaacaggaat | 420 |
| cgaatgcaac cggcgcagga acactgccag cgcatcaaca atattttcac ctgaatcagg | 480 |
| atattcttct aatacctgga atgctgtttt cccggggatc gcagtggtga gtaaccatgc | 540 |
| atcatcagga gtacggataa aatgcttgat ggtcggaaga ggcataaatt ccgtcagcca | 600 |
| gtttagtctg accatctcat ctgtaacatc attggcaacg ctacctttgc catgtttcag | 660 |
| aaacaactct ggcgcatcgg gcttcccata caatcgatag attgtcgcac ctgattgccc | 720 |
| gacattatcg cgagcccatt tatacccata taaatcagca tccatgttgg aatttaatcg | 780 |
| cggcctcgag caagacgttt cccgttgaat atggctcata acaccccttg tattactgtt | 840 |
| tatgtaagca gacagtttta ttgttcatga ccaaaatccc ttaacgtgag ttttcgttcc | 900 |
| actgagcgtc agaccccgta gaaaagatca aaggatcttc ttgagatcct ttttttctgc | 960 |
| gcgtaatctg ctgcttgcaa acaaaaaaac caccgctacc agcggtggtt tgtttgccgg | 1020 |
| atcaagagct accaactctt tttccgaagg taactggctt cagcagagcg cagataccaa | 1080 |
| atactgtcct tctagtgtag ccgtagttag gccaccactt caagaactct gtagcaccgc | 1140 |
| ctacatacct cgctctgcta atcctgttac cagtggctgc tgccagtggc gataagtcgt | 1200 |
| gtcttaccgg gttggactca agacgatagt taccggataa ggcgcagcgg tcgggctgaa | 1260 |
| cggggggttc gtgcacacag cccagcttgg agcgaacgac ctacaccgaa ctgagatacc | 1320 |
| tacagcgtga gctatgagaa agcgccacgc ttcccgaagg gagaaaggcg gacaggtatc | 1380 |
| cggtaagcgg cagggtcgga acaggagagc gcacgaggga gcttccaggg ggaaacgcct | 1440 |
| ggtatcttta tagtcctgtc gggtttcgcc acctctgact tgagcgtcga ttttttgtgat | 1500 |
| gctcgtcagg gggcggagc ctatggaaaa acgccagcaa cgcggccttt ttacggttcc | 1560 |
| tggccttttg ctggcctttt gctcacatgt tctttcctgc gttatcccct gattctgtgg | 1620 |
| ataaccgtat taccgccttt gagtgagctg ataccgctcg ccgcagccga acgaccgagc | 1680 |
| gcagcgagtc agtgagcgag gaagcggaag agcgcctgat gcggtatttt ctccttacgc | 1740 |

```
atctgtgcgg tatttcacac cgcatatatg gtgcactctc agtacaatct gctctgatgc    1800
cgcatagtta agccagtata cactccgcta tcgctacgtg actgggtcat ggctgcgccc    1860
cgacacccgc caacacccgc tgacgcgccc tgacgggctt gtctgctccc ggcatccgct    1920
tacagacaag ctgtgaccgt ctccgggagc tgcatgtgtc agaggttttc accgtcatca    1980
ccgaaacgcg cgaggcagct gcggtaaagc tcatcagcgt ggtcgtgaag cgattcacag    2040
atgtctgcct gttcatccgc gtccagctcg ttgagtttct ccagaagcgt taatgtctgg    2100
cttctgataa agcgggccat gttaagggcg ttttttcct gtttggtcac tgatgcctcc    2160
gtgtaagggg gatttctgtt catgggggta atgataccga tgaaacgaga gaggatgctc    2220
acgatacggg ttactgatga tgaacatgcc cggttactgg aacgttgtga gggtaaacaa    2280
ctggcggtat ggatgcggcg ggaccagaga aaaatcactc agggtcaatg ccagcgcttc    2340
gttaatacag atgtaggtgt tccacagggt agccagcagc atcctgcgat gcagatccgg    2400
aacataatgg tgcagggcgc tgacttccgc gtttccagac tttacgaaac acggaaaccg    2460
aagaccattc atgttgttgc tcaggtcgca gacgttttgc agcagcagtc gcttcacgtt    2520
cgctcgcgta tcggtgattc attctgctaa ccagtaaggc aaccccgcca gcctagccgg    2580
gtcctcaacg acaggagcac gatcatgcgc acccgtggcc aggacccaac gctgcccgag    2640
atgcgccgcg tgcggctgct ggagatggcg gacgcgatgg atatgttctg ccaagggttg    2700
gtttgcgcat tcacagttct ccgcaagaat tgattggctc caattcttgg agtggtgaat    2760
ccgttagcga ggtgccgccg gcttccattc aggtcgaggt ggcccggctc catgcaccgc    2820
gacgcaacgc ggggaggcag acaaggtata gggcggcgcc tacaatccat gccaacccgt    2880
tccatgtgct cgccgaggcg gcataaatcg ccgtgacgat cagcggtcca gtgatcgaag    2940
ttaggctggt aagagccgcg agcgatcctt gaagctgtcc ctgatggtcg tcatctacct    3000
gcctggacag catggcctgc aacgcgggca tcccgatgcc gccggaagcg agaagaatca    3060
taatggggaa ggccatccag cctcgcgtcg cgaacgccag caagacgtag cccagcgcgt    3120
cggccgccat gccggcgata atggcctgct tctcgccgaa acgtttggtg cgggaccag    3180
tgacgaaggc ttgagcgagg gcgtgcaaga ttccgaatac cgcaagcgac aggccgatca    3240
tcgtcgcgct ccagcgaaag cggtcctcgc cgaaaatgac ccagagcgct gccggcacct    3300
gtcctacgag ttgcatgata agaagacag tcataagtgc ggcgacgata gtcatgcccc    3360
gcgcccaccg gaaggagctg actgggttga aggctctcaa gggcatcggc tctcccttat    3420
gcgactcctg cattaggaag cagcccagta gtaggttgag gccgttgagc accgccgccg    3480
caaggaatgg tgcatgcaag gagatggcgc ccaacagtcc cccggccacg gggcctgcca    3540
ccatacccac gccgaaacaa gcgctcatga gcccgaagtg gcgagcccga tcttccccat    3600
cggtgatgtc ggcgatatag gcgccagcaa ccgcacctgt ggcgccggtg atgccggcca    3660
cgatgcgtcc ggcgtagagg atcgagatct cgatcccgcg aaattaatac gactcactat    3720
agggagacca caacggtttc cctctagaaa taattttgtt taactttaag aaggagatat    3780
accatggcca aaaccatcgt tctttcggtc ggcgaggcta ctcgcactct gactgagatc    3840
cagtccaccg cagaccgtca gatcttcgaa gagaaggtcg gcctctggt gggtcggctg    3900
cgcctcacgg cttcgctccg tcaaaacgga gccaagaccg cgtatcgagt caacctaaaa    3960
ctggatcagg cggacgtcgt tgattgctcc accagcgtct gcggcgagct tccgaaagtg    4020
cgctacactc aggtatggtc gcacgacgtg acaatcgttg cgaatagcac cgaggcctcg    4080
cgcaaatcgt tgtacgattt gaccaagtcc ctcgtcgcga cctcgcaggt cgaagatctt    4140
```

```
gtcgtcaacc ttgtgccgct gggccgttag ggctccaaaa ccatcgttct ttcggtcggc    4200
gagggtaccc gcactctgac tgagatccag tccaccgcag accgtcagat cttcgaagag    4260
aaggtcgggc ctctggtggg tcggctgcgc ctcacggctt cgctccgtca aaacggagcc    4320
aagaccgcgt atcgagtcaa cctaaaactg gatcaggcgg acgtcgttga ttgctccacc    4380
agcgtctgcg gcgagcttcc gaaagtgcgc tacactcagg tatggtcgca cgacgtgaca    4440
atcgttgcga atagcaccga ggcctcgcgc aaatcgttgt acgatttgac caagtccctc    4500
gtcgcgacct cgcaggtcga agatcttgtc gtcaaccttg tgccgctggg ccgttaaggc    4560
cctgcggtgt acccgtgtgt atggatccgg ctgctaacaa agcccgaaag gaagctgagt    4620
tggctgctgc caccgctgag caataactag cataacccct ggggcctctc aaacgggtct    4680 tgagggghttt tttgctgaaa ggaggaacta tatccggata tccacaggac gggtgtggtc    4740
gccatgatcg cgtagtcgat agtggctcca agtagcgaag cgagcaggac tgggcggcgg    4800
ccaaagcggt cggacagtgc tccgagaacg ggtgcgcata gaaattgcat caacgcatat    4860
agcgctagca gcacgccata gtgactggcg atgctgtcgg aatggacgat atcccgcaag    4920
aggcccggca gtaccggcat aaccaagcct atgcctacag catccagggt gacggtgccg    4980
aggatgacga tgagcgcatt gttagatttc atacacggtg cctgactgcg ttagcaattt    5040
aactgtgata aactaccgca ttaaagctta tcgatgataa gctgtcaaac atgaa         5095
```

<210> SEQ ID NO 8
<211> LENGTH: 4486
<212> TYPE: DNA
<213> ORGANISM: Artificial Sequence
<220> FEATURE:
<223> OTHER INFORMATION: pDSP7

<400> SEQUENCE: 8

```
ttcttagaaa aactcatcga gcatcaaatg aaactgcaat ttattcatat caggattatc      60
aataccatat ttttgaaaaa gccgtttctg taatgaagga gaaaactcac cgaggcagtt     120
ccataggatg gcaagatcct ggtatcggtc tgcgattccg actcgtccaa catcaataca     180
acctattaat ttcccctcgt caaaaataag gttatcaagt gagaaatcac catgagtgac     240
gactgaatcc ggtgagaatg gcaaaagctt atgcatttct ttccagactt gttcaacagg     300
ccagccatta cgctcgtcat caaaatcact cgcatcaacc aaaccgttat tcattcgtga     360
ttgcgcctga gcgagacgaa atacgcgatc gctgttaaaa ggacaattac aaacaggaat     420
cgaatgcaac cggcgcagga acactgccag cgcatcaaca atattttcac ctgaatcagg     480
atattcttct aatacctgga atgctgtttt cccggggatc gcagtggtga gtaaccatgc     540
atcatcagga gtacggataa aatgcttgat ggtcggaaga ggcataaatt ccgtcagcca     600
gtttagtctg accatctcat ctgtaacatc attggcaacg ctacctttgc catgtttcag     660
aaacaactct ggcgcatcgg gcttcccata caatcgatag attgtcgcac ctgattgccc     720
gacattatcg cgagcccatt tatacccata taaatcagca tccatgttgg aatttaatcg     780
cggcctcgag caagacgttt cccgttgaat atggctcata acaccccttg tattactgtt     840
tatgtaagca gacagtttta ttgttcatga ccaaaatccc ttaacgtgag ttttcgttcc     900
actgagcgtc agacccgta gaaaagatca aggatcttc ttgagatcct ttttttctgc      960
gcgtaatctg ctgcttgcaa acaaaaaaac caccgctacc agcggtggtt tgtttgccgg    1020
atcaagagct accaactctt tttccgaagg taactggctt cagcagagcg cagataccaa    1080
```

```
atactgtcct tctagtgtag ccgtagttag gccaccactt caagaactct gtagcaccgc    1140
ctacatacct cgctctgcta atcctgttac cagtggctgc tgccagtggc gataagtcgt    1200
gtcttaccgg gttggactca agacgatagt taccggataa ggcgcagcgg tcgggctgaa    1260
cggggggttc gtgcacacag cccagcttgg agcgaacgac ctacaccgaa ctgagatacc    1320
tacagcgtga gctatgagaa agcgccacgc ttcccgaagg gagaaaggcg acaggtatc     1380 cggtaagcgg cagggtcgga acaggagagc gcacgaggga gcttccaggg ggaaacgcct    1440
ggtatcttta tagtcctgtc gggtttcgcc acctctgact tgagcgtcga ttttgtgat     1500 gctcgtcagg ggggcggagc ctatggaaaa acgccagcaa cgcggccttt ttacggttcc    1560
tggccttttg ctggcctttt gctcacatgt tctttcctgc gttatcccct gattctgtgg    1620
ataaccgtat taccgccttt gagtgagctg ataccgctcg ccgcagccga acgaccgagc    1680
gcagcgagtc agtgagcgag gaagcggaag agcgcctgat gcggtatttt ctccttacgc    1740
atctgtgcgg tatttcacac cgcatatatg gtgcactctc agtacaatct gctctgatgc    1800
cgcatagtta agccagtata cactccgcta tcgctacgtg actgggtcat ggctgcgccc    1860
cgacacccgc caacacccgc tgacgcgccc tgacgggctt gtctgctccc ggcatccgct    1920
tacagacaag ctgtgaccgt ctccgggagc tgcatgtgtc agaggttttc accgtcatca    1980
ccgaaacgcg cgaggcagct gcggtaaagc tcatcagcgt ggtcgtgaag cttttcaaaa    2040
ttgtaaacgt taatattttg ttaaaattcg cgttaaattt tgttaaatc agctcatttt     2100 ttaaccaata ggccgaaatc ggcaaaatcc cttataaatc aaaagaatag cccgagatag    2160
ggttgagtgt tgttccagtt tggaacaaga gtccactatt aaagaacgtg gactccaacg    2220
tcaaagggcg aaaaaccgtc tatcagggcg atggcccact acgtgaacca tcacccaaat    2280 caagttttg gggtcgaggt gccgtaaagc actaaatcgg aaccctaaag ggagcccccg     2340
atttagagct tgacggggaa agccggcgaa cgtggcgaga aggaaggga agaaagcgaa     2400 aggagcgggc gctagggcgc tggcaagtgt agcggtcacg ctgcgcgtaa ccaccacacc    2460
cgccgcgctt aatgcgccgc tacagggcgc gtactatggt tgctttgacg tcggccgcca    2520
tgccggcgat aatggcctgc ttctcgccga aacgtttggt ggcgggacca gtgacgaagg    2580
cttgagcgag ggcgtgcaag attccgaata ccgcaagcga caggccgatc atcgtcgcgc    2640
tccagcgaaa gcggtcctcg ccgaaaatga cccagcgcgc tgccggcacc tgtcctacga    2700
gttgcatgat aaagaagaca gtcataagtg cggcgacgat agtcatgccc cgcgcccacc    2760
ggaaggagct gactggggttg aaggctctca agggcatcgg ctctccctta tgcgactcct    2820
gcattaggaa gcagcccagt agtaggttga ggccgttgag caccgccgcc gcaaggaatg    2880
gtgcatgcaa ggagatggcg cccaacagtc ccccggccac ggggcctgcc accatacccca   2940 cgccgaaaca agcgctcatg agcccgaagt ggcgagcccg atcttcccca tcggtgatgt    3000
cggcgatata ggcgccagca accgcacctg tggcgccggt gatgccggcc acgatgcgtc    3060
cggcgtagag gatcgagatc tcgatcccgc gaaattaata cgactcacta tagggagacc    3120
acaacggttt ccctctagaa ataattttgt ttaactttaa gaaggagata taccatggca    3180
aagacgatag tattgagcgt aggggaagca acgagaacgt taacgaaaat acaaagtacg    3240
gctgatagac aaatatttga ggaaaaagta ggtccgttag ttgggagatt aagattgacc    3300
gcaagcttga gacagaatgg tgcaaaaacg gcttacaggg taaatttgaa gttagaccaa    3360
gctgatgtag tagactgtag tacgtcagta tgtggggaat tgcctaaggt tagatatacg    3420
caagtttgga gccatgatgt taccatagta gctaactcaa cggaagcaag cagaaagagc    3480
```

```
ctctatgacc tcacgaaaag tttggtagct acgagccaag tagaggactt ggtagtaaat    3540
ttggttcctt taggccgtta tggctccaaa accatcgttc tttcggtcgg cgagggtacc    3600
cgcactctga ctgagatcca gtccaccgca gaccgtcaga tcttcgaaga aaggtcggg    3660 cctctggtgg gtcggctgcg cctcacggct tcgctccgtc aaaacggagc caagaccgcg    3720
tatcgagtca acctaaaact ggatcaggcg gacgtcgttg attgctccac cagcgtctgc    3780
ggcgagcttc cgaaagtgcg ctacactcag gtatggtcgc acgacgtgac aatcgttgcg    3840
aatagcaccg aggcctcgcg caaatcgttg tacgatttga ccaagtccct cgtcgcgacc    3900
tcgcaggtca aagatcttgt cgtcaacctt gtgccgctgg gccgttaagg ccctgcggtg    3960
tacccgtgtg tatggatccg gctgctaaca agcccgaaa ggaagctgag ttggctgctg    4020
ccaccgctga gcaataacta gcataacccc ttggggcctc taaacgggtc ttgaggggtt    4080
ttttgctgaa aggaggaact atatccggat atccacagga cgggtgtggt cgccatgatc    4140
gcgtagtcga tagtggctcc aagtagcgaa gcgagcagga ctgggcggcg gccaaagcgg    4200
tcggacagtg ctccgagaac gggtgcgcat agaaattgca tcaacgcata tagcgctagc    4260
agcacgccat agtgactggc gatgctgtcg gaatggacga tcccgcaa gaggcccggc    4320 agtaccggca taaccaagcc tatgcctaca gcatccaggg tgacggtgcc gaggatgacg    4380
atgagcgcat tgttagattt catacacggt gcctgactgc gttagcaatt taactgtgat    4440
aaactaccgc attaaagctt atcgatgata agctgtcaaa catgaa    4486
```

<210> SEQ ID NO 9
<211> LENGTH: 4486
<212> TYPE: DNA
<213> ORGANISM: Artificial Sequence
<220> FEATURE:
<223> OTHER INFORMATION: pDSP7(am)

<400> SEQUENCE: 9

```
ttcttagaaa aactcatcga gcatcaaatg aaactgcaat ttattcatat caggattatc      60 ataccatat ttttgaaaaa gccgtttctg taatgaagga gaaaactcac cgaggcagtt    120
ccataggatg gcaagatcct ggtatcggtc tgcgattccg actcgtccaa catcaataca    180
acctattaat ttcccctcgt caaaaataag gttatcaagt gagaaatcac catgagtgac    240
gactgaatcc ggtgagaatg gcaaaagctt atgcatttct ttccagactt gttcaacagg    300
ccagccatta cgctcgtcat caaaatcact cgcatcaacc aaaccgttat tcattcgtga    360
ttgcgcctga gcgagacgaa atacgcgatc gctgttaaaa ggacaattac aaacaggaat    420
cgaatgcaac ggcgcagga acactgccag cgcatcaaca atattttcac ctgaatcagg    480
atattcttct aatacctgga atgctgtttt cccggggatc gcagtggtga gtaaccatgc    540
atcatcagga gtacggataa aatgcttgat ggtcggaaga ggcataaatt ccgtcagcca    600
gtttagtctg accatctcat ctgtaacatc attggcaacg ctacctttgc catgtttcag    660
aaacaactct ggcgcatcgg gcttcccata caatcgatag attgtcgcac ctgattgccc    720
gacattatcg cgagcccatt tatacccata taaatcagca tccatgttgg aatttaatcg    780
cggcctcgag caagacgttt cccgttgaat atggctcata cacccccttg tattactgtt    840
tatgtaagca gacagtttta ttgttcatga ccaaaatccc ttaacgtgag ttttcgttcc    900
actgagcgtc agacccgta gaaaagatca aaggatcttc ttgagatcct ttttttctgc    960
gcgtaatctg ctgcttgcaa acaaaaaaac caccgctacc agcggtggtt tgtttgccgg    1020
```

```
atcaagagct accaactctt tttccgaagg taactggctt cagcagagcg cagataccaa    1080
atactgtcct tctagtgtag ccgtagttag gccaccactt caagaactct gtagcaccgc    1140
ctacatacct cgctctgcta atcctgttac cagtggctgc tgccagtggc gataagtcgt    1200
gtcttaccgg gttggactca agacgatagt taccggataa ggcgcagcgg tcgggctgaa    1260
cggggggttc gtgcacacag cccagcttgg agcgaacgac ctacaccgaa ctgagatacc    1320
tacagcgtga gctatgagaa agcgccacgc ttcccgaagg gagaaaggcg gacaggtatc    1380
cggtaagcgg cagggtcgga acaggagagc gcacgaggga gcttccaggg ggaaacgcct    1440
ggtatcttta tagtcctgtc gggtttcgcc acctctgact tgagcgtcga ttttgtgat     1500 gctcgtcagg ggggcggagc ctatggaaaa acgccagcaa cgcggccttt ttacggttcc    1560
tggccttttg ctggcctttt gctcacatgt tctttcctgc gttatcccct gattctgtgg    1620
ataaccgtat taccgccttt gagtgagctg ataccgctcg ccgcagccga acgaccgagc    1680
gcagcgagtc agtgagcgag gaagcggaag agcgcctgat gcggtatttt ctccttacgc    1740
atctgtgcgg tatttcacac cgcatatatg gtgcactctc agtacaatct gctctgatgc    1800
cgcatagtta agccagtata cactccgcta tcgctacgtg actgggtcat ggctgcgccc    1860
cgacacccgc caacacccgc tgacgcgccc tgacgggctt gtctgctccc ggcatccgct    1920
tacagacaag ctgtgaccgt ctccgggagc tgcatgtgtc agaggttttc accgtcatca    1980
ccgaaacgcg cgaggcagct gcggtaaagc tcatcagcgt ggtcgtgaag cttttcaaaa    2040
ttgtaaacgt taatattttg ttaaaattcg cgttaaattt tgttaaatc agctcatttt    2100 ttaaccaata ggccgaaatc ggcaaaatcc cttataaatc aaaagaatag cccgagatag    2160
ggttgagtgt tgttccagtt tggaacaaga gtccactatt aaagaacgtg gactccaacg    2220
tcaaagggcg aaaaaccgtc tatcagggcg atggcccact acgtgaacca tcacccaaat    2280 caagttttg gggtcgaggt gccgtaaagc actaaatcgg aaccctaaag ggagccccg     2340 atttagagct tgacggggaa agccggcgaa cgtggcgaga aggaaggga agaaagcgaa     2400 aggagcgggc gctagggcgc tggcaagtgt agcggtcacg ctgcgcgtaa ccaccacacc    2460
cgccgcgctt aatgcgccgc tacagggcgc gtactatggt tgctttgacg tcggccgcca    2520
tgccggcgat aatggcctgc ttctcgccga aacgtttggt ggcgggacca gtgacgaagg    2580
cttgagcgag ggcgtgcaag attccgaata ccgcaagcga caggccgatc atcgtcgcgc    2640
tccagcgaaa gcggtcctcg ccgaaaatga cccagagcgc tgccggcacc tgtcctacga    2700
gttgcatgat aaagaagaca gtcataagtg cggcgacgat agtcatgccc cgcgcccacc    2760
ggaaggagct gactgggttg aaggctctca agggcatcgg ctctccctta tgcgactcct    2820
gcattaggaa gcagcccagt agtaggttga ggccgttgag caccgccgcc gcaaggaatg    2880
gtgcatgcaa ggagatggcg cccaacagtc ccccggccac ggggcctgcc accatacccca   2940 cgccgaaaca gcgctcatg agcccgaagt ggcgagcccg atcttcccca tcggtgatgt     3000
cggcgatata ggcgccagca accgcacctg tggcgccggt gatgccggcc acgatgcgtc    3060
cggcgtagag gatcgagatc tcgatcccgc gaaattaata cgactcacta tagggagacc    3120
acaacggttt ccctctagaa ataattttgt ttaactttaa gaaggagata taccatggca    3180
aagacgatag tattgagcgt aggggaagca acgagaacgt taacggaaat acaaagtacg    3240
gctgatagac aaatatttga ggaaaaagta ggtccgttag ttgggagatt aagattgacc    3300
gcaagcttga gacagaatgg tgcaaaaacg gcttacaggg taaatttgaa gttagaccaa    3360
gctgatgtag tagactgtag tacgtcagta tgtgggggaat tgcctaaggt tagatatacg    3420
```

```
caagtttgga gccatgatgt taccatagta gctaactcaa cggaagcaag cagaaagagc    3480
ctctatgacc tcacgaaaag tttggtagct acgagccaag tagaggactt ggtagtaaat    3540
ttggttcctt taggccgtta gggctccaaa accatcgttc tttcggtcgg cgagggtacc    3600
cgcactctga ctgagatcca gtccaccgca gaccgtcaga tcttcgaaga gaaggtcggg    3660
cctctggtgg gtcggctgcg cctcacggct tcgctccgtc aaaacggagc caagaccgcg    3720
tatcgagtca acctaaaact ggatcaggcg gacgtcgttg attgctccac cagcgtctgc    3780
ggcgagcttc cgaaagtgcg ctacactcag gtatggtcgc acgacgtgac aatcgttgcg    3840
aatagcaccg aggcctcgcg caaatcgttg tacgatttga ccaagtccct cgtcgcgacc    3900
tcgcaggtcg aagatcttgt cgtcaacctt gtgccgctgg gccgttaagg ccctgcggtg    3960
tacccgtgtg tatggatccg gctgctaaca aagcccgaaa ggaagctgag ttggctgctg    4020
ccaccgctga gcaataacta gcataacccc ttggggcctc taaacgggtc ttgaggggtt    4080
ttttgctgaa aggaggaact atatccggat atccacagga cgggtgtggt cgccatgatc    4140
gcgtagtcga tagtggctcc aagtagcgaa gcgagcagga ctgggcggcg gccaaagcgg    4200
tcggacagtg ctccgagaac gggtgcgcat agaaattgca tcaacgcata tagcgctagc    4260
agcacgccat agtgactggc gatgctgtcg gaatggacga tatcccgcaa gaggcccggc    4320
agtaccggca taaccaagcc tatgcctaca gcatccaggg tgacggtgcc gaggatgacg    4380
atgagcgcat tgttagattt catacacggt gcctgactgc gttagcaatt taactgtgat    4440
aaactaccgc attaaagctt atcgatgata agctgtcaaa catgaa               4486
```

<210> SEQ ID NO 10
<211> LENGTH: 20
<212> TYPE: DNA
<213> ORGANISM: Artificial Sequence
<220> FEATURE:
<223> OTHER INFORMATION: E2 primer

<400> SEQUENCE: 10
tcagcggtgg cagcagccaa                                                20

<210> SEQ ID NO 11
<211> LENGTH: 20
<212> TYPE: DNA
<213> ORGANISM: Artificial Sequence
<220> FEATURE:
<223> OTHER INFORMATION: E3.2 primer

<400> SEQUENCE: 11
cgggctttgt tagcagccgg                                                20

<210> SEQ ID NO 12
<211> LENGTH: 20
<212> TYPE: DNA
<213> ORGANISM: Artificial Sequence
<220> FEATURE:
<223> OTHER INFORMATION: J2 primer

<400> SEQUENCE: 12
actccggcct ctacggcaac                                                20

<210> SEQ ID NO 13
<211> LENGTH: 25
<212> TYPE: DNA
<213> ORGANISM: Artificial Sequence
<220> FEATURE:

```
<223> OTHER INFORMATION: J2(amber) primer

<400> SEQUENCE: 13
actccggcat ctactagaac tttac                                         25

<210> SEQ ID NO 14
<211> LENGTH: 88
<212> TYPE: DNA
<213> ORGANISM: Artificial Sequence
<220> FEATURE:
<223> OTHER INFORMATION: synthetic tRNA gene sequence

<400> SEQUENCE: 14
gaattcgggg ctatagctca gctgggagag cgcttgcatc taaagcaaga ggtcagcggt    60
tcgatcccgc ttagctccac cactgcag                                      88

<210> SEQ ID NO 15
<211> LENGTH: 57
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 15
cgcgtcgaca atggcnnsnn snnsnnsnns nnsnnsggcg acgtgactgt cgcccca       57

<210> SEQ ID NO 16
<211> LENGTH: 17
<212> TYPE: PRT
<213> ORGANISM: Artificial Sequence
<220> FEATURE:
<223> OTHER INFORMATION: synthetic fragment

<400> SEQUENCE: 16

Gln Phe Val Leu Val Asp Asn Gly Gly Thr Gly Asp Val Thr Val Ala
1               5                   10                  15

Pro

<210> SEQ ID NO 17
<211> LENGTH: 50
<212> TYPE: DNA
```

```
<213> ORGANISM: Artificial Sequence
<220> FEATURE:
<223> OTHER INFORMATION: synthetic fragment

<400> SEQUENCE: 17
cagttcgttc tcgtcgacaa tggcggtacc ggcgacgtga ctgtcgccca            50

<210> SEQ ID NO 18
<211> LENGTH: 22
<212> TYPE: PRT
<213> ORGANISM: Artificial Sequence
<220> FEATURE:
<223> OTHER INFORMATION: synthetic fragment
<220> FEATURE:
<221> NAME/KEY: misc_feature
<222> LOCATION: (9)..(15)
<223> OTHER INFORMATION: Xaa can be any naturally occurring amino acid

<400> SEQUENCE: 18

Gln Phe Val Leu Val Asp Asn Gly Xaa Xaa Xaa Xaa Xaa Xaa Xaa Gly
1               5                   10                  15

Asp Val Thr Val Ala Pro
            20

<210> SEQ ID NO 19
<211> LENGTH: 66
<212> TYPE: DNA
<213> ORGANISM: Artificial Sequence
<220> FEATURE:
<223> OTHER INFORMATION: synthetic fragment
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 19
cagttcgttc tcgtcgacaa tggcnnsnns nnsnnsnnsn nsnnsggcga cgtgactgtc    60
gcccca                                                               66

<210> SEQ ID NO 20
<211> LENGTH: 18
<212> TYPE: PRT
<213> ORGANISM: Artificial Sequence
<220> FEATURE:
<223> OTHER INFORMATION: Wild-type PP7 coat protein N-terminal

<400> SEQUENCE: 20
```

```
Met Ala Lys Thr Ile Val Leu Ser Val Gly Glu Ala Thr Arg Thr Leu
1               5                   10                  15

Thr Glu

<210> SEQ ID NO 21
<211> LENGTH: 18
<212> TYPE: PRT
<213> ORGANISM: Artificial Sequence
<220> FEATURE:
<223> OTHER INFORMATION: pP7k mutant coat protein

<400> SEQUENCE: 21

Met Ala Lys Thr Ile Val Leu Ser Val Gly Thr Ala Thr Arg Thr Leu
1               5                   10                  15

Thr Glu

<210> SEQ ID NO 22
<211> LENGTH: 48
<212> TYPE: DNA
<213> ORGANISM: Artificial Sequence
<220> FEATURE:
<223> OTHER INFORMATION: insertion primer
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t

<400> SEQUENCE: 22
gcgggtaccn nynnynnynn ynnynnygct actcgcactc tgactgag        48

<210> SEQ ID NO 23
<211> LENGTH: 51
<212> TYPE: DNA
<213> ORGANISM: Artificial Sequence
<220> FEATURE:
<223> OTHER INFORMATION: insertion primer
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
```

```
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t

<400> SEQUENCE: 23
gcgggtaccn nynnynnynn ynnynnygag gctactcgca ctctgactga g        51

<210> SEQ ID NO 24
<211> LENGTH: 57
<212> TYPE: DNA
<213> ORGANISM: Artificial Sequence
<220> FEATURE:
<223> OTHER INFORMATION: insertion primer
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 24
gcgggtaccn nynnynnynn ynnynnynny nnygaggcta ctcgcactct gactgag   57

<210> SEQ ID NO 25
<211> LENGTH: 63
<212> TYPE: DNA
<213> ORGANISM: Artificial Sequence
<220> FEATURE:
<223> OTHER INFORMATION: insertion primer
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
```

<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t

<400> SEQUENCE: 25
gcgggtaccn nynnynnynn ynnynnynny nnynnynnyg aggctactcg cactctgact    60
gag                                                                 63

<210> SEQ ID NO 26
<211> LENGTH: 57
<212> TYPE: DNA
<213> ORGANISM: Artificial Sequence
<220> FEATURE:
<223> OTHER INFORMATION: Fp7 (Flag peptide)

<400> SEQUENCE: 26
gccggtaccg attataaaga tgatgatgat aaagaggcta ctcgcactct gactgag      57

<210> SEQ ID NO 27
<211> LENGTH: 63
<212> TYPE: DNA
<213> ORGANISM: Artificial Sequence
<220> FEATURE:
<223> OTHER INFORMATION: atxp7

<400> SEQUENCE: 27
gccggtaccg tgcatgcgag cttttttgat atcggcggcg aggctactcg cactctgact    60
gag                                                                 63

<210> SEQ ID NO 28
<211> LENGTH: 60
<212> TYPE: DNA
<213> ORGANISM: Artificial Sequence
<220> FEATURE:
<223> OTHER INFORMATION: atxp7r
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:

```
<221> NAME/KEY: misc_feature
<222> LOCATION: (34)..(35)
<223> OTHER INFORMATION: n is a, c, g, or t

<400> SEQUENCE: 28
gccggtaccn nsnnsgcgag cttttttgat nnsnnsgagg ctactcgcac tctgactgag    60

<210> SEQ ID NO 29
<211> LENGTH: 63
<212> TYPE: DNA
<213> ORGANISM: Artificial Sequence
<220> FEATURE:
<223> OTHER INFORMATION: v3p7

<400> SEQUENCE: 29
gccggtacca tccagcgcgg cccgggccgc gcgtttgtgg aggctactcg cactctgact    60
gag                                                                  63

<210> SEQ ID NO 30
<211> LENGTH: 78
<212> TYPE: DNA
<213> ORGANISM: Artificial Sequence
<220> FEATURE:
<223> OTHER INFORMATION: L2p7

<400> SEQUENCE: 30
gccggtaccc agctgtataa aacctgcaaa caggcgggca cctgcccgcc ggatgaggct    60
actcgcactc tgactgag                                                  78

<210> SEQ ID NO 31
<211> LENGTH: 57
<212> TYPE: DNA
<213> ORGANISM: Artificial Sequence
<220> FEATURE:
<223> OTHER INFORMATION: L2.5p7

<400> SEQUENCE: 31
gccggtaccc agctgtataa aacctgcaaa caggaggcta ctcgcactct gactgag       57

<210> SEQ ID NO 32
<211> LENGTH: 8
<212> TYPE: PRT
<213> ORGANISM: Artificial Sequence
<220> FEATURE:
<223> OTHER INFORMATION: Flag epitope

<400> SEQUENCE: 32

Asp Tyr Lys Asp Asp Asp Asp Lys
1               5

<210> SEQ ID NO 33
<211> LENGTH: 10
<212> TYPE: PRT
<213> ORGANISM: Artificial Sequence
<220> FEATURE:
<223> OTHER INFORMATION: HIV V3 peptide

<400> SEQUENCE: 33

Ile Gln Arg Gly Pro Gly Arg Ala Pro Val
1               5                   10

<210> SEQ ID NO 34
<211> LENGTH: 15
<212> TYPE: PRT
<213> ORGANISM: Artificial Sequence
```

```
<220> FEATURE:
<223> OTHER INFORMATION: HPV16 L2 peptide

<400> SEQUENCE: 34

Gln Leu Tyr Lys Thr Cys Lys Gln Ala Gly Tyr Cys Pro Pro Asp
1               5                   10                  15

<210> SEQ ID NO 35
<211> LENGTH: 10
<212> TYPE: PRT
<213> ORGANISM: Artificial Sequence
<220> FEATURE:
<223> OTHER INFORMATION: Anthrax Protective Antigen

<400> SEQUENCE: 35

Val His Ala Ser Phe Phe Asp Ile Gly Gly
1               5                   10

<210> SEQ ID NO 36
<211> LENGTH: 10
<212> TYPE: PRT
<213> ORGANISM: Artificial Sequence
<220> FEATURE:
<223> OTHER INFORMATION: anti-Flag M2 antibody

<400> SEQUENCE: 36

Lys Tyr Glu Tyr Lys Glu Ser Val Lys Pro
1               5                   10

<210> SEQ ID NO 37
<211> LENGTH: 10
<212> TYPE: PRT
<213> ORGANISM: Artificial Sequence
<220> FEATURE:
<223> OTHER INFORMATION: anti-Flag M2 antibody

<400> SEQUENCE: 37

Thr Asp Ser Thr Arg Tyr Lys Asp Trp Thr
1               5                   10

<210> SEQ ID NO 38
<211> LENGTH: 10
<212> TYPE: PRT
<213> ORGANISM: Artificial Sequence
<220> FEATURE:
<223> OTHER INFORMATION: anti-Flag M2 antibody

<400> SEQUENCE: 38

Gly Tyr Lys Glu His Thr Ser Tyr Lys Ser
1               5                   10

<210> SEQ ID NO 39
<211> LENGTH: 10
<212> TYPE: PRT
<213> ORGANISM: Artificial Sequence
<220> FEATURE:
<223> OTHER INFORMATION: anti-Flag M2 antibody

<400> SEQUENCE: 39

Tyr Ser Gly Tyr Lys Tyr Pro Glu Asn Gln
1               5                   10

<210> SEQ ID NO 40
<211> LENGTH: 10
<212> TYPE: PRT
<213> ORGANISM: Artificial Sequence
<220> FEATURE:
```

<223> OTHER INFORMATION: anti-Flag M2 antibody

<400> SEQUENCE: 40

Ala Asp Tyr Lys Thr Phe Glu Val Pro Ala
1               5                   10

<210> SEQ ID NO 41
<211> LENGTH: 9
<212> TYPE: PRT
<213> ORGANISM: Artificial Sequence
<220> FEATURE:
<223> OTHER INFORMATION: anti-Flag M2 antibody

<400> SEQUENCE: 41

Pro His Leu Tyr Lys Glu Ser Trp Pro
1               5

<210> SEQ ID NO 42
<211> LENGTH: 10
<212> TYPE: PRT
<213> ORGANISM: Artificial Sequence
<220> FEATURE:
<223> OTHER INFORMATION: anti-Flag M2 antibody

<400> SEQUENCE: 42

Gly Asp Tyr Thr Asp Tyr Lys Ser Asp Asp
1               5                   10

<210> SEQ ID NO 43
<211> LENGTH: 10
<212> TYPE: PRT
<213> ORGANISM: Artificial Sequence
<220> FEATURE:
<223> OTHER INFORMATION: anti-Flag M2 antibody

<400> SEQUENCE: 43

Asp Thr Phe Met Asp Tyr Lys Ser Arg Asp
1               5                   10

<210> SEQ ID NO 44
<211> LENGTH: 12
<212> TYPE: PRT
<213> ORGANISM: Artificial Sequence
<220> FEATURE:
<223> OTHER INFORMATION: anti-Flag M2 antibody

<400> SEQUENCE: 44

His Leu Leu Ser Glu Gly Asp Tyr Lys Ser Gly Asp
1               5                   10

<210> SEQ ID NO 45
<211> LENGTH: 10
<212> TYPE: PRT
<213> ORGANISM: Artificial Sequence
<220> FEATURE:
<223> OTHER INFORMATION: anti-Flag M2 antibody

<400> SEQUENCE: 45

Asp Thr Arg Asp Tyr Lys Leu Ala Asp Pro
1               5                   10

<210> SEQ ID NO 46
<211> LENGTH: 10
<212> TYPE: PRT
<213> ORGANISM: Artificial Sequence
<220> FEATURE:
<223> OTHER INFORMATION: anti-Flag M2 antibody

```
<400> SEQUENCE: 46

Leu Asp Tyr Asn Asp Tyr Lys Ser Arg Asp
1               5                   10

<210> SEQ ID NO 47
<211> LENGTH: 10
<212> TYPE: PRT
<213> ORGANISM: Artificial Sequence
<220> FEATURE:
<223> OTHER INFORMATION: anti-Flag M2 antibody

<400> SEQUENCE: 47

Gly Asp Tyr Thr Asp Tyr Lys Ser Asp Asp
1               5                   10

<210> SEQ ID NO 48
<211> LENGTH: 9
<212> TYPE: PRT
<213> ORGANISM: Artificial Sequence
<220> FEATURE:
<223> OTHER INFORMATION: anti-Flag M2 antibody

<400> SEQUENCE: 48

Asp Tyr Lys Asp Asp Asp Asp Lys Leu
1               5
```

US 9,365,831 B2

PLASMIDS AND METHODS FOR PEPTIDE DISPLAY AND AFFINITY-SELECTION ON VIRUS-LIKE PARTICLES OF RNA BACTERIOPHAGES

RELATED APPLICATIONS AND GRANT SUPPORT

This application is a United States national phase application of and claims priority from International Patent Application No. PCT/US2010/062638 filed Dec. 31, 2010, entitled "Plasmids and Methods for Peptide Display and Affinity-Selection on Virus-Like Particles of RNA Bacteriophages", which claims the benefit of priority from U.S. Provisional Patent Application 61/335,122 filed Dec. 31, 2009, entitled "Control of Peptide Display Valency on VLPs", U.S. Provisional Application 61/335,120, filed Dec. 31, 2009, entitled "Plasmid Vectors for Facile Construction of Random Sequence Peptide Libraries on Bacteriophage MS2 VLPs and Related Constructs, Libraries, and Methods", and U.S. Provisional Application 61/335,121, filed Dec. 31, 2009, entitled "Peptide Display on Virus-Like Particles of Bacteriophage PP7", the contents of each application being incorporated herein by reference in their entirety.

This patent application was supported by Grant Nos. GM042901 and R01 AI065240 from the National Institutes of Health. The U.S. Government has certain rights in the invention.

FIELD OF THE INVENTION

The present invention relates to a system and method for display of peptides on virus-like particles (VLPs) of RNA bacteriophages, especially MS2 and PP7. Methods and plasmid vectors are described that facilitate the construction of high complexity random sequence and antigen frament libraries, from which peptides with desired binding functions may be isolated by affinity selection. Since the density of peptide display is an important determining factor in the stringency of affinity selection, a method and plasmids are also described for controlling peptide display valency on the VLPs. The inventive method allows facile adjustment of display valency levels on VLPs, especially MS2 VLPs over a wide range (i.e., from fewer than one on average to as many as ninety per particle), thus facilitating the identification and production of immunogens and vaccines, including VLPs exhibiting low valency. Although this system has been developed primarily with a view to vaccine discovery, it is has utility in a variety of other applications, including the identification of peptide-VLPs with utility for cell or tissue type-specific targeted delivery of drugs and imaging agents, and in the templated synthesis of novel materials.

This application describes methods and plasmid vectors that facilitate implementation of the VLP display system. The invention provides nucleic acid constructs useful in the expression of virus-like particles comprised of a coat polypeptides of MS2 or of PP7, each modified by insertion of a heterologous peptide, wherein the heterologous peptide is displayed on the virus-like particle and encapsidates the specific RNA (either MS2 or PP7) that directs the synthesis of the VLP and of the peptide displayed upon it. Related virus-like particles, methods, and immunogenic compositions are also provided.

BACKGROUND OF THE INVENTION

VLPs as Vaccines.

The growth of recombinant DNA technology in recent years has led to the introduction of vaccines in which an immunogenic protein has been identified, cloned and expressed in a suitable host to obtain sufficient quantities of protein to allow effective protective immunization in both animals and humans. Many of the most effective vaccines are based on the potent ability of virion surfaces to elicit neutralizing antibodies. These include licensed killed or attenuated virus vaccines, such as polio, influenza and rabies, which effectively induce protective antibody responses. More recently, subunit vaccines based upon self-assemblages of the structural proteins of human papillomavirus (HPV) and hepatitis B virus (HBV) have been approved by the Food and Drug Administration. The subunits are expressed in a suitable host and then self-assemble into particles that structurally resemble authentic viruses, but are noninfectious because they lack the viral genome. These so-called virus-like particles (VLPs) in general are highly immunogenic, because the structural proteins of which they are comprised are present in multiple copies in each individual particle. This high density of antigen presentation makes these particles especially effective at provoking a robust antibody response. The HBV and HPV vaccines are based on VLPs assembled from the structural proteins of the respective viruses themselves, but VLPs can also be utilized as scaffolds for the high-density display of heterologous epitopes. Since VLPs in general represent highly repetitive and, therefore, highly immunogenic structures, they may be derived from any number of different virus types. The present method is directed toward utilizing the VLPs of RNA bacteriophages (especially MS2 and PP7) both for immunogenic display and for epitope discovery by a method analogous to phage display [1, 2].

RNA Bacteriophages.

The single-strand RNA bacteriophages are a group of viruses found widely distributed in nature. Several have been characterized in great detail in terms of genome sequence, molecular biology, and capsid structure and assembly. MS2 is perhaps the best-studied member of the group and has been the focus of most of the work performed in the inventors's laboratories, although recent work also exploits a related phage called PP7. MS2 has a 3569-nucleotide single-strand RNA genome that encodes only four proteins: maturase, coat, lysis and replicase. The viral particle is comprised of 180 coat polypeptides, one molecule of maturase, and one copy of the RNA genome. Since the coat protein itself is entirely responsible for formation of the icosahedral shell, the MS2 VLP can be produced from plasmids as the product of a single gene. Thus, in comparison to the other phages used for peptide display, RNA VLPs are strikingly simple. The engineering of MS2 and PP7 VLPs for peptide display and affinity selection has been presented recently by these inventors [1, 2] and is also described later in this document.

Epitope Identification by Conventional Phage Display.

Phage display is one of several technologies that make possible the presentation of large libraries of random amino acid sequences with the purpose of selecting from them peptides with certain specific functions (e.g. the ability to bind a specific antibody). The most commonly used phage display method is based on the filamentous phages (e.g. M13). The basic idea is to create recombinant bacteriophage genomes containing a library of randomized sequences genetically fused in the phage's DNA genome to one of the viral structural proteins. When such recombinants are transfected into bacteria, each produces a virus particle that displays a particular peptide on its surface and packages the same recombinant genome that encodes the peptide. This establishes the linkage of genotype and phenotype essential to the method. Arbitrary functions (e.g. the binding of a receptor, immunogenicity) can be selected from complex libraries of peptide-displaying phages by the use of affinity-selection followed by amplification of the selectants by growth in E. coli. In a vast library of peptide-displaying phages, the tiny minority able to bind a particular receptor (e.g. a monoclonal antibody) can be affinity purified and then amplified by propagation in E. coli. Usually several iterative rounds of selection and amplification are sufficient to yield a relatively simple population from which individual phages displaying peptides with the desired activity can be cloned and then characterized. When the selecting molecule is an antibody, the peptides thus identified represent epitopes recognized by the antibody, and, under appropriate conditions, may be able to evoke in an immunized patient or animal an antibody response specific for the epitope in its native antigen.

However, there are disadvantages to filamentous phage display. Most importantly, a quirk of filamentous phage molecular biology often makes it difficult or impossible to display peptides at the high densities necessary for really potent immunogenicity. This means that although peptide epitopes may be identified by affinity selection, to be useful as immunogens (i.e. vaccines) they must usually be synthesized chemically and then conjugated to a more immunogenic carrier. Unfortunately, the peptide frequently loses activity when thus divorced from the structural context in which it resided during its affinity selection and optimization. The RNA phage VLP display system described here, on the other hand, creates the ability to conduct affinity selection and immungenic epitope presentation on a single platform. This is a consequence of combining high-density peptide epitope display with an affinity-selection capability, and means that the structural constraints present during the epitope's affinity selection can be maintained during the immunization process, increasing the likelihood that the epitope will retain the structure necessary to elicit the desired antibody response.

Overview of the RNA Phage VLP Display Method.

The inventors previously described a technology for peptide display and affinity selection based on the VLPs of RNA bacteriophages, including MS2 and PP7 [1, 2], and explain it briefly here. Development of the VLP display method required that two preconditions be satisfied: First it was necessary to identify a form of the RNA phage coat protein, and a site within it that tolerated insertion of foreign peptides without disruption of its ability to properly fold and assemble into a VLP. The AB-loop on the surface of coat protein was chosen as the site for peptide insertion. Peptides inserted here are prominently displayed on the surface of the VLP. Unfortunately, the wild-type form of coat protein is highly intolerant of peptide insertions in the AB-loop, with the vast majority (usually >98%) leading to folding failures. Coat protein normally folds as a dimer, ninety of which assemble into the icosahedral VLP. The inventors engineered a novel form of coat protein to stabilize it and to render it more tolerant of AB-loop insertions. To do so they took advantage of the proximity of the N- and C-termini of the two identical polypeptide chains in the dimer (FIG. 1). By duplicating the coat protein coding sequence and then fusing the two copies into a single reading frame, the inventors produced a so-called single-chain dimer. This form of the protein is dramatically more stable thermodynamically and its folding is vastly more tolerant of peptides inserted into the AB-loop of the downstream copy of the single-chain dimer [1, 2]. The resulting VLPs display one peptide per dimer, or ninety peptides per VLP. The second precondition for a peptide display/affinity-selection capability is the linkage of phenotype to genotype, as it is essential to provide a means to amplify affinity-selected sequences. This requirement was satisfied when the inventors showed that RNA phage VLPs encapsidate the messenger-RNA that directs their synthesis [1, 2]. This means that the sequences of affinity-selected peptide-VLPs can be amplified by reverse transcription and polymerase chain reaction. When the selection target is a monclonal antibody, the resulting affinity selected VLPs represent vaccine candidates for eliciting in animals or patients of antibodies whose activities mimic that of the selecting antibody.

Considerations Related to Peptide Display Valency and its Control.

This application describes plasmid vectors that facilitate the construction of complex random sequence and antigen fragment libraries on RNA phage VLPs and the affinity selection from such libraries of peptides that bind specific monoclonal antibodies (or other arbitrary receptors). Note that as originally described, the RNA phage VLP display technology presents 90 peptides on each VLP since the peptide is inserted in one AB-loop of a single-chain dimer, and 90 dimers make up the VLP [1, 2]. The multivalency of these particles is desirable for most applications of the MS2 VLP. For example, the high immunogenicity of the particle is related to the high density of the peptides displayed, and is thus a valued property in a vaccine. However, during the affinity selection process, multivalency makes it difficult to distinguish particles that display peptides with intrinsic high binding affinity for the selection target from those that bind tightly only because of multiple simultaneous weak interactions. This "avidity vs. affinity" dilemma is a well-documented complication in the selection of high affinity peptide ligands using filamentous phage display [3-5]. The present invention addresses this issue in the VLP display system by introducing a means of adjusting average peptide display valency levels over a wide range, i.e., from fewer than one to as many as ninety per particle. This makes it possible to alter the density of peptide display during the affinity-selection process. Selection is conducted in several rounds, with the first round typically conducted using multivalent display, thus obtaining a relatively complex population including all peptides having some minimal affinity for the target. In subsequent rounds the peptide display valency can be reduced, thus increasing the selection stringency, and resulting in the isolation of peptides with higher affinity for the antibody target, and better molecular mimics of the preferred epitope.

OBJECTS OF THE INVENTION

It is an object of the invention to provide VLPs which display low valency of heterologous peptides.

It is an additional object of the invention to provide nucleic acid constructs for producing VLPs, including VLPs which display low or high valency of heterologous peptides.

It is still another object of the invention to provide nucleic acid constructs for producing VLPs, including VLPS which can control the display of low or high valency of heterologous peptides.

It is yet another object of the invention to provide nucleic acid constructs for producing VLPs which can control the display of low or high valency of heterologous peptides for purposes of identifying immunogens of high affinity and using these immunogens in therapeutic and other formulations or applications.

It is an additional object of the invention to provide methods for identifying immunogenic peptides exhibiting high affinity to a selected antibody.

It is yet another object to incorporate high affinity peptides into VLPs.

Is an additional object of the invention to provide immunogenic methods and compostions using VLPs according to the present invention.

Any one or more of these and/or other objects of the invention may be readily gleaned from the description of the invention which follows.

SUMMARY OF THE INVENTION

The present invention relates to compositions, structures (including plasmids), systems and methods that facilitate the construction of high complexity random sequence and antigen fragment peptide libraries and that allow for controlling the valency (i.e. the density) of peptide display on MS2 VLPs in order to provide a more effective means of identifying and providing VLPs that incorporate selectively immunogenic peptides. The present invention represents an extension of the methods, compositions, particles, units and other disclosures which are otherwise disclosed in US patent publication no. US2009/0054246 and application no. PCT/US2007/018614 (published as WO08/024427), the entire contents of which are incorporated by reference herein, and which were briefly described above and in [1, 2, 6, 7].

The present invention provides that selection of peptides having the highest affinity for a given monoclonal antibody will provide the best molecular mimics of the native antigen, and that these peptides are the most likely to provide or induce a relevant antibody response. These peptides are proposed as being particularly appropriate for inducing immunogenicity in a patient and providing a protective response. Vaccines that are prepared from and/or incorporate these peptides are more effective, with reduced side effects especially including vaccines according to the present invention which are administered in the absence of an adjuvant.

Plasmid vectors are described that facilitate the construction of random sequence or antigen fragment peptide libraries on VLPs of RNA phage MS2 (pDSP1 and pDSP62) and on VLPs derived from RNA phage PP7 (pET2P7K32 and pDSP7). These vectors make possible the creation of libraries having in excess of $10^{11}$ to $10^{12}$ individual members. However, these vectors produce VLPs that uniformly display foreign peptides at high density (i.e. 90 per VLP). As explained above, this is a distinct advantage for vaccine applications because it confers a high level of immunogenicity to the peptide, but it often presents a problem during affinity selection because multivalency lowers the stringency of selection and makes it hard to select preferentially the tightest binding species in a population.

The present invention represents a simple solution to the problem of peptide display valency control, a system that allows the production of large amounts of wild-type and low quantities of single-chain (preferably, a dimer) coat protein containing a heterologous peptide of at least four (4) amino acids in length from a single RNA. This approach involves constructing plasmids like pDSP1(am), pDSP62(am), pET2P7K32(am) and pDSP7(am). These are simple variants of the plasmids described above, which were modified to contain a stop codon (preferably an amber stop codon), for example, in place of the codon (alanine) which normally encodes the first amino acid of the downstream copy of the coating protein in the single-chain dimer. Since these plasmids have a stop codon at the junction of the two halves of the single-chain dimer (see for example, pDSP1), they normally produce only the unit-length, wild-type coat protein, which of course assembles into a VLP. However, in the present approach, the plasmid or a second plasmid (e.g. pNMsupA) is modified to have inserted a tRNA gene [8, 9], such as an alanine-inserting suppressor tRNA gene which is expressed under control of a promoter (e.g. lac promoter on a chloramphenicol resistant plasmid from a different incompatability group), such that the suppressor tRNA is produced in amounts that cause a small percentage of ribosomes translating the coat sequence to read through the stop codon and produce the single-chain dimer, which includes the heterologous peptide. The resulting protein, with a guest heterologous peptide preferably inserted, for example, into its second AB-loop or at the carboxy terminus or other position within the downstream subunit, co-assembles with wild-type protein expressed from the same mRNA to form mosaic VLPs, which exhibit low valency.

According to the present method, VLPs can be produced in a controlled fashion to present fewer than one and as many as ninety (90) heterologous peptides per VLP, preferably about one to about ten (10) heterologous peptides per VLP, more preferably about 1 to about 5 heterologous peptides per VLP, more preferably about 1 to about 3 heterologous peptides per VLP, and most preferably about 2 to about 4 heterologous peptides per VLP. The reduction in peptide density according to the present invention results in VLPs with increased stringency of affinity-selection, allowing the ready identification of high-affinity peptides, which become strongly immunogenic when later returned to a high display density format. Agarose gel electrophoresis and northern blots verify that the particles produced according to the present invention encapsidate the relevant RNA. The method of the present invention further provides that the valency (number of peptides produced per VLP) can be adjusted over a wide range by controlling the expression level of the suppressor tRNA, for example, by adjusting the level of suppressor tRNA synthesis, which may be accomplished accordingly, for example, by expressing the tRNA from a promoter (e.g. proB or other appropriate promoter) whose activity can be modulated as a function of inducer concentration. Valency levels can also be controlled through the utilization of different suppressor tRNAs, or mutants thereof, with greater or lesser intrinsic suppression efficiencies.

One might wonder whether valency control could be achieved more simply by co-expressing the recombinant protein together with an excess of the wild-type coat protein, thus producing mosaic capsids wherein the content of foreign peptides is reduced. Unfortunately, this approach is impractical inasmuch as reducing the valency to an appropriate level (e.g. to fewer than one to a few peptides per VLP, on average) requires that the wild-type protein is expressed in huge excess over the recombinant peptide. Such a co-expression strategy would produce an excess of irrelevant (i.e. non-foreign-peptide encoding) RNA, which, by its sheer abundance, would be packaged within the VLPs in preference to the peptide-encoding RNA. Because specific encapsidation appears to be independent of the presence of any simple packaging signal in the RNA (1), there seems to be no simple way to mark the minority peptide-encoding species for selective encapsidation. While it is imaginable that there are workable variants of this co-expression approach, these variants tend to be overly complicated. Our system solves this problem by producing both forms of the protein from a single mRNA.

By way of example, the following embodiments may be used to further exemplify the present invention. It is noted that in each of the embodiments which are included below, MS2 coat polypeptide or PP7 coat polypeptide may be used in the individual nucleic acid constructs and should not be viewed as being limited to MS2 or PP7 coat polypeptide unless such limitation is appropriate within the context of the description.

One embodiment of the present invention provides a nucleic acid construct (see pDSP1, for example) comprising:

(a) a bacterial or bacteriophage promoter (e.g. as described below in the Detailed Description of Invention section) which is operably associated with a coding sequence of bacteriophage MS2 single chain coat polypeptide dimer, wherein the coat polypeptide dimer coding sequence is modified to define a first restriction site (e.g. SalI or KpnI) positioned 5' to that portion of the sequence which defines the coat polypeptide dimer AB loop;

(b) a second restriction site (e.g. BamHI) positioned 3' to the coat polypeptide dimer coding sequence;

(c) PCR primers positioned 5' to the first restriction site and 3' to the second restriction site (a definition and listing of relevant PCR primers is given in Detailed Description of Invention).

(d) an antibiotic resistance gene (e.g. kanamycin), and (e) a replication origin for replication in a prokaryotic cell (e.g. the replication origin from the plasmid ColE1).

In another embodiment the invention provides a nucleic acid construct (for example, see pDSP62), comprising:

(a) a bacterial or bacteriophage promoter which is operably associated with a coding sequence of bacteriophage MS2 single chain coat polypeptide dimer, wherein one of the two halves of the single chain dimer sequence is modified (i.e. "codon juggled") with multiple silent nucleotide substitutions to produce a modified dimer so that mutagenic oligonucleotide primers may be annealed specifically to said modified or unmodified half of said modified dimer (preferably, a sufficient number of mutations within 20 nucleotide units on either side of the AB-loop that allow the two sequences to be distinguished by hybridization of a primer.);

(b) a first restriction site (e.g. SalI) positioned 5' to that portion of the coat sequence that specifies the AB-loop.

(c) a second restriction site (e.g. BamHI) 3' to the coat polypeptide dimer coding sequence, and (d) PCR primers positioned 5' to the first restriction site and 3' to the second restriction site (a definition and listing of relevant PCR primers is given in Detailed Description of Invention);

(e) a gene for resistance to a first antibiotic;

(f) a replication origin for replication in a prokaryotic cell;

(g) a second origin of replication from a single strand DNA bacteriophage (e.g M13 or fd); and (h) a helper single strand DNA bacteriophage (e.g., M13, fd) modified to contain a gene conferring resistance to a second antibiotic.

In another embodiment, relative to the nucleic acid constructs of the invention, the coding sequence of bacteriophage MS2 (or PP7) single chain coat polypeptide dimer further comprises a nucleic acid sequence encoding a heterologous peptide and the construct optionally comprises a transcription terminator positioned 3' to the second restriction site. Such nucleic acid constructs are useful in the expression of virus-like particles comprised of a coat polypeptide of MS2 (or PP7) modified by insertion of a heterologous peptide, wherein the heterologous peptide is displayed on the virus-like particle and encapsidates MS2 (or PP7) mRNA.

In another embodiment (for example, pET2P7K32), the nucleic acid construct comprises:

(a) a bacterial or bacteriophage promoter which is operably associated with a coding sequence of bacteriophage PP7 (or MS2) single chain coat polypeptide dimer, wherein the coat polypeptide dimer coding sequence is modified to define a first restriction site which is located in the downstream portion of the coat polypeptide dimer coding sequence and which is either positioned 5' to, or located within, the sequence which defines the coat polypeptide dimer AB loop;

(b) a second restriction site positioned 3' to the coat polypeptide dimer coding sequence;

(c) PCR primers positioned 5' to the first restriction site and 3' to the second restriction site (a definition and listing of relevant PCR primers is given in Detailed Description of Invention).

(d) an antibiotic resistance gene; and (e) a replication origin for replication in a prokaryotic cell.

In an alternative embodiment (for example, pDSP7), the nucleic acid construct comprises:

(a) a bacterial or bacteriophage promoter which is operably associated with a coding sequence of bacteriophage PP7 single chain coat polypeptide dimer, wherein one half of the single chain dimer sequence is modified (i.e. "codon juggled" with multiple silent nucleotide substitutions so that mutagenic oligonucleotide primers may be annealed specifically to one or the other half (preferably, a sufficient number of mutations within 20 nucleotide units on either side of the AB-loop that allow the two sequences to be distinguished by hybridization of a primer);

(b) a first restriction site which is located in the downstream portion of the coat polypeptide dimer coding sequence and which is either positioned 5' to, or located within, the sequence which defines the coat polypeptide dimer AB loop (c) a restriction site positioned 3' to the coat polypeptide dimer coding sequence;

(d) PCR primers 5' positioned to the first restriction site and 3' to the second restriction site (a definition and listing of relevant PCR primers is given in Detailed Description of Invention).

(e) a gene for resistance to a first antibiotic;

(f) a replication origin for replication in a prokaryotic cell;

(g) a second origin of replication from a single strand DNA bacteriophage (e.g., M13, fd);

(h) a helper single strand DNA bacteriophage (e.g., M13, fd) modified to contain a gene conferring resistance to a second antibiotic.

In another embodiment of the present invention, a nucleic acid construct comprises (a) a bacterial or bacteriophage promoter which is operably associated with a coding sequence of bacteriophage MS2 or PP7 single chain coat polypeptide dimer, wherein the coat polypeptide dimer coding sequence is modified to (1) define a first restriction site which is located in the downstream portion of the coat polypeptide dimer coding sequence and which is either positioned 5' to, or located within, the sequence which defines the coat polypeptide dimer AB loop, and (2) to contain a nucleotide sequence $(NNS)_x$, where N is any nucleotide, S is a guanosine nucleotide (G) or cytidine nucleotide (C), and x is an integer from 1 to 500;

(b) a second restriction site positioned 3' to the coat polypeptide dimer coding sequence;

(c) PCR primers positioned 5' to the first restriction site and 3' to the second restriction site;

(d) an antibiotic resistance gene; and (e) a replication origin for replication in a prokaryotic cell.

In certain embodiments of the present invention which are described herein, certain of the elements which are set forth above, as provided herein, may be optionally, but preferably included within the constructs.

In other embodiments (for example, the derivatives of the plasmids described above, called DSP1(am), pDSP62(am), pET2P7K32(am) and pDSP7(am)) control of display valency is conferred by inclusion of the following additional features:

(a) a nonsense codon (for example, an amber codon as otherwise described herein) at the junction between the upstream and downstream halves of the single chain dimer;

(b) a plasmid (for example, pNMsupA) that produces a suppressor tRNA (for example, an alanine-inserting amber-suppressor) able to partially suppress translation termination at the nonsense codon described in (a) above. This plasmid has an origin of replication from a second incompatibility group and confers resistance to a second antibiotic, thus allowing its stable maintenance in bacteria that also contain one of the coat protein-producing plasmids described above. An Overview of Library Construction and Affinity Selection of Vaccine Candidates.

The MS2 VLP system is used here as an example, but it should be understood that similar methods apply to the PP7 system also presented in this application.

1. Library construction. Random sequence libraries may be produced by either of two methods. These are described in more detail later and are illustrated in FIGS. 9b and 15. (A.) A PCR product is cloned into pDSP1 between SalI and BamHI with random sequences attached in such a way as to introduce them into the AB-loop. This method is suitable for convenient construction of relatively low complexity libraries (typically $10^7$ to $10^8$ members), but is inconvenient to scale up to higher levels. (B.) For higher complexity libraries (e.g. $10^9$ to $10^{11}$ or more) a synthetic oligonucleotide primer is annealed to a single-stranded version of pDSP62 and extended with DNA polymerase to produce a double-stranded circular molecule, which is then covalently closed by the action of DNA ligase (see FIG. 12). The recombinant DNA molecules produced by either method are introduced into an appropriate expression strain of E. coli (e.g. BL21(DE3)) and where they synthesize VLPs. The particles produced from pDSP1 or pDSP62 display foreign peptides at a density of 90 per particle (high-density).

2. Affinity Selection is conducted, for example, by subjecting the VLP library to a procedure (e.g. biopanning, or other approach to rapidly identify and separate peptides exhibiting high affinity for an antibody) in which a monoclonal antibody is adsorbed the surface of one or more wells of a multi-well plastic plate. The VLP library solution is incubated with the immobilized antibody, then unbound VLPs are washed away and discarded, and any bound VLPs are eluted, usually by lowering the solution pH. Subsequently, the eluted VLPs are thermally denatured and the RNA they contain is copied into DNA by reverse transcription using an oligonucleotide primer that anneals to the RNA near its 3'-end (well downstream of the BamHI site). The resulting cDNA is then amplified by PCR using primers that anneal specifically upstream of the first restriction site (e.g. SalI) and downstream of the second restriction site (e.g. BamHI).

3. Recloning. The PCR product obtained above is digested with the first and second restriction enzymes (e.g. SalI and BamHI) and then re-cloned in the appropriate expression vector. If the second selection round is to be conducted at low peptide valency, the PCR product will be cloned in pDSP1 (am) or pDSP62(am) and the whole selected population will be introduced into an E coli expression strain containing pNMsupA (see FIG. 7). The VLPs thus produced will, on average, display only a few copies of their foreign peptides (i.e. low valency), and, because they have been once affinity-selected, will present a much simpler population of peptides than was present in the initial library.

4. Additional iterative rounds of affinity-selection and re-cloning are conducted as described above. Two to four rounds or preferably, three or four rounds (one or two at high-valency followed by one or two at low valency) are typically sufficient to produce a simple population of VLPs displaying peptides that tightly bind the selecting monoclonal antibody. When selection is deemed complete, the sequences are cloned again in pDSP1 or pDSP62, where the peptides are again displayed at high density (up to 90 peptides per capsid) for maximal immunogenicity. Individual clones are obtained and a subjected to characterization by DNA sequence analysis. Their affinity in vitro for the selecting antibody is assessed and their ability to elicit a desired antibody response is determined. In demonstration experiments employing well-characterized monoclonal antibody targets, the inventors have recovered peptides whose sequences mimic those of the previously identified epitopes. Animals immunized with the resulting VLPs produce antibodies that recognize the epitope of the original antigen.

The details of the plasmids and other aspects of the invention are described further in the following Detailed Description of the Invention.

Any one or more of the above embodiments and/or other embodiments according to the present invention may be further readily gleaned from a description of the invention which follows.

pDSP1 produces VLPs containing only the coat protein single-chain dimer.

pDSP1-Flag produces VLPs containing only a single-chain dimer with the Flag epitope inserted in its second AB-loop.

pDSP1(am) has a nonsense mutation at the junction of coat sequences in the single-chain dimer, causing it to produce large amounts of wild-type coat protein and, in the presence of the suppressor-tRNA (provided from pNMsupA), small quantities of single chain dimer. Since nonsense suppression has a low efficiency in this case, only a small fraction of ribosomes reads through the stop codon to produce the single-chain dimer. The two forms of coat protein co-assemble into a mosaic, or hybrid VLP consisting mostly of wild-type coat protein, and of small amounts of single-chain dimer (estimated at about 3% the level of wild-type coat protein).

pDSP1(am)-Flag is just Like pDSP1(am), but with the flag epitope inserted at the second AB-loop of the single chain dimer. It produces mostly wild-type coat protein, and a small amount of the single-chain dimer with the flag peptide inserted in its AB-loop.

The two arrows to the right of the image indicate the positions of the two proteins produced by suppression of the stop codons of pDSP1(am) and pDSP1(am)-Flag.

Figure 9A:
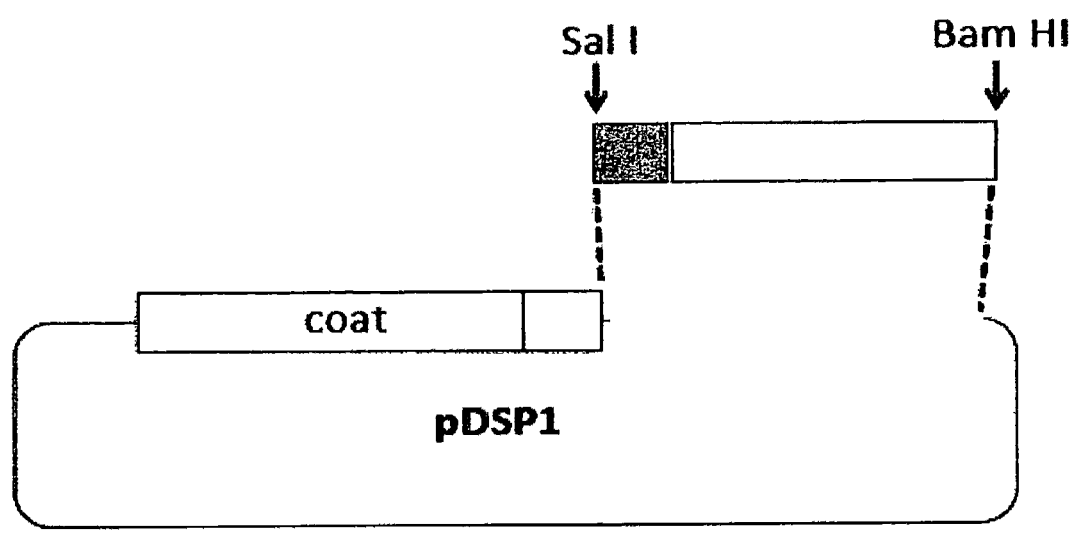
Figure 9B:
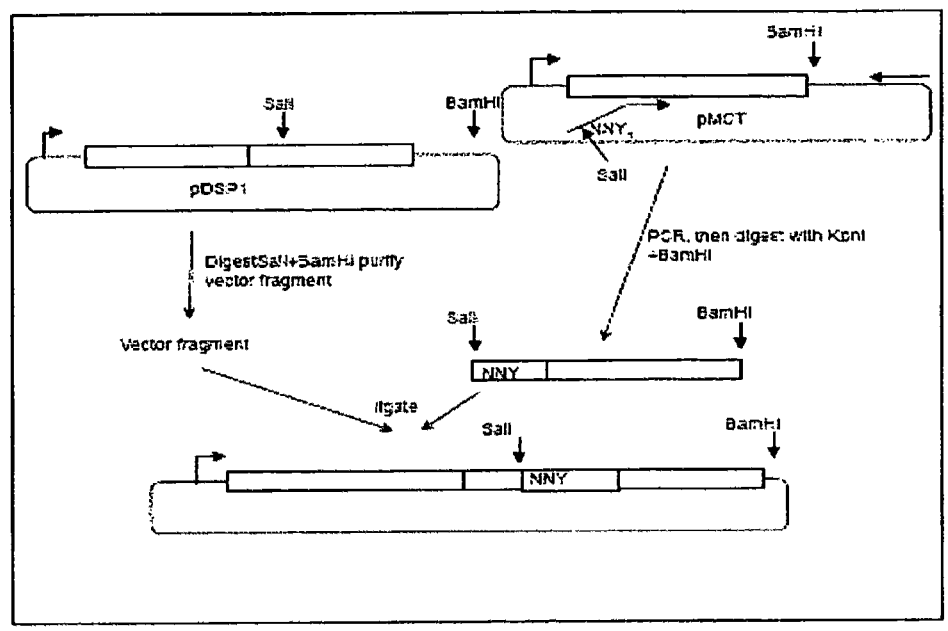

FIGS. 9a and 9b depict the pDSP1 plasmid (9a) and a technique (9b) for inserting a nucleic acid sequence encoding a heterologous peptide into that plasmid.

Figure 10:
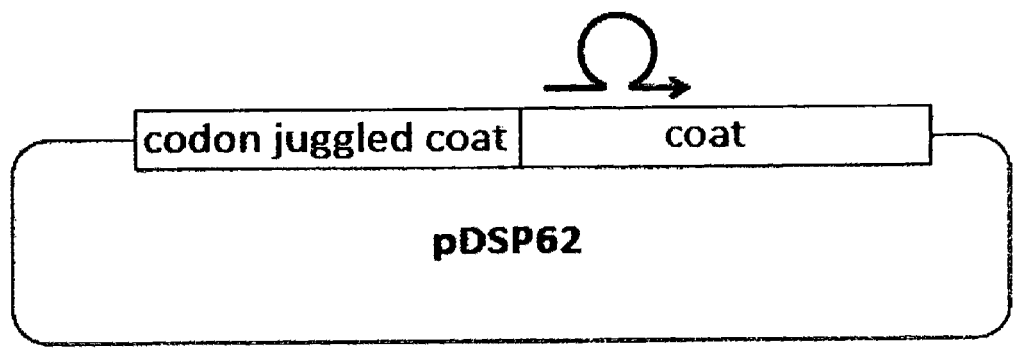

FIG. 10 depicts the pDSP62 plasmid and schematically shows how a synthetic oligonucleotide primer can be designed for insertion of sequences specifically into the AB-loop of the downstream copy of the single-chain dimer. The oligonucleotide is designed to anneal perfectly to the coat sequences flanking the AB-loop, and inserts a foreign sequence between then.

FIG. 11a contains the nucleic acid sequence for the pDSP1 plasmid (SEQ ID NO: 1) FIG. 11b shows the nucleic acid sequence of pDSP1(am) (SEQ ID NO: 2); FIG. 11c shows the nucleic acid sequence for the pDSP62 plasmid (SEQ ID NO: 3). and FIG. 11d gives the nucleic acid sequence of pDSP62 (am) (SEQ ID NO: 4). Note that the pDSP1(am) and pDSP62 (am) plasmid sequences differ from pDSP1 and pDSP62 only by nucleotide substitutions that introduce an amber codon. FIG. 11e is the nucleic acid sequence of M13CM1, a chloramphenicol resistant derivative of M13K07 (SEQ ID NO: 5.)

Figure 12:
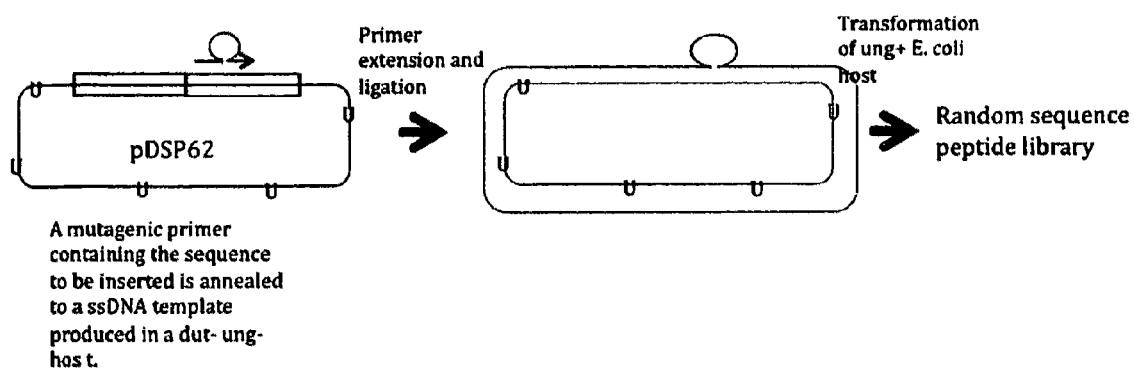

FIG. 12 depicts a method for utilizing pDSP62 and M13CM1 to produce random peptide sequence libraries. M13CM1 is a helper virus that allows pDSP62 to replicate from its M13 origin. Therefore, infection by M13CM1 of *E. coli* cells containing pDSP62 allows the production of single-stranded circular pDSP62. When grown in a dut-, ung- bacterial strain the DNA becomes substituted with dUTP in place of some of the dTTP normally present in DNA. The site-directed insertion of peptide-encoding sequences is accomplished by extension of a synthetic oligonucleotide with DNA polymerase, and the circle is closed by the action of DNA ligase. The resulting covalently closed circular DNA is introduced by electroporation into a dut+, ung+ strain of *E. coli*, where the dUTP substituted strand is degraded, resulting in a high frequency (typically 85-90%) incorporation of the insertions [10].

Figure 13A:
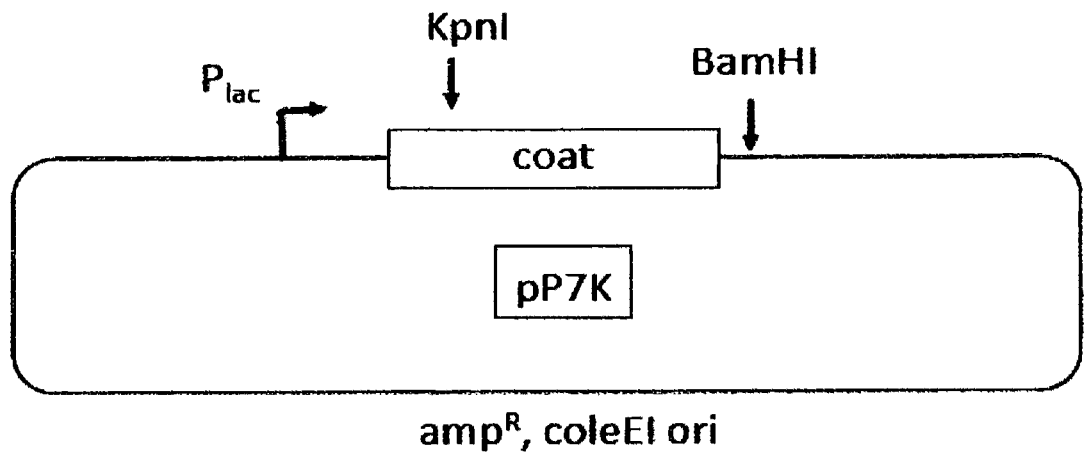
Figure 13B:
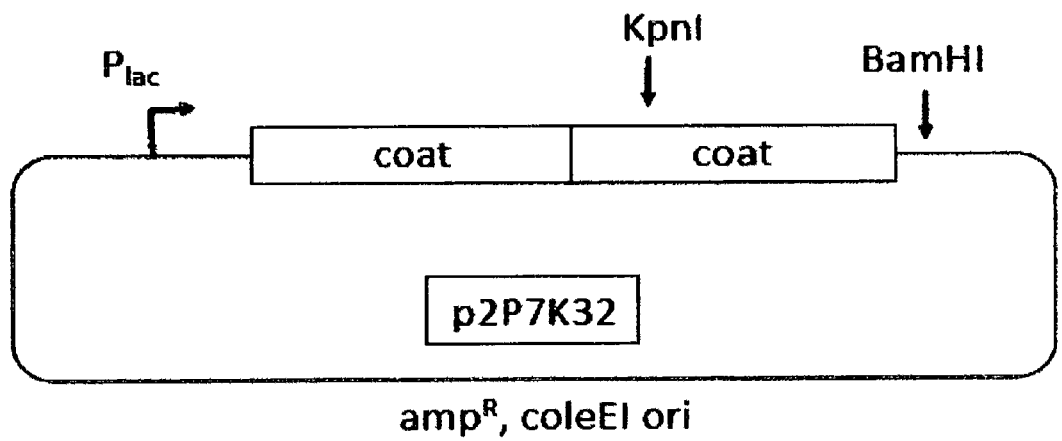

FIGS. 13a and 13b depict the pP7K (13a) and p2P7K32 (13b) plasmids. These plasmids were utilized during the development of the PP7 VLP platform simply for testing the insertion tolerance of the PP7 coat protein AB-loop by translational repression and VLP assembly assays (see the Examples Section). They should not be confused with pET2P7K32 or pDSP7, which are described later and are used for construction of VLP libraries for affinity-selection.

FIG. 14 provides the nucleotide and amino acid sequences near PP7 coat protein AB-loop and also provides the primer sequences that were used for insertion of certain specific peptide insertions. A number of specific and random peptide sequences were inserted to test the general tolerance of the PP7 single-chain dimer to AB-loop insertions, and to determine the immunogenicity of specific inserted peptides.

Figure 15:
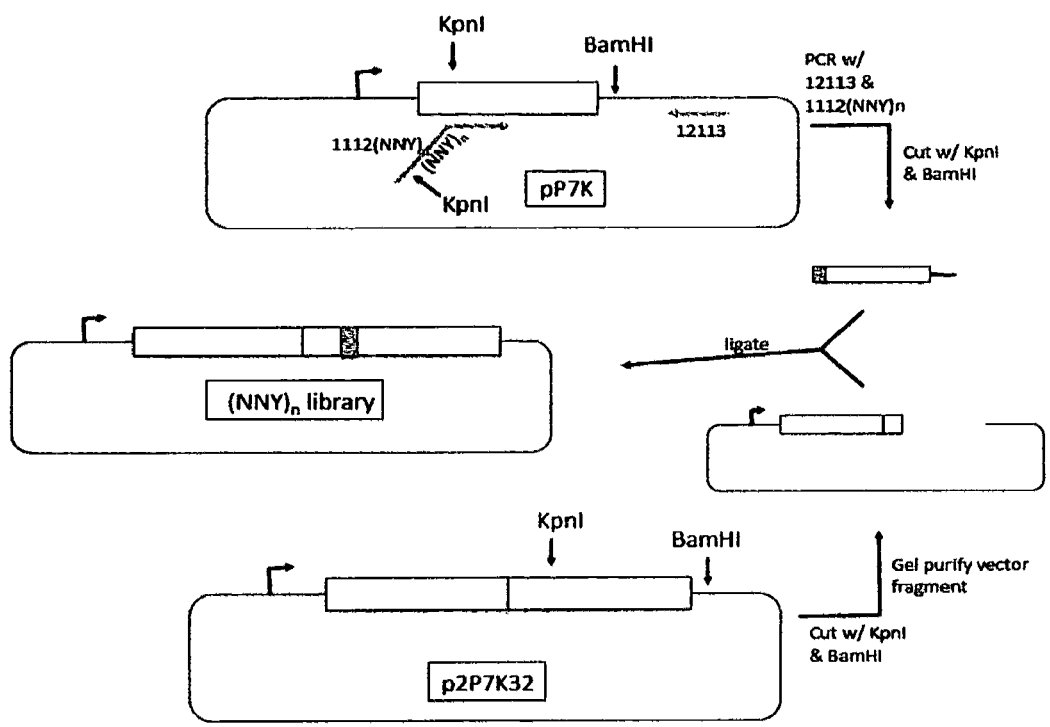

FIG. 15 illustrates the scheme used for construction of random sequence peptide libraries in p2P7K32 for the purpose of demonstrating the insertion tolerance of the PP7 single-chain coat protein's AB-loop. This method is similar to that depicted in FIG. 5b for insertion into the MS2 single-chain dimer of pDSP1.

Figure 16:
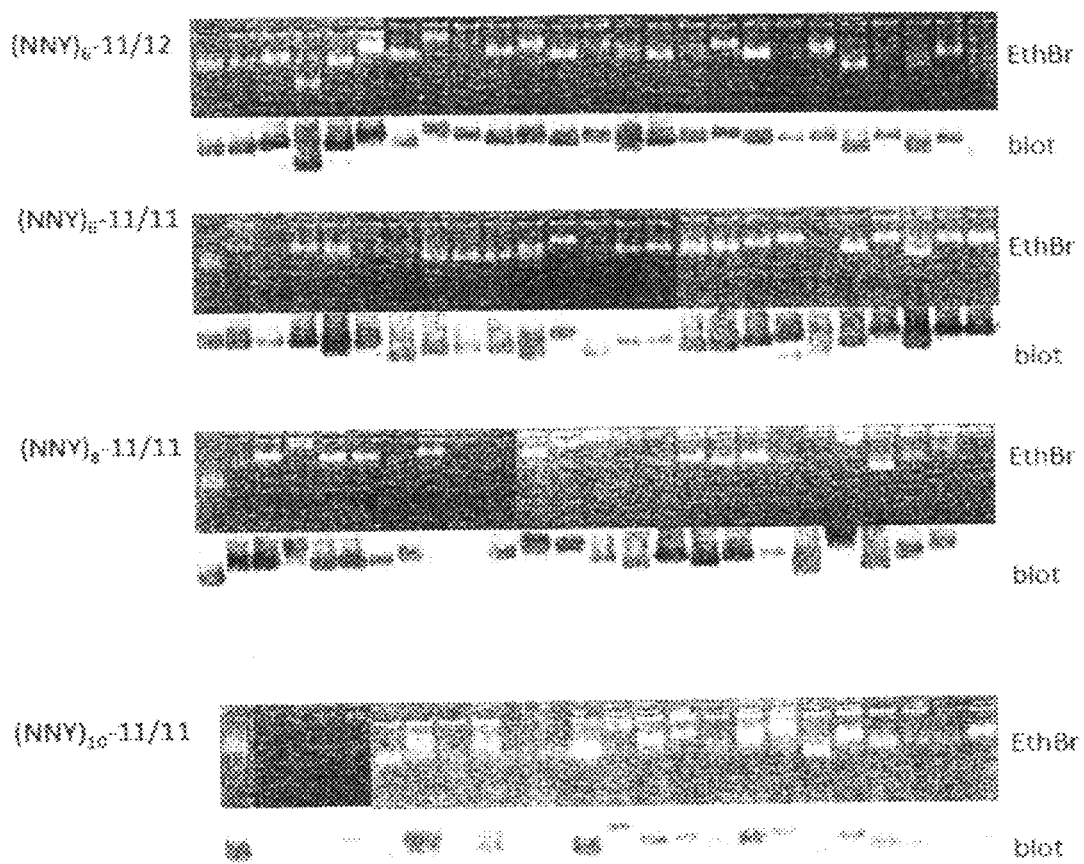

FIG. 16 provides agarose gel electrophoresis of whole cell lysates of 24 clones from each of the various libraries described herein. Nearly 100% of the clones obtained were capable of translational repression, indicating the liklihood that each protein was properly folded. To further verify that the proteins had correctly folded the ability of each to form a VLP was assessed by subjecting a. random selection of clones to electrophoresis and western blotting as shown in this figure. The top half of each set is the ethidium bromide stained gel, and the bottom half is a western blot of a duplicate gel. The left-most lane in each set is the p2P7K32 control. Each clone contains a different randomly generated peptide sequence, The fact that nearly every one produces a VLP demonstrates the high level of insertion tolerance of the PP7 coat protein single-chain dimer.

Figure 17A:
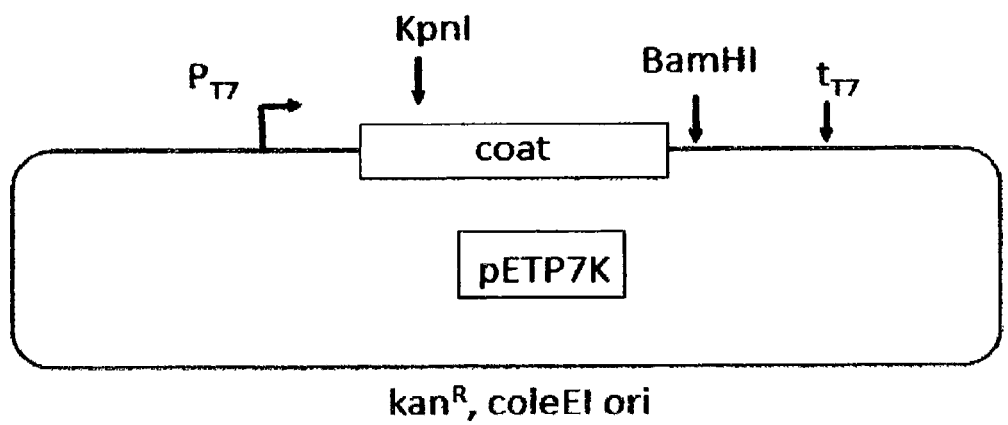
Figure 17B:
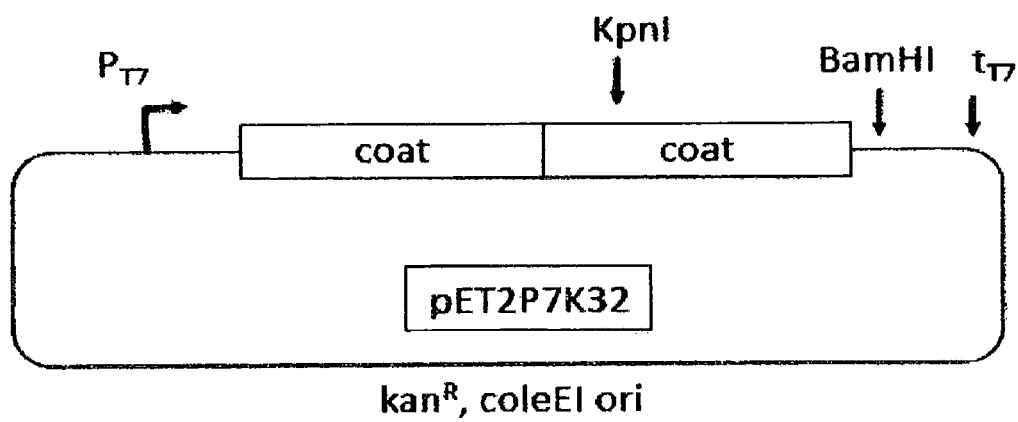
Figure 17C:
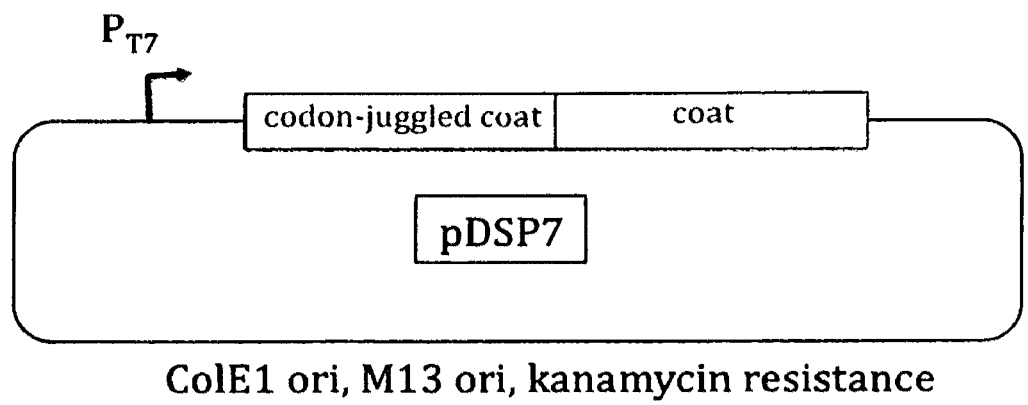

FIG. 17*a* depicts the pETP7K plasmid, FIG. 17*b* depicts the pET2P7K32 plasmid. and FIG. 17*c* depicts the pDSP7 plasmid. These plasmids were generated for the high level over-expression of PP7 coat protein. The pDSP7 plasmid contains a single-chain dimer of PP7 coat protein in which one half of the sequence contains a sufficient number of nucleotide substitutions in the vicinity of AB-loop-encoding sequences to render the two halves distinguishable for purposes of annealing a mutagenic oligonucleotide. In the example shown here, the entire upstream sequence is modified to contain the maximum number of silent mutations possible. pET2P7K32 and pDSP7 should be regarded as the PP7 analogs of the MS2 coat protein producers, pDSP1 and pDSP62.

Figure 18:
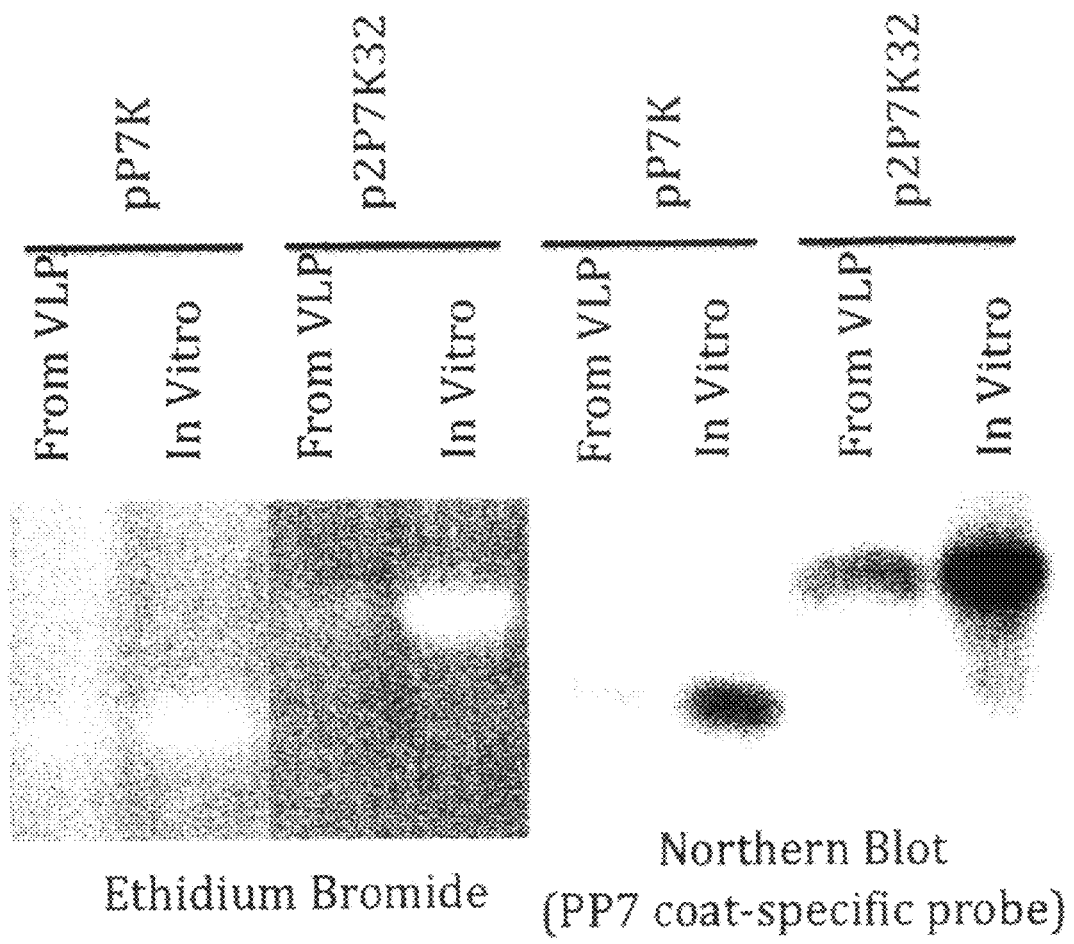

FIG. 18—Electrophoresis on formaldehyde/agarose gel of RNAs extracted from VLPs produced in bacteria containing pETP7K or pET2P7K32 shows that the VLPs they produce encapsidate the mRNAs that direct their synthesis. This provides the means of recovering affinity-selected sequences by reverse transcription and PCR. Alternate lanes contain RNAs produced by transcription in vitro of the same plasmids. The left panel shows the ethidium stained gel. On the right is a blot of a duplicate gel probed with an oligonucleotide specific for the PP7 coat protein sense-strand. This probe fails to react with similar quantities of RNA derived from in vitro transcription of MS2 or Qβ coat protein sequences (not shown).

FIG. 19 provides a list of several specific peptide sequences cloned into the PP7 coat protein.

Figure 20:
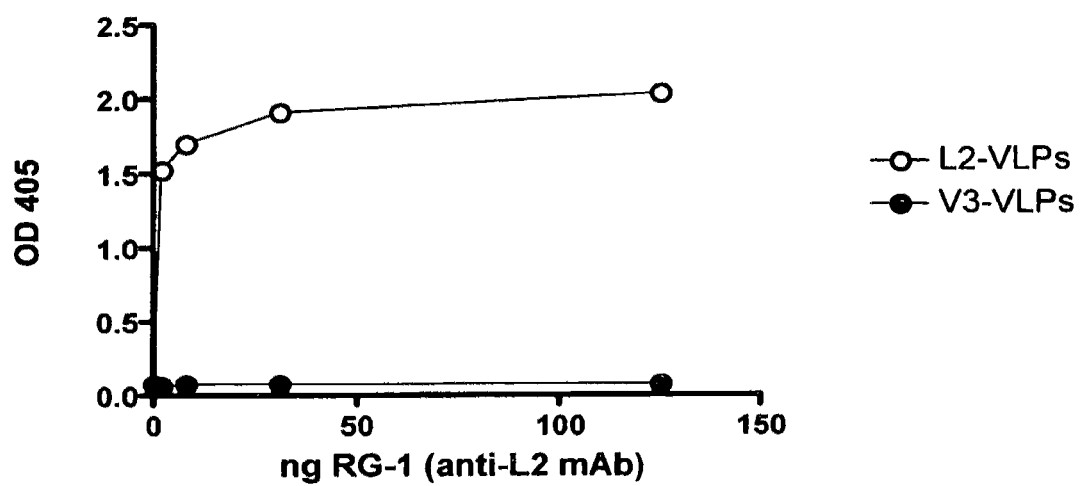

FIG. 20 illustrates that an anti-L2 mAb (RG-1) binds to PP7 L2-VLPs, but not PP7 V3-VLPs. Dilutions of mAb RG-1 were reacted with 500 ng/well of L2-VLPs or V3-VLPs. Binding was detected using a horseradish peroxidase-labeled goat anti-mouse IgG secondary followed by development with ABTS. Reactivity was determined by measurement of the absorbance at 405 nm (OD 405).

Figure 21:
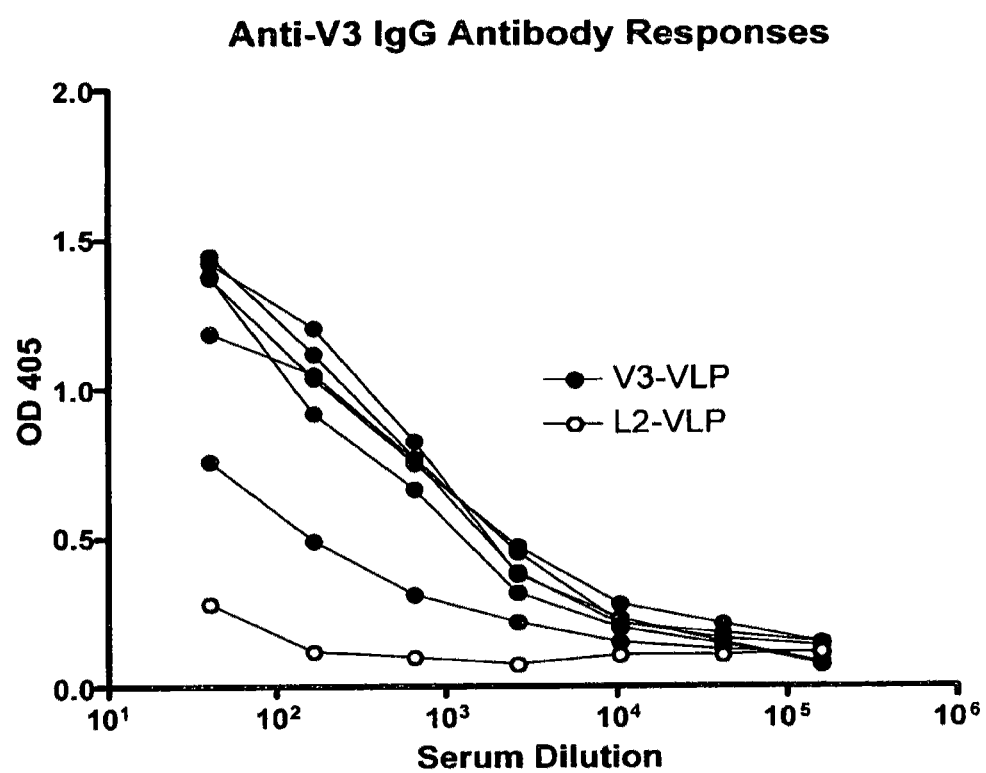

FIG. 21 illustrates that V3 peptide displaying PP7 VLPs induce anti-V3 IgG responses upon immunization. Shown are anti-V3 lgG antibody responses in mice immunized with PP7 V3-VLPs or, as a control, L2-VLPs. Mice were immunized three times with 10 µg of VLPs with incomplete Freund's adjuvant and then sera were collected two weeks after the final boost. Diluted sera from seven individual mice (six immunized with V3-VLPs and one immunized with L2-VLPs) were tested for reactivity with a peptide representing a portion of the V3 loop from $HIV_{LAI}$ by ELISA. Binding was detected using a horseradish peroxidase-labeled goat anti-mouse IgG secondary followed by development with ABTS. Reactivity was determined by measurement of the absorbance at 405 nm (OD 405).

FIG. 22 shows the results of affinity selection using MS2 VLP display with the anti-Flag M2 antibody whose epitope sequence has been thoroughly characterized previously by others. The sequences of a few peptides from each of the four rounds are shown to illustrate the progress of selection. Peptides found in rounds 1 and 2 contain recognizable elements of the native epitope, but by rounds 3 and 4 the similarity is obvious, the sequences closely matching that of the wild-type epitope. In fact the round 4 sequence matches the native epitope more closely than the sequences obtained previously by the well-established filamentous phage display method (see "NEB Transcript, Summer, 1006—available at the New England Biolabs web site, world wide web URL neb.com).

FIGS. 23*a*-23*d* show the nucleotide sequences of the pET2P7K32 (SEQ ID NO: 6), pET2P7K32(am) (SEQ ID NO: 7), pDSP7 (SEQ ID NO: 8), and pDSP7(am) (SEQ ID NO: 9) plasmids. These are the PP7 coat protein-producing analogs of the corresponding MS2 VLP producers shown in FIGS. 11*a*-11*d*.

DETAILED DESCRIPTION OF THE INVENTION

In accordance with the present invention, conventional molecular biology, microbiology, and recombinant DNA techniques within the skill of the art may be employed. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-Ill; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "an" and "the" include plural references unless the context clearly dictates otherwise.

Furthermore, the following terms shall have the definitions set out below.

As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, such as coding regions, and non-coding regions such as regulatory sequences (e.g., promoters or transcriptional terminators). A polynucleotide can be obtained directly from a natural source, or can be prepared with the aid of recombinant, enzymatic, or chemical techniques. A polynucleotide can be linear or circular in topology. A polynucleotide can be, for example, a portion of a plasmid or bacteriophage vector, such as an expression or cloning vector, or a fragment.

Restriction endonucleases are enzymes that cleave DNA at well-defined sequences. They are used in recombinant DNA technology, for example, to generate specific DNA fragments that are readily joined through the action of DNA ligase to other DNA fragments generated by digestion with the same restriction endonuclease. In this application, reference is made to several specific restriction endonucleases, including SalI, KpnI, and BamHI whose recognition sequences are, respectively: GTCGAC, GGTACC, and GGATCC.

As used herein, the term "polypeptide" refers broadly to a polymer of two or more amino acids joined together by peptide bonds. The term "polypeptide" also includes molecules that contain more than one polypeptide joined by a disulfide bond, or complexes of polypeptides that are joined together, covalently or noncovalently, as multimers (e g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

Figure 1:
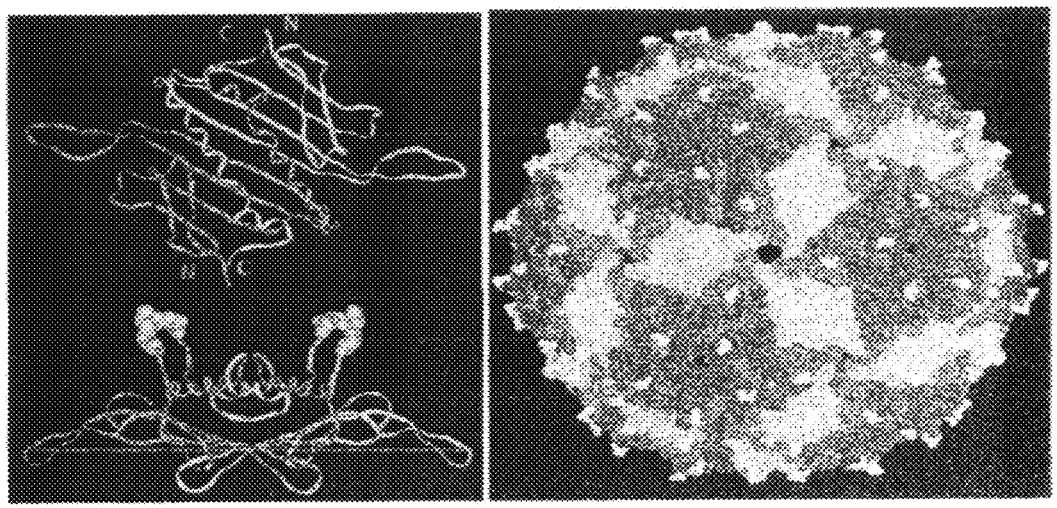
FIG. 1 illustrates the structure of the MS2 coat protein dimer. The top left panel emphasizes the proximity of N- and C-termini of the two subunit chains. This feature facilitated the construction of the single-chain dimer, which has high tolerance of foreign peptide insertions. Also illustrated (lower left) is the high accessibility of the AB-loop, both in the dimer and in the intact VLP. At right is shown the structure of the VLP itself. The coat proteins of which the VLP is comprised adopt three slightly different conformations according to the dicates of quasiequivalence and are shown in red, blue and green. The AB-loops are shown in yellow. Note their repetitious nature and their exposure on the VLP surface.

The term "single-chain dimer" refers to a normally dimeric protein whose two subunits have been genetically (chemically, through covalent bonds) fused into a single polypeptide chain. Specifically, in the present invention single-chain dimer versions of both MS2 and PP7 coat proteins were constructed. Each of these proteins is naturally a dimer of identical polypeptide chains. In both the MS2 and PP7 coat protein dimers the N-terminus of one subunit lies in close physical proximity to the C-terminus of the companion subunit (see FIG. 1). Single-chain coat protein dimers were produced using recombinant DNA methods by duplicating the DNA coding sequence of the coat proteins and then fusing them to one another in tail to head fashion. The result is a single polypeptide chain in which the coat protein amino acid appears twice, with the C-terminus of the upstream copy covalenty fused to the N-terminus of the downstream copy. Normally (wild-type) the two subunits are associated only through noncovalent interactions between the two chains. In the single-chain dimer these noncovalent interactions are maintained, but the two subunits have additionally been covalently tethered to one another. This greatly stabilizes the folded structure of the protein and confers to it its high tolerance of peptide insertions as described above.

This application makes frequent reference to coat protein's "AB-loop". The RNA phage coat proteins possess a conserved tertiary structure. The MS2 and the PP7 coat proteins, for example, each possess a structure exemplified by that of MS2 coat protein shown in FIG. 1. Each of the polypeptide chains is folded into of a number of β-strands designated by letters A through G. The β-strands A and B form a hairpin with a three-amino acid loop connecting the two strands at the top of the hairpin, where it is exposed on the surface of the VLP. As shown in this application, peptides inserted into the AB-loop are exposed on the surface of the VLP and are strongly immunogenic.

The amino acid residues described herein are preferred to be in the "L" isomeric form. However, residues in the "D" isomeric form can be substituted for any L-amino acid residue, as long as the desired function is retained by the polypeptide. $NH_2$ refers to the free amino group present at the amino terminus of a polypeptide. COOH refers to the free carboxy group present at the carboxy terminus of a polypeptide.

The term "coding sequence" is defined herein as a portion of a nucleic acid sequence that directly specifies the amino acid sequence of its protein product. The boundaries of the coding sequence are generally determined by a ribosome binding (or Shine-Dalgarno) site and a translation initiation codon (usually AUG) in prokaryotes, or by the AUG start codon in eukaryotes located at the start of the open reading frame, usually near the 5'-end of the mRNA, and a translation terminator sequence (one of the nonsense codons: UAG, UGA, or UAA) located at and specifying the end of the open reading frame, usually near the 3'-end of the mRNA. A coding sequence can include, but is not limited to, DNA, cDNA, and recombinant nucleic acid sequences.

As briefly noted above, a "stop codon" or "termination codon" is a nucleotide triplet within messenger RNA that signals a termination of translation. Proteins are unique sequences of amino acids, and most codons in messenger RNA correspond to the addition of an amino acid to a growing protein chain—stop codons signal the termination of this process, releasing the amino acid chain. In the standard genetic code, there are three stop codons: UAG (in RNA)/TAG (in DNA) (also known as an "amber" stop codon), UAA/TAA (also known as an "ochre" stop codon), and UGA/TGA (also known as an "opal" or "umber" stop codon). Several variations to this predominant group are known. The use of a stop codon in the present invention will normally stop or terminate protein synthesis. However, there are mutations in tRNAs which allow them to recognize the stop codons, causing ribosomes to read through the stop codon, allowing synthesis of peptides encoded downstream of the stop codon [11-13]. For example, a mutation in the tRNA which recognizes the amber stop codon allows translation to "read through" the codon and produce full length protein, thereby recovering the normal form of the protein and "suppressing" the stop codon. Most often, suppression of stop codons is only partially efficient—often only a few percent of ribosomes are permitted to read though the stop codon. In some instances, however, suppression can be much more efficient. A few suppressor tRNAs simply possess higher intrinsic suppressions efficiencies. In other cases a weak suppressor can be made more efficient by simply expressing it at higher levels. In certain embodiments of the present invention, a stop codon is incorporated into transcriptional units in order to control the synthesis of peptides encoded within the transcriptional unit downstream of the stop codon. By providing for the controlled synthesis of tRNA which recognize the stop codon and allow synthesis of peptides downstream of the stop codon, coat protein may be produced which comprise a heterologous peptide within a population of coat proteins, the majority of which do not contain a heterologous peptide. The resulting VLPs which are assembled from this mixture of heterologous peptide containing wild-type (absence of heterologous peptide) coat proteins result in a much lower valency of heterologous presentation.

A "heterologous" region of a recombinant cell is an identifiable segment of nucleic acid within a larger nucleic acid molecule that is not found in association with the larger molecule in nature. A "heterologous" peptide is a peptide which is an identifiable segment of a polypeptide that is not found in association with the larger polypeptide in nature.

The valency of a VLP refers to the number of copies of a heterologous peptide displayed on the particles. A virus particle which exhibits "low valency" of a heterologous peptide, preferably an immunogenic peptide of at least 4 peptide units, is a particle which displays from fewer than one to up to about ten or more heterologous peptides in the coat polypeptide dimers which comprise said virus particle. Virus particles which exhibit low valency are formed from a plurality of coat polypeptide dimers which are free of heterologous peptide (preferably, wild-type coat polypeptide) and a minority of coat polypeptide dimers which comprise heterologous peptide preferably within the A-B loop of the downstream subunit of the coat polypeptide or at the carboxy terminus of the single chain dimer coat polypeptide, thus forming a mosaic VLP.

Figure 7:
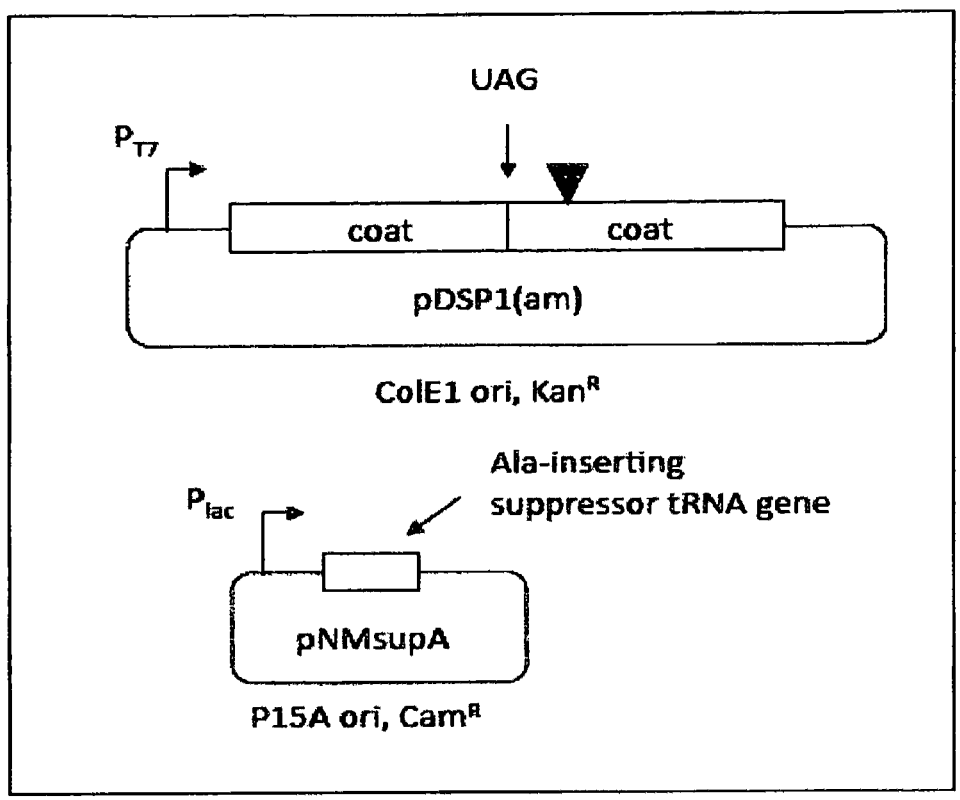
FIG. 7 shows an exemplary system for production of large amounts of wild-type and low quantities of AB-loop recombinant proteins from a single RNA. A variant of pDSP1 (pDSP1(am)) was constructed which contains an amber stop codon in place of the alanine codon normally encoding the first amino acid of the downstream copy of coat protein in the single-chain dimer. In addition, an alanine-inserting suppressor tRNA gene was synthesized and cloned which is produced in amounts that cause a small percentage of ribosomes translating the coat sequence to read through the amber (stop) codon and produce the single-chain dimer. The resulting protein (with its guest peptide) co-assembles with wild-type protein expressed from the same mRNA to form mosaic capsids and reduced valency as otherwise described herein.
Figure 8:
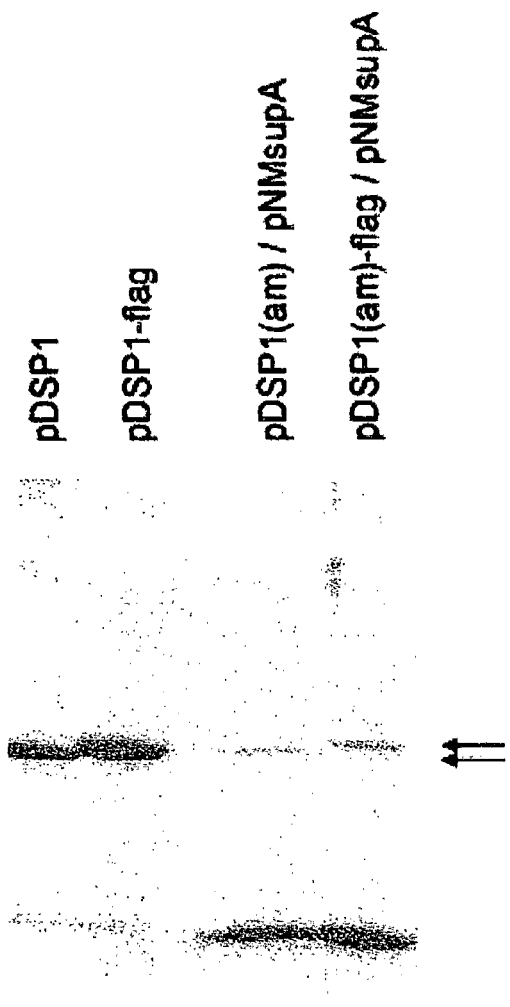
FIG. 8 is a representation of an SDS gel electrophoresis of purified VLPs produced by the plasmids listed below. The point of the experiment is to show the content of the single-chain "readthrough" product, as described for FIG. 7 above and in the examples section of the present application, in purified VLPs. The purified VLPs were produced from the following plasmids (left to right)

An "origin of replication", used within context, normally refers to those DNA sequences that participate in DNA synthesis by specifying a DNA replication initiation region. In the presence of needed factors (DNA polymerases, and the like) an origin of replication causes DNA associated with it to be replicated. For example, the ColE1 replication origin (used in plasmids like pDSP1, etc.) endows many commonly used plasmid cloning vectors with the capacity to replicate independently of the bacterial chromosome. Another example is the p15A replication origin, which is used in the plasmid pNMsupA, described elsewhere in this proposal (see FIG. 7). The presence on a plasmid of an additional origin of replication from phage M13 (e.g. as with pDSP62) confers the additional ability to replicate using that origin when *E. coli* cells are infected with a so-called helper phage (e.g. M13CM1 described in this application), which provides necessary protein factors. M13 replicates intracellularly as double-stranded circular DNA, but also produces a single-stranded circular form, which it packages within the phage particle. These particles provide a convenient source of single-stranded circular DNA for plasmids like pDSP62 and pDSP7 (described elsewhere in this application), which is useful for library construction using the method illustrated in FIG. 12.

A "promoter sequence" is a DNA regulatory region capable of binding RNA polymerase in a cell and initiating transcription of a downstream (3' direction) coding sequence. For purposes of defining the present invention, the promoter sequence includes the minimum number of bases or elements necessary to initiate transcription at levels detectable above background. Within the promoter will be found DNA sequences responsible for the binding of RNA polymerase and any of the associated factors necessary for transcription initiation. In bacteria promoters normally consist of −35 and −10 consensus sequences and a more or less specific transcription initiation site. Eukaryotic promoters will often, but not always, contain "TATA" boxes and "CAT" boxes. Bacterial expression vectors (usually plasmids or phages) typically utilize promoters derived from natural sources, including those derived from the *E. coli* Lactose, Arabinose, Tryptophan, and ProB operons, as well as others from bacteriophage sources. Examples include promoters from bacteriophages lambda, T7, T3 and SP6.

In bacteria, transcription normally terminates at specific transcription termination sequences, which typically are categorized as rho-dependent and rho-independent (or intrinsic) terminators, depending on whether they require the action of the bacterial rho-factor for their activity. These terminators specify the sites at which RNA polymerase is caused to stop its transcription activity, and thus they largely define the 3'-ends of the RNAs, although sometimes subsequent action of ribonucleases further trims the RNA.

An "antibiotic resistance gene" refers to a gene that encodes a protein that renders a bacterium resistant to a given antibiotic. For example, the kanamycin resistance gene directs the synthesis of a phosphotransferase that modifies and inactivates the drug. The presence on plasmids (e.g. pDSP1) of a kanamycin resistance gene provides a mechanism to select for the presence of the plasmid within transformed bacteria. Similarly, the chloramphenicol resistance gene allows bacteria to grow in the presence of the drug by producing an acetyltransferase enzyme that inactivates the antibiotic through acetylation. In the present application chloramphenicol resistance is used to ensure the maintenance within bacteria of pNMsupA and M13CM1.

"Reverse transcription and PCR" are presented in this application as a means of amplifying the nucleic acid sequences of affinity-selected VLPs. "Reverse transcription" refers to the process by which a DNA copy of an RNA molecule (or cDNA) is produced by the action of the enzyme reverse transcriptase. In the present application, reverse transcription is used to produce a DNA copy of RNA sequences encapsidated with affinity-selected VLPs. The reverse transcriptase enzyme requires a primer be annealed to the RNA (see below).

The term "PCR" refers to the polymerase chain reaction, a technique used for the amplification of specific DNA sequences in vitro. The term "PCR primer" refers to DNA sequences (usually synthetic oligonucleotides) able to anneal to a target DNA, thus allowing a DNA polymerase (e.g. Taq DNA polymerase) to initiate DNA synthesis. Pairs of PCR primers are used in the polymerase chain reaction to initiate DNA synthesis on each of the two strands of a DNA and to thus amplify the DNA segment between the two primers, as illustrated, for example, in FIGS. 9*b* and 15.

Examples of primers used for reverse transcription and PCR are given here.

E2: 5' TCA GCG GTG GCA GCA GCC AA 3'—SEQ ID NO:10—anneals near the 3'-ends of the RNAs encapsdiated by the VLPs described in this application; used to prime reverse transcription.

E3.2: 5' CGG GCT TTG TTA GCA GCC GG 3'—SEQ ID NO:11—anneals near the 3'ends of the cDNAs generated by reverse transcription described above at a site just upstream of the E2 primer site; serves as the 3'-primer in PCR reactions to amplify affinity-selected sequences.

The E2 and E3.2 primers contain sequences common to pDSP1, pDSP1(am), pDSP62, pDSP62(am), pET2P7K32, pET2P7K32(am), pDSP7, and pDSP7(am) and are therefore useful for reverse transcription and PCR of RNA encapsidated by VLPs from each of these sources. PCR depends on pairing E3.2 with one of the plasmid-specific 5'-primers described below. For simplicity only the primers for pDSP1 and pDSP1(am) are shown, but it should be understood that similar primers specific for the sequences found in the other VLPs are utilized as needed.

J2: 5' ACT CCG GCC TCT ACG GCA AC 3'—SEQ ID NO:12—a primer that anneals specifically to sequences at the junction between the single-chain dimer sequences of pDSP1. In a PCR reaction with E3.2, a DNA segment is amplified that contains the downstream half of the single-chain dimer (including the sequence of the peptide inserted in the AB-loop). Digestion of the PCR product with SalI and BamHI produces a fragment that can be inserted between SalI and BamHI of the relevant plasmid (see FIG. 9*a*, for example) J2(amber): 5' AC TCC GGC ATC TAC TAG AAC TTT AC 3'—SEQ ID NO:13—This primer functions exactly like J2 above, but is specific for the sequences generated form pDSP1(am).

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence. Transcriptional control sequences are DNA regulatory sequences, such as promoters, enhancers, polyadenylation signals, terminators, and the like, that provide for the expression of a coding sequence in a host cell. Translational control sequences determine the efficiency of translation of a messenger RNA, usually by controlling the efficiency of ribosome binding and translation initiation. For example, as discussed elsewhere in this application, the coat proteins of the RNA phages are well-known translational repressors of the phage replicase. As coat protein accumulates to a sufficiently high concentration in the infected cell, it binds to an RNA hairpin that contains the translation initiation region (Shine-Dalgarno and initiator AUG) of the phage's replicase gene. This prevents ribosome binding and shuts off replicase synthesis at a time in the viral life cycle where the transition from replication to virus assembly occurs.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid, which normally replicate independently of the bacterial chromosome by virtue of the presence on the plasmid of a replication origin. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

It should be appreciated that also within the scope of the present invention are nucleic acid sequences encoding the polypeptide(s) of the present invention, which code for a polypeptide having the same amino acid sequence as the sequences disclosed herein, but which degenerate to the nucleic acids disclosed herein. By "degenerate to" is meant that a different three-letter codon is used to specify a particular amino acid.

As used herein, "epitope" refers to an antigenic determinant of a polypeptide. An epitope could comprise 3 amino acids in a spatial conformation which is unique to the epitope. Generally an epitope consists of at least 5 such amino acids, and more usually, consists of at least 8-10 such amino acids. Methods of determining the spatial conformation of amino acids are known in the art, and include, for example, x-ray crystallography and 2-dimensional nuclear magnetic resonance.

As used herein, a "mimotope" is a peptide that mimics an authentic antigenic epitope. In some cases the amino acid sequence may show some similarities with the epitope of the original antigen, but in some cases little or no sequence similarity exists. In such cases the mimotope mimics the 3D structure of the epitope using a different amino acid sequence. Mimotopes may be identified that mimic even non-peptide epitopes, such as those of carbohydrate antigens.

As used herein, the term "coat protein(s)" refers to the protein(s) of a bacteriophage or a RNA-phage capable of being incorporated within the capsid assembly of the bacteriophage or the RNA-phage.

As used herein, a "coat polypeptide" is defined herein as a polypeptide fragment of the coat protein that possesses coat protein function and additionally encompasses the full length coat protein as well or single-chain variants thereof.

As used herein, the term "immune response" refers to a humoral immune response and/or cellular immune response leading to the activation or proliferation of B- and/or T-lymphocytes and/or and antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant. Preferably, antigen-presenting cells may be activated.

As used herein, the term "self antigen" refers to proteins encoded by the host's DNA and products generated by proteins or RNA encoded by the host's DNA. In addition, proteins that result from a combination of two or several self-molecules or that represent a fraction of a self-molecule and proteins that have a high homology or the two self-molecules as defined above (>95%, preferably >97%, more preferably >99%) may also be considered self. Examples of a self-antigen includes but is not limited to ErbB-2, amyloid-beta, immunoglubulin E (IgE), gastrin, ghrelin, vascular endothelial growth factor (VEGF), interleukin (IL)-17, IL-23, IL-13, CCR5, CXCR4, nerve growth factor (NGF), angiotensin II, TRANCE/RANKL and MUC-1.

As used herein, the term "vaccine" refers to a formulation which contains the composition of the present invention and which is in a form that is capable of being administered to an animal.

As used herein, the term "virus-like particle of a bacteriophage" refers to a virus-like particle (VLP) resembling the structure of a bacteriophage, being non replicative and non-infectious, and usually lacking one or more viral genes needed for propagation of the bacteriophage as an infectious virus. The VLPs of RNA bacteriophages typically also lacking the gene or genes encoding the protein or proteins responsible for viral attachment to or entry into the host.

This definition also encompasses virus-like particles of bacteriophages, in which the aforementioned gene or genes are still present but inactive, and, therefore, also leading to non-replicative and noninfectious virus-like particles of a bacteriophage.

"VLP of RNA bacteriophage coat protein" is defined as the capsid structure formed from the self-assembly of one or more subunits of RNA bacteriophage coat protein and usually containing mRNA for the coat protein itself, and optionally containing host RNA. For the purposes of this application RNA phage VLPs are usually assembled from 180 copies of a wild-type coat protein dimer, or from 90 copies of a single-chain dimer coat protein, or as mosaic VLPs containing variable numbers of wild-type dimer and single-chain dimer coat proteins totaling 90 per particle.

A nucleic acid molecule is "operatively linked" to, or "operably associated with" an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

The term "stringent hybridization conditions" are known to those skilled in the art and can be found in Current Protocols in Molecular Biology, John Wiley & Sons, N.Y. (1989), 6.3.1-6.3.6. A preferred, non-limiting example of stringent hybridization conditions is hybridization in 6× sodium chloride/sodium citrate (SSC) at about 45° C., followed by one or more washes in 0.2.×SSC, 0.1% SDS at 50° C., preferably at 55° C., and more preferably at 60° C. or 65° C.

Production of Virus-Like Particles

The present invention is directed to virus-like phage particles as well as methods for producing these particles in vivo and in vitro. Normally, these particles are produced in vivo, however, the use of these particles may well be applied in an in vitro setting and this approach is anticipated by the present invention. The invention makes it possible to increase laboratory complexity and reduce the time needed for iterative selection. The methods typically include producing virions in vitro and recovering the virions. As used herein, producing virions "in vitro" refers to producing virions outside of a cell, for instance, in a cell-free system, while producing virions "in vivo" refers to producing virions inside a cell, for instance, an *Eschericia coli* or *Pseudomonas aeruginosa* cell.

Bacteriophages

The system envisioned here is based on the properties of single-strand RNA bacteriophages (see RNA Bacteriophages, in The Bacteriophages. Calendar, R L, ed. Oxford University Press. 2005). The known viruses of this group attack bacteria as diverse as *E. coli, Pseudomonas* and *Acinetobacter*. Each possesses a highly similar genome organization, replication strategy, and virion structure. In particular, the bacteriophages contain a single-stranded (+)-sense RNA genome, contain maturase, coat and replicase genes, and have small (<300 angstrom) icosahedral capsids. These include but are not limited to MS2, Qβ, R17, SP, PP7, GA, M11, MX1, f4, Cb5, Cb12r, Cb23r, 7s and f2 RNA bacteriophages.

PP7 is a single-strand RNA bacteriophage of *Pseudomonas aeroginosa* and a distant relative to coliphages like MS2 and Qβ. Although the PP7 bacteriophage normally infects *Pseudomonas aeroginosa*, virus-like particles are readily produced when the PP7 coat protein is expressed in *E. coli* from plasmids such as those described in FIGS. 9 and 13. It was determined that PP7 coat protein is a specific RNA-binding protein, capable of repressing the translation of sequences fused to the translation initiation region of PP7 replicase, with specific RNA binding activity since it represses the translational operator of PP7, but does not repress the operators of the MS2 or Qβ phages. Conditions for the purification of coat protein and for the reconstitution of its RNA binding activity from disaggregated virus-like particles have been established. The dissociation constant for PP7 operator RNA in vitro was determined to be about 1 nM. Using a genetic system in which coat protein represses translation of a replicase-β-galactosidase fusion protein, amino acid residues important for binding of PP7 RNA were identified. Peabody, et al., Translational repression and specific RNA binding by the coat protein of the *Pseudomonas* phage PP72001, *J. Biol. Chem.*, June 22; 276(25):22507-13. Epub 2001 Apr. 16.

The coat proteins of several single-strand RNA bacteriophages are known translational repressors, shutting off viral replicase synthesis by binding an RNA hairpin that contains the replicase ribosome binding site. X-ray structure determination of RNA phages shows that homologies evident from comparisons of coat protein amino acid sequences are reflected in the tertiary structures. The coat protein dimer, which is both the repressor and the basic building block of the virus particle, consists of two intertwined monomers that together form a large β-sheet surface upon which the RNA is bound. Each of the coat proteins uses a common structural framework to bind different RNAs, thereby presenting an opportunity to investigate the basis of specific RNA-protein recognition. The RNA binding properties of the coat protein of PP7, an RNA bacteriophage of *Pseudomonas aeroginosa* whose coat protein shows only 13% amino acid sequence identity to that of MS2 is described herein. Also presented are the following findings: (1) the coat protein of PP7 is a translational repressor; (2) an RNA hairpin containing the PP7 replicase translation initiation site is specifically bound by PP7 coat protein both in vivo and in vitro, indicating that this structure represents the translational operator; and, (3) the RNA binding site resides on the coat protein β-sheet. A map of this site has been presented. Id.

For purposes of illustration, the genome of a particularly well-characterized member of the group is utilized, MS2, which is a single strand of (+)-sense RNA 3569 nucleotides long, encoding only four proteins, two of which are structural components of the virion. The viral particle is comprised of an icosahedral capsid made of 180 copies of coat protein and one molecule of maturase protein together with one molecule of the RNA genome. Coat protein is also a specific RNA binding protein. Assembly may be initiated when coat protein associates with its specific recognition target, an RNA hairpin near the 5'-end of the replicase cistron (see FIG. 1B and SEQ ID NO: 1 of US20090054246, published Feb. 26, 2009, incorporated by reference in its entirety herein). The virus particle is then liberated into the medium when the cell bursts under the influence of the viral lysis protein. The formation of an infectious virus requires at least three components, namely coat protein, maturase and viral genome RNA, but experiments show that the information required for assembly of the icosahedral capsid shell is contained entirely within coat protein itself. For example, purified coat protein can form capsids in vitro in a process stimulated by the presence of RNA (Beckett et al., 1988, J. Mol Biol 204: 939-47). Moreover, coat protein expressed in cells from a plasmid assembles into a virus-like particle in vivo (Peabody, D. S., 1990, J Biol Chem 265: 5684-5689).

Coat Polypeptide

The coat polypeptide encoded by the coding region is typically at least 120, preferably, at least 125 amino acids in length, and no greater than about 135 amino acids in length, preferably, no greater than 130 amino acids in length. It is expected that a coat polypeptide from essentially any single-stranded RNA bacteriophage can be used. Examples of coat polypeptides include but are not limited to the MS2 coat polypeptide (see, for example SEQ ID N0:2 of US published application US20090054246), R17 coat polypeptide (see, for example, Genbank Accession No. P03612), PRR1 coat polypeptide (see, for example, Genbank Accesssion No. ABH03627), fr phage coat polypeptide (see, for example, Genbank Accession No. NP_039624), GA coat polypeptide (see, for example, Genbank Accession No. P07234), Qβ coat polypeptide (see, for example, Genbank Accession No. P03615), SP coat polypeptide (see, for example, Genbank Accession No P09673), f4 coat polypeptide (see, for example, Genbank accession No. M37979.1) and PP7 coat polypeptide (see, for example, Genbank Accession No. PO363 0).

Examples of PP7 coat polypeptides include but are not limited to the various chains of PP7 Coat Protein Dimer in Complex With RNA Hairpin (e.g. Genbank Accession Nos. 2QUXR; 2QUXO; 2QUX_L; 2QUX_I; 2QUX_F; and 2QUX_C). See also Example 1 herein and Peabody, et al., RNA recognition site of PP7 coat protein, Nucleic Acids Research, 2002, Vol. 30, No. 19 4138-4144. [14, 15]

The coat polypeptides useful in the present invention also include those having similarity with one or more of the coat polypeptide sequences disclosed above. The similarity is referred to as structural similarity. Structural similarity may be determined by aligning the residues of the two amino acid sequences (i.e., a candidate amino acid sequence and the amino acid sequence) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence is the amino acid sequence being compared to an amino acid sequence present in for example, SEQ ID NO: 2 of U.S. Patent Published Application No. US2009/0054246. A candidate amino acid sequence can be isolated from a single stranded RNA virus, or can be produced using recombinant techniques, or chemically or enzymatically synthesized. Preferably, two amino acid sequences are compared using the BESTFIT algorithm in the GCG package (version 10.2, Madison Wis.), or the Blastp program of the BLAST 2 search algorithm, as described by Tatusova, et al. (*FEMS Microbial Lett* 1999, 174:247-250), and available at http://www.ncbi.nlm.nih.gov/blast/bl2seq/bl2.html. Preferably, the default values for all BLAST 2 search parameters are used, including matrix=BLOSUM62; open gap penalty=11, extension gap penalty=1, gap xdropoff=50, expect=10, wordsize=3, and optionally, filter on. In the comparison of two amino acid sequences using the BLAST search algorithm, structural similarity is referred to as "identities."

Preferably, a coat polypeptide also includes polypeptides with an amino acid sequence having at least 80% amino acid identity, at least 85% amino acid identity, at least 90% amino acid identity, or at least 95% amino acid identity to one or more of the amino acid sequences disclosed above. Preferably, a coat polypeptide is active. Whether a coat polypeptide is active can be determined by evaluating the ability of the polypeptide to form a capsid and package a single stranded RNA molecule. Such an evaluation can be done using an in vivo or in vitro system, and such methods are known in the art and routine. Alternatively, a polypeptide may be considered to be structurally similar if it has similar three dimensional structure as the recited coat polypeptide and/or functional activity.

Heterologous peptide sequences inserted into the coat polypeptide or polypeptide may be a random peptide sequence. In a particular embodiment, the random sequence has the sequence $Xaa_n$, wherein n is at least 4, at least 6, or at least 8 and no greater than 20, no greater than 18, or no greater than 16, and each Xaa is independently a random amino acid. Alternatively, the peptide fragment may have a defined sequence and possess a known functionality (e.g., antigenicity, immunogenicity). The heterologous sequence may be present at the amino-terminal end of a coat polypeptide, at the carboxy-terminal end of a coat polypeptide, or present elsewhere within the coat polypeptide. Preferably, the heterologous sequence is present at a location in the coat polypeptide such that the insert sequence is expressed on the outer surface of the capsid. In a particular embodiment, and as described in the examples hereafter, the peptide sequence may be inserted into the AB loop regions the above-mentioned coat polypeptides. Examples of such locations include, for instance, insertion of the insert sequence into a coat polypeptide immediately following amino acids 11-17, or amino acids 13-17 of the coat polypeptide. In a most particular embodiment, the heterologous peptide is inserted at a site corresponding to amino acids 11-17 or particularly 13-17 of MS-2.

In certain embodiments according to the present invention, the heterologous peptide is inserted at a site corresponding to:
(a) amino acids 11-17 or particularly 13-17 of MS-2, R17 and fr coat polypeptides;
(b) amino acids 10-16 of GA coat polypeptide
(c) amino acids 10-17 of Qβ and SP coat polypeptides;
(d) amino acids 8-11 of PP7 coat polypeptides and
(e) amino acids 9-17 of PRR1 coat polypeptides.
Alternatively, the heterologous peptide may be inserted at the N-terminus or C-terminus of the coat polypeptide.

The heterologous peptide may be selected from the group consisting of an HIV peptide, a self antigen, Flag peptide, amino acid sequences derived from the minor capsid protein L2 of human Papillomavirus type 16 (HPV16), the V3 loop of HIV-1 gp120, *Bacillus anthracis* protective antigen, a receptor, a ligand which binds to a cell surface receptor, a peptide with affinity for either end of a filamentous phage particle specific peptide, a metal binding peptide or a peptide with affinity for the surface of MS2.

The heterologous peptide includes but is not limited to a peptide selected from the group consisting of an HIV peptide, a self antigen, Flag peptide, amino acid sequences derived from the minor capsid protein L2 of human Papillomavirus type 16 (HPV16), the V3 loop of HIV-1 gp120, *Bacillus anthracis* protective antigen, a receptor, a ligand which binds to a cell surface receptor, a peptide with affinity for either end of a filamentous phage particle specific peptide, a metal binding peptide or a peptide with affinity for the surface of PP7.

In order to determine a corresponding position in a structurally similar coat polypeptide, the amino acid sequence of this structurally similar coat polypeptide is aligned with the sequence of the named coat polypeptide as specified above. For example, the corresponding position of a coat polypeptide structurally similar to MS-2 coat polypeptide is aligned with SEQ ID NO: 2 (of published US Patent Application, US2009/0054246, which is incorporated by reference herein). From this alignment, the position in the other coat polypeptide which corresponds to a given position of SEQ ID NO: 1 (also of published US Patent application, US2009/0054246) can be determined.

In a particular embodiment, the coat polypeptide is a single-chain dimer containing an upstream and downstream subunit. Each subunit contains a functional coat polypeptide sequence. The heterologous peptide may be inserted into the upstream and/or downstream subunit at the sites mentioned herein above, e.g., preferably, the A-B loop region of the downstream subunit. In a particular embodiment, the coat polypeptide is a single chain dimer of an MS2 coat polypeptide which may have a sequence depicted in SEQ ID NO: 12 of published US Patent application, US2009/0054246, which is incorporated by reference herein.

In a particular embodiment, the coat polypeptide is a single-chain dimer containing an upstream and downstream subunit. Each subunit contains a functional coat polypeptide sequence. The heterologous peptide may be inserted on the upstream and/or downstream subunit at the sites mentioned herein above, e.g., AB loop region of downstream subunit. In a particular embodiment, the coat polypeptide is a single chain dimer of a PP7 coat polypeptide.

Preparation of Transcription Unit

The transcription unit of the present invention comprises an expression regulatory region, (e.g., a promoter), a sequence encoding a coat polypeptide and transcription terminator. The RNA polynucleotide may optionally include a coat recognition site (also referred to a "packaging signal", "translational operator sequence", "coat recognition site"). Alternatively, the transcription unit may be free of the translational operator sequence. The promoter, coding region, transcription terminator, and, when present, the coat recognition site, are generally operably linked. "Operably linked" or "operably associated with" refers to a juxtaposition wherein the components so described are in a relationship permitting them to function in their intended manner. A regulatory sequence is "operably linked" to or "operably associated with", a coding region when it is joined in such a way that expression of the coding region is achieved under conditions compatible with the regulatory sequence. The coat recognition site, when present, may be at any location within the RNA polynucleotide provided it functions in the intended manner.

The invention is not limited by the use of any particular promoter, and a wide variety of promoters are known. The promoter used in the invention can be a constitutive or an inducible promoter. Preferred promoters are able to drive high levels of RNA encoded by me coding region encoding the coat polypeptide. Examples of such promoters are known in the art and include, for instance, the lac promoter T7, T3, and SP6 promoters.

The nucleotide sequences of the coding regions encoding coat polypeptides described herein are readily determined. An example of the class of nucleotide sequences encoding one of the coat polypeptides described herein is nucleotides 4080-4470 of SEQ ID N0:3 (of published US Patent application, US2009/0054246, incorporated by reference herein). These classes of nucleotide sequences are large but finite, and the nucleotide sequence of each member of the class can be readily determined by one skilled in the art by reference to the standard genetic code.

Furthermore, the coding sequence of an RNA bacteriophage single chain coat polypeptide comprises a site for insertion of a heterologous peptide as well as a coding sequence for the heterologous peptide itself. In a particular embodiment, the site for insertion of the heterologous peptide is a restriction enzyme site.

Figure 3:
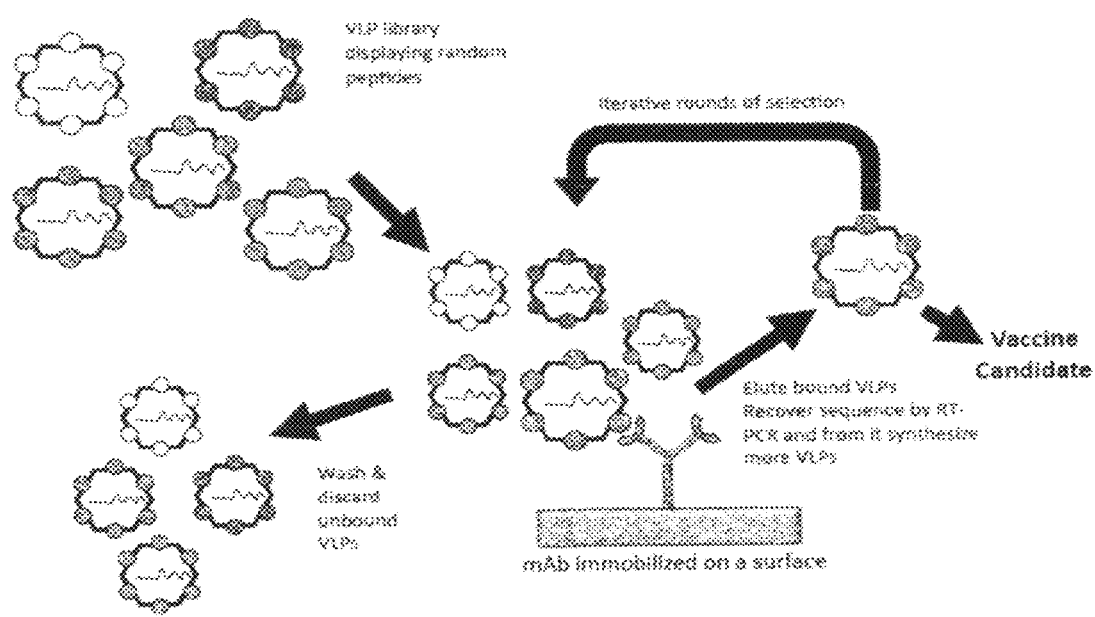
FIG. 3 illustrates the process of affinity selection. A population of VLPs representing a random sequence peptide library is incubated with a monoclonal antibody immobilized on a surface. The vast majority of VLPs typically fail to bind the antibody and are washed away and discarded. Any VLPs whose peptides exhibit binding of the antibody are then specifically eluted, the RNA they contain is copied into DNA by reverse transcription, amplified by PCR and then re-cloned into an expression plasmid (e.g. pDSP62 or pDSP62(am)) for production of the affinity-selected VLP. Selection is typically conducted iteratively (i.e. more than twice) preferably for 3 to 5 rounds.

In a particular embodiment, the coding region encodes a single-chain dimer of the coat polypeptide. In a most particular embodiment, the coding region encodes a modified single chain coat polypeptide dimer, where the modification comprises an insertion of a coding sequence of at least four amino acids at the insertion site. A schematic diagram of a particular embodiment of such a transcription unit is shown in FIG. 3 of published US Patent application, US2009/0054246. The transcription unit may contain a bacterial promoter, such as a lac promoter or it may contain a bacteriophage promoter, such as a T7 promoter and optionally, a T7 transcription terminator.

In addition to containing a promoter and a coding region encoding a fusion polypeptide, the RNA polynucleotide typically includes a transcription terminator, and optionally, a coat recognition site. A coat recognition site is a nucleotide sequence that forms a hairpin when present as RNA. This is also referred to in the art as a translational operator, a packaging signal, and an RNA binding site. Without intending to be limiting, this structure is believed to act as the binding site recognized by the translational repressor (e.g., the coat polypeptide), and initiate RNA packaging. The nucleotide sequences of coat recognition sites are known in the art and include, for instance, nucleotides in SEQ ID NO: 1 (see FIG. 1B of published US Patent application, US2009/0054246). Other coat recognition sequences have been characterized in the single stranded RNA bacteriophages R17, GA, Qβ, SP, and PP7, and are readily available to the skilled person. Essentially any transcriptional terminator can be used in the RNA polynucleotide, provided it functions with the promoter. Transcriptional terminators are known to the skilled person, readily available, and routinely used.

Synthesis

As will be described in further detail below, the VLPs of the present invention may be synthesized in vivo by introducing transcription units into bacteria, especially if transcription units contain a bacterial promoter. Alternatively VLPs could be produced in vitro in a coupled cell-free transcription/translation system.

Assembly of VLPs Encapsidating Heterologous Substances

During their synthesis VLPs normally associate with the messenger-RNA from which they are produced by translation. This is important for the affinity-selection capability of the system described in this application. However, in some other applications (e.g. targeted delivery of drugs or imaging agents) it may be desirable to introduce other substances into the VLP. These VLPs may be assembled by performing an in vitro VLP assembly reaction in the presence of the heterologous substance. Specifically, purified coat protein subunits are obtained from VLPs that have been disaggregated with a denaturant (usually acetic acid). The protein subunits are mixed with the heterologous substance. In a particular embodiment, the substance has some affinity for the interior of the VLP and is preferably negatively charged.

Another method involves attaching the heterologous substance to a synthetic RNA version of the translational operator. During an in vitro assembly reaction, the RNA will tightly bind to its recognition site and be efficiently incorporated into the resulting VLP, carrying with it the foreign substance.

In another embodiment, the substance is passively diffused into the VLP through pores that naturally exist in the VLP surface. In a particular embodiment, the substance is small enough to pass through these pores (in MS2 they're about 10 angstroms diameter) and has a high affinity for the interior of the VLP.

VLP Populations

As noted above, the invention is directed to VLP populations or libraries. The terms "population" and "libraries" in the instant specification are used interchangeably and are thus deemed to be synonymous. In one particular embodiment, the library may be a random library; in another embodiment, the library is an antigen fragment library, a library of fragments derived from an antigenic polypeptide.

Random Libraries (Populations)

Oligonucleotides encoding peptides may be prepared. In one particular embodiment, the triplets encoding a particular amino acid have the composition NNS where N is A, G, C or T and S is G or T or alternatively NNY where N is A, G, C, or T and Y is C or T. Multiple triplets are inserted into the coat protein gene, leading the insertion of corresponding peptides into the protein product. In order to minimize the presence of stop codons, peptide libraries can be constructed using oligonucleotides synthesized from custom trinucleotide phosphoramidite mixtures (available from Glen Research, Inc.) designed to more accurately reflect natural amino acid compositions and completely lacking stop codons.

The insertion of such random sequences into coat protein leads to the synthesis of a population (or library) of VLPs, each particle displaying a different peptide on its surface. Such populations may be extremely large, consisting of billions of individual members. It is commonly observed that ligands specific for practically any receptor (e.g. a monoclonal antibody) are present in such libraries, although they will usually represent a tiny fraction of the whole population. Affinity selection, followed by amplification (in the case of the present invention by reverse transcription and PCR of encapsidated RNA) allows the recovery, analysis and exploitation of such rare species.

EXAMPLES

The invention may be better understood by reference to the following non-limiting examples, which are provided as exemplary of the invention. The following examples are presented in order to more fully illustrate the preferred embodiments of the invention and should in no way be construed, however, as limiting the broad scope of the invention.

Production of VLPs Exhibiting Heterologous Peptides of Low Valency.

The present application details recent advances in development of the technology for peptide display on MS2 VLPs, including descriptions of new plasmid vectors for the facile production of random sequence peptide libraries and for control of peptide display valency. This represents an advance of the methodologies which are described in published US application, US20090054246.

The present invention is directed to developing an MS2 Virus-Like Particle (VLP) platform with an affinity selection capability analogous to that of filamentous phage display. The present invention is, in part, based on the ability of the coat proteins of RNA bacteriophages both to display foreign peptides and to encapsidate the same mRNAs that serve as templates for their synthesis. The process entails the synthesis of coat protein-random peptide fusions from plasmids in bacterial cells which form VLPs. The VLPs are extracted from cells and subjected to affinity selection for binding to specific antibodies. Finally, RNA is extracted from the selected VLPs and subjected to reverse transcription and PCR to recover and amplify the encapsidated sequences, which are then cloned and reintroduced into bacteria, where they serve as templates for another round of synthesis, assembly and selection. The process is repeated through as many cycles as needed and, in the end, the selected sequences are cloned for high-level bacterial expression of the selected VLPs.

The present method, which is being developed to facilitate vaccine discovery, among several other uses, possesses important features that were not available together in a single platform. First, the present method ensures high immunogenicity by displaying foreign peptides as dense repetitive arrays on the surface of a virus-like particle (VLP). This results not only in vigorous immune responses to foreign antigens, but can also overcome immune tolerance and induce antibodies against self-antigens. Second, in a process analogous to phage display, the platforms of the present invention permit recovery and amplification of affinity-selected sequences from complex random sequence libraries. The present invention thus combines in a single platform the ability to identify relevant epitopes by valency limitation and affinity-selection, and to then present those epitopes to the immune system as a vaccine. Epitopes are identified and optimized by affinity-selection against an antibody target, and then, without changing platforms, may be presented directly to the immune system as a vaccine. The peptides are displayed at high density without altering the structural constraints present during their original selection, thus increasing the likelihood that faithful molecular mimics of the native epitope are isolated, that their optimal structures are maintained during the immunization process, and that relevant antibody responses are induced.

Plasmid Vectors for High Complexity Random Sequence Peptide Library Construction on MS2 VLPs.

The first experiments utilizing MS2 VLP random sequence peptide libraries were carried out in simple derivatives of pET3d, an ampicillin resistent plasmid with a T7 transcription unit. This turned out to be a somewhat less than optimal system for convenient production of high complexity libraries, however, and the inventors have since created a series of vectors that combine a number of optional features which appear to be important. These include:

A. A Single-Chain Dimer with Convenient Cloning Sites for Insertion in the AB-Loop.

pDSP1 (FIG. 1) expresses the coding sequence of the single-chain dimer, modified to contain for example, unique SalI and KpnI restriction sites in or near the AB-loop-encoding sequences. Typically a BamHI site is included downstream of the coat sequence. This form of the dimer facilitates simple cloning of foreign sequences into the AB-loop. To make these sites unique, it was necessary to destroy a number of SalI and KpnI sites in the vector and in the upstream coat sequence and in plasmid sequences.

B. Kanamycin Resistance.

pDSP1 confers resistance to kanamycin. This greatly facilitates library construction by permitting selection of transformed bacteria in liquid culture against an initially high background of untransformed cells. The ampicillin resistance conferred by the first generation plasmid vectors was unsuited to this purpose, because rapid degradation of the antibiotic by transformed E. coli results in loss of selection after a surprisingly short time in culture. This would have allowed the overgrowth of untransformed cells, which, of course, normally represent the great majority of the population, even when efficient transformation methods are utilized.

C. An M13 Origin of Replication.

Until now the inventors have constructed random sequence libraries by a procedure in which a PCR primer is utilized to generate a fragment with the randomized sequence attached at one end. The fragment is then digested with appropriate restriction endonucleases and cloned in pDSP1 at the unique sites described above (typically between SalI and BamHI, see FIG. 1). Using such methods the inventors have made libraries consisting of up to $10^9$ individual recombinants. However, libraries of this size are inconvenient to construct using these methods; the construction of much larger libraries is facilitated by methods that efficiently produce larger yields of recombinant DNA than are found in a typical ligation reaction. Specifically, the inventors make use of a variation of a method for site-directed mutagenesis (2), which has been used already by others to produce filamentous phage libraries in the $10^{11}$ complexity range (3). The method relies on extension of a mis-matched primer on a dUTP-substituted single-stranded circular template. (Substitution of dT with dU is accomplished by growth of the template DNA in a dut−, ung− host like CJ236 or BW313.) For the purpose of creating random sequence peptide libraries the primer contains a random DNA sequence flanked on each side by sequences complementary to coat sequences on either side of the AB-loop. The primer is extended with DNA polymerase and a covalently closed double-stranded circle is produced by the action of DNA ligase. Transformation (e.g. by electroporation) of an ung+ strain results in strong selection for selective propagation of the mutant strand, and results in a high yield of recombinants bearing the inserted sequences. These insertional mutagenesis reactions can be conducted on relatively large quantities of DNA (e.g. 20 ug), enough to readily generate on the order of $10^{11}$ individual recombinants or more by electroporation.

Figure 2:
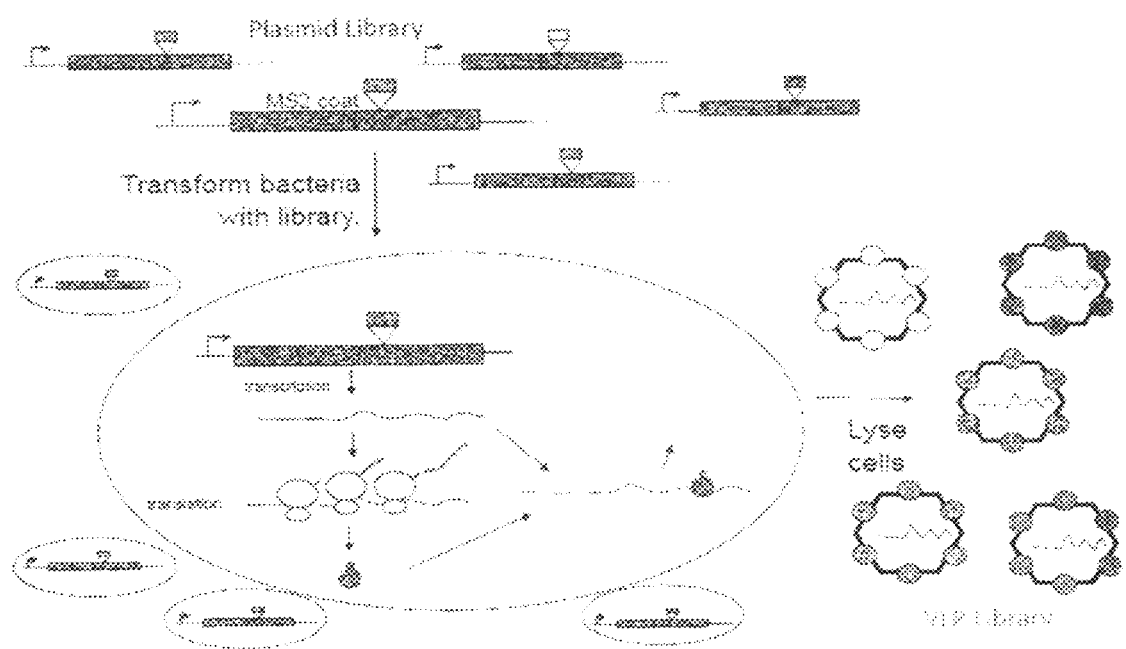
FIG. 2 shows the basics of display of random sequence peptide libraries on VLPs. A library of random sequence peptide insertions is created by recombinant DNA methods, the resulting plasmid population is introduced into E. coli by transformation, and a library of VLPs is produced. Each individual VLP in the population displays a different peptide on its surface and contains within it (in the form of mRNA) the genetic information for its synthesis.

To facilitate the production of single-stranded DNA, an M13 origin of replication was introduced into the plasmid and called it pDSP61 and pDSP62 (FIG. 2), depending on orientation of the M13 origin. Also constructed was a helper phage called M13CM1. It is a derivative of M13KO7 that replaces kanamycin resistance with chloramphenicol, making it possible to select for the simultaneous presence of the M13cm1 helper and pDSP6, which confers kanamycin resistance. Superinfection by an M13 helper phage of a dut−, ung− strain (e.g. CJ236) containing the plasmid results in facile production of dUTP-substituted single-stranded DNA.

D. A Synthetic "Codon-Juggled" Coat Gene.

The desire to use primer extension mutagenesis for library construction introduced a new complication and necessitated the introduction into pDSP6 of a so-called "codon-juggled" coat sequence. The peptide display method of the present invention relies on the ability to specifically introduce foreign peptides into only one of the two AB-loops of the single-chain dimer. In the scheme described above, the mutagenic primer would normally anneal to sequences in both halves of the single-chain dimer resulting in double insertions. But simultaneous insertions in both AB-loops result in a high frequency of protein folding failures. For this reason, the synthesis of a codon-juggled version of coat protein was accomplished. This codon-juggled version introduces the maximum possible number of silent nucleotide substitutions into the upstream half of the single-chain dimer, and thus produces a polypeptide having the wild-type coat protein amino acid sequence. However, the presence of numerous mutations makes the juggled sequence incapable of efficiently annealing to the mutagenic oligonucleotide. In this way insertions are targeted to the downstream half of the single-chain dimer.

Variants of pDSP1 and of pDSP62, referred to respectively as pDSP1(am) and pDSP62(am) retain all of the features of pDSP1 and PDSP62, but are modified by site directed mutagenesis to convert the alanine codon (which specifies the first amino acid of the downstream copy of coat protein in the single-chain dimer) to UAG, a specific nonsense or stop codon known as the amber codon. Suppression of this stop codon allows for synthesis of both wild-type and single-chain dimer coat proteins from a single mRNA. This results in the ability to control the average peptide display valency as described in more detail below.

Readthrough of the nonsense codon normally requires the presence of a suppressor tRNA specific for particular stop codon being suppressed. Suppressor tRNAs active for all three stop codons have been described and are well known to molecular biologists. The work described here utilizes an amber codon and therefore requires the use of an amber-suppressor tRNA, which in this case was specifically designed to insert alanine. However, it should be understood that suppressor tRNAs specific for each of the other stop codons (UAA and UGA), and inserting a variety of amino acids could be similarly utilized.

To produce the suppressor tRNA in bacterial cells a plasmid called pNMsupA was produced (see FIG. 3). It is a deriviative of pACYC18 and contains an origin of replication derived from the p15A plasmid incompatibility group. It also provides resistance to chloramphenicol. This means that it can be stably maintained in bacterial cells already containing pDSP1(am) or pDSP62(am) which have ColE1 origins and confer resistance to kanamycin. Plasmid pNMsupA also contains the lac promoter and polylinker regions of pUC18 into which a synthetic suppressor tRNA gene was inserted. The transcription of the tRNA gene is under control of the lac promoter, meaning that synthesis of the suppressor tRNA is controlled by inducers of the lac operon (e.g. IPTG). The sequence of the synthetic tRNA gene is modeled on that described previously by Kleina et al. (4) and is shown below—SEQ ID NO:14. It is flanked by EcoRI and PstI sites that facilitated its cloning in pNMsupA.

GAATTCGGGGCTATAGCTCAGCTGGGAGAGCGCTTGCATCTAAAGCAAG

AGGTCAGCGGTTCGATCCCGCTTAGCTCCACCACTGCAG

Altering the level of suppressor tRNA is known also to alter the level of nonsense suppression. By thus altering the level of synthesis of single-chain dimer from pDSP1(am) or pDSP62(am) it was believed possible to control the average number of peptides displayed per VLP, thus allowing control of display valency over a wide range. Although pNMsupA uses the lac promoter, it should be clear that a variety of promoters could be used for control of suppressor tRNA synthesis, and that some (e.g. the promoter of the propionate operon (5)) are, in fact, better able to provide well-controlled, graded responses to different concentrations of their respective inducers.

III. Controlling Display Valency.

It is desirable to have a means of controlling the number of peptides displayed on the MS2 VLP. The multivalency of MS2 VLP display (90 copies of the epitope per particle) should make it difficult to discriminate VLPs displaying peptides with high intrinsic affinity from those that have low intrinsic affinity, but still bind tightly by virtue of their ability to engage in multiple weak interactions (i.e. avidity vs. affinity). This is a well-known complication of filamentous phage display, where selection of high affinity interactions normally requires use of a low display valency. Finding appropriate molecular mimics is greatly increased when selecting the highest affinity peptides. Below is a description of a method for reducing display valency so as to improve the selection stringency.

Controlling Valency.

It is assumed that selection of peptides having the highest affinity for a given monoclonal antibody will provide the best molecular mimics of the native antigen, and that these are the most likely to induce a relevant antibody response. Ideally, the approach is to conduct the first round of selection using multivalent display, thus obtaining a relatively complex population including all peptides having some minimal affinity for the target. It would then be desirable to reduce the display valency in subsequent rounds so as to increase the stringency of affinity selection.

Figure 4:
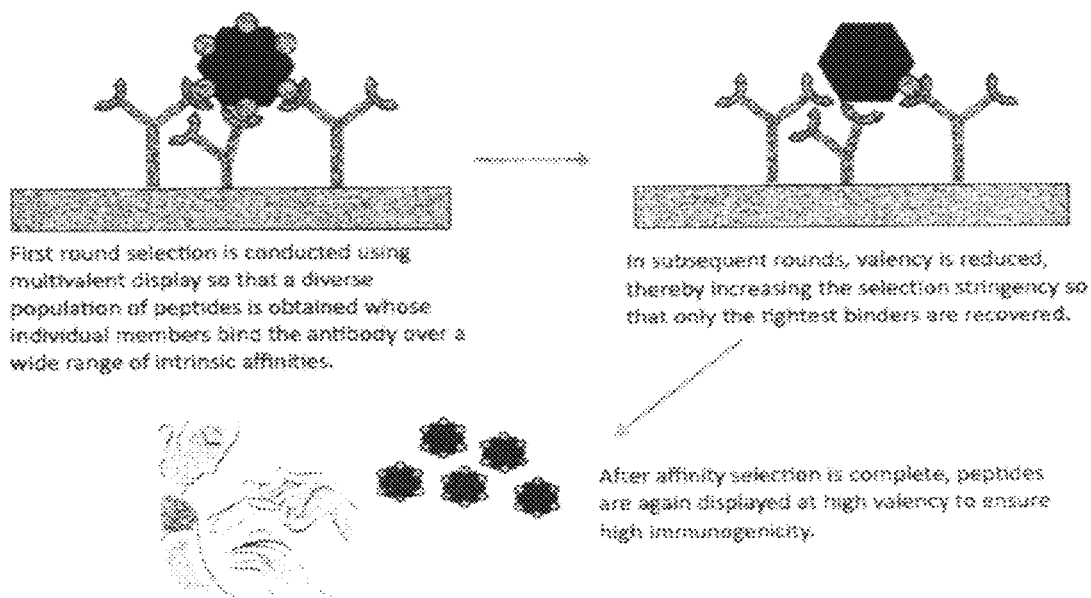
FIG. 4 shows the importance of peptide dislay valency. Multivalent display can make it difficult to distinguish intrinsically tight binders from weak binders interacting simultaneously with multiple receptors. Typically a first round of affinity selection is conducted at high valency, but in subsequent rounds valency is reduced to a low level, thus increasing the selection stringency and ensuring the isolation of peptides with the highest affinity for the selecting antibody.

In this approach, a system that allows the production of large amounts of wild-type and low quantities of AB-loop recombinant proteins from a single RNA is provided. A variant of pDSP1 (pDSP1(am)) was constructed which contains an amber stop codon in place of the alanine codon normally encoding the first amino acid of the downstream copy of coat protein in the single-chain dimer (see FIG. 3). pDSP1(am) therefore normally produces only wild-type coat protein, which, of course, assembles normally into a VLP. In addition, the inventors synthesized and cloned an alanine-inserting suppressor tRNA gene. Expressed under control of the lac promoter on a chloramphenicol resistant plasmid from a different incompatibility group, the suppressor tRNA is produced in amounts that cause a small percentage of ribosomes translating the coat sequence to read through the amber (stop) codon and produce the single-chain dimer. The resulting protein (with its guest peptide) co-assembles with wild-type protein expressed from the same mRNA to form mosaic capsids. Purified VLPs were produced from this vector and it was estimated that they would display about three peptides per VLP, on average. SDS gel electrophoresis (see FIG. 4) shows the content of the "readthrough" product in purified VLPs. These were tested to confirm the increase in stringency of affinity selection as predicted. Agarose gel electrophoresis and northern blots verify that the particles encapsidate the relevant RNA. If needed, the valency can be further reduced by decreasing the expression level of the suppressor tRNA. In fact, it is possible to be able to control the expression of the read-through product (and the display valency) over a wide range by adjusting the level of suppressor tRNA synthesis. This is accomplished by expressing the tRNA from a promoter (e.g. proB) whose activity can be precisely modulated as a function of inducer concentration.

Antigen Fragment Libraries

An alternative strategy takes advantage of the existence of a cloned antigen gene or pathogen genome to create random antigen fragment libraries. Several methods exist for the creation of such libraries. One involves random fragmentation of the antigen gene, for example by treatment with DNaseI to produce fragments of an appropriate average size (e.g. ~30 bp). These are blunt-end ligated to an appropriate site in the gene encoding the coat polypeptide (e.g. in the AB-loop of a single-chain coat protein dimer). The resulting library is then subjected to affinity selection to recover VLPs displaying peptides recognized by an antibody. In a particular embodiment, a restriction site may be inserted into the AB-loop or N-terminus of the coat polypeptide.

Synthesis

RNA phage VLPs are normally produced from plasmids in living *E. coli* cells, which are lysed and the VLPs extracted. In the experiments so far conducted by the inventors and described elsewhere in this application, random sequence peptide libraries on MS2 and PP7 VLPs have been produced exactly in this manner. However, in a particular alternative embodiment, the populations of the present invention may be synthesized in a coupled in vitro transcription/translation system using procedures known in the art (see, for example, U.S. Pat. No. 7,008,651; Kramer et al., 1999, Cell-free Coupled Transcription-translation Systems From *E. coli*, In Protein Expression. A Practical Approach, Higgins and Hames (eds.), Oxford University Press). In a particular embodiment, bacteriophage T7 (or a related) RNA polymerase is used to direct the high-level transcription of genes cloned under control of a T7 promoter in systems optimized to efficiently translate the large amounts of RNA thus produced (for examples, see Kim et al., 1996, Eur J Biochem 239: 88 1-886; Jewett et al., 2004, Biotech and Bioeng 86: 19-26).

When VLPs are produced in vivo, the *E coli* cell itself provides the compartmentalization that ensures that multiple copies of a given coat protein-peptide recombinant assemble specifically with its mRNA. Unless a similar form of compartmentalization is provided, it is possible that during synthesis in vitro from a mixture (i.e. library) of templates, particularly in the population of the present invention, different individual coat polypeptides, distinguished by their fusion to different peptides, could presumably package each other's mRNAs, thus destroying the genotype/phenotype linkage needed for effective phage display. Moreover, because each VLP is assembled from multiple subunits, formation of hybrid VLPs may occur. Thus, in one preferred embodiment, when preparing the populations or libraries of the present invention, one or more cycles of the transcription/translation reactions are performed in water/oil emulsions (Tawfik et al., 1998, *Nat Biotechnol* 16: 652-6). In this now well-established method, individual templates are segregated into the aqueous compartments of a water/oil emulsion. Under appropriate conditions huge numbers of aqueous microdroplets can be formed, each containing on average a single DNA template molecule and the machinery of transcription/translation. Because they are surrounded by oil, these compartments do not communicate with one another. The coat polypeptides synthesized in such droplets should associate specifically with the same mRNAs which encode them, and ought to assemble into VLPs displaying only one peptide. After synthesis, the emulsion can be broken and the VLPs recovered and subjected to selection. In one particular embodiment, all of the transcription/translation reactions are performed in the water/oil emulsion. In one particular embodiment, only droplets containing only one template per droplet (VLPs displaying only one peptide) are isolated. In another embodiment, droplets containing mixed VLPs are isolated (plurality of templates per droplet) in one or more cycles of transcription/translation reactions and subsequently VLPs displaying only one peptide (one template per droplet) are isolated.

Uses of VLPs and VLP Populations

There are a number of possible uses for the VLPs and VLP populations of the present invention. As will be described in further detail below, the VLPs may be used as immunogenic compositions, particularly vaccines, as drug delivery devices, as biomedical imaging agents or as self-assembling nanodevices. The VLP populations of the present invention may be used to select suitable vaccine candidates.

Selection of Vaccine Candidates

The VLP populations or libraries of the present invention may be used to select vaccine candidates. The libraries may be random or antigenic libraries. Libraries of random or alternatively antigen-derived peptide sequences are displayed on the surface of VLPs, and specific target epitopes, or perhaps mimotopes are then isolated by affinity-selection using antibodies. Since the VLPs encapsidate their own mRNAs, sequences encoding them (and their guest peptides) can be recovered by reverse transcription and PCR. Individual affinity-selected VLPs are subsequently cloned, over-expressed and purified.

Techniques for affinity selection in phage display are well developed and are directly applicable to the VLP display system of the present invention. Briefly, an antibody (or antiserum) is allowed to form complexes with the peptides on VLPs in a random sequence or antigen fragment display library. Typically the antibodies will have been labeled with biotin so that the complexes can be captured by binding to a streptavidin-coated surface, magnetic beads, or other suitable immobilizing medium. After washing, bound VLPs are eluted, and RNAs are extracted from the affinity-selected population and subjected to reverse transcription and PCR to recover the coat-encoding sequences, which are then recloned and subjected to further rounds of expression and affinity selection until the best-binding variants are obtained. A number of schemes for retrieval of RNA from VLPs are readily imagined. One attractive possibility is to simply capture biotin-mAb-VLP complexes in streptavidin coated PCR tubes, then thermally denature the VLPs and subject their RNA contents directly to RT-PCR. Many obvious alternatives exist and adjustments may be required depending on considerations such as the binding capacities of the various immobilizing media. Once the selected sequences are recovered by RT-PCR it is a simple matter to clone and reintroduce them into *E coli*, taking care at each stage to preserve the requisite library diversity, which, of course, diminishes with each round of selection. When selection is complete, each clone can be over-expressed to produce a VLP vaccine candidate.

To establish the efficacy of affinity selection on the MS2 VLP platform selections were conducted by the methods described above using a monoclonal antibody target whose epitope is well-characterized. The M2 anti-Flag monoclonal antibody, and a library constructed in pDSP1 to contain ten NNS triplets inserted between the codons for amino acids 13 and 16 (i.e. the 13/16 insertion mode). This particular library contained about $10^8$ independent clones and displayed foreign peptides at high valency. Since then, more complex libraries have been constructed using pDSP62 (see above), but the pDSP1 library was deemed sufficiently complex to give a reasonable probability of encountering the Flag epitope. The first selection round was conducted against 250 ng of the antibody immobilized by adsorption to plastic wells, with an estimated ten-fold excess of VLPs over antibody molecules. After extensive washing, bound VLPs were eluted and then subjected to reverse transcription and PCR. The PCR products were digested with SalI and BamHI and cloned in pDSP62 for production of VLPs for use in round 2. In this, and in all subsequent rounds, cloning of the selectants yielded at least 5×10$^6$ independent clones. The second selection was conducted under the same conditions as round 1. Products of the second and third rounds were cloned in pDSP62(am) and the VLPs were produced in the presence of the amber suppressor (pNMsupA) described above, meaning that in rounds 3 and 4 the peptides were displayed at low valency. In the fourth round the amount of antibody was reduced to 50 ng, so that VLPs were present at about 50-fold excess compared to antibody. After the fourth round, products were cloned in pDSP62 for high valency display in anticipation of overproduction and purification of VLPs. Sequences of a few selectants from each round are shown in FIG. 22. Sequences obtained in early rounds show limited similarity to the known Flag epitope, DYKDDDDKL, but certain key elements are already evident, including especially the YK dipeptide. By round three all the sequences show the DYK element together with at least one downstream D. By round four only one sequence was obtained from the 7 clones subjected to sequence analysis. Its similarity to the sequence of the wild-type flag epitope is obvious. The Flag epitope was previously mapped using conventional filamentous phage display methods and the results were reported in the NEB Transcript, Summer 1996. (The NEB Transcript is a publication of New England Biolabs (available at their web site, www. Neb.com), a commercial supplier of phage display libraries and affinity selection kits. The sequence reported in FIG. 22 is, in fact, a better fit to the actual epitope than that obtained in the NEB experiments, showing that the MS2 VLP display system is at least as effective as filamentous phage display for epitope identification by affinity-selection.

Immunogenic Compositions

As noted above, the VLPs identified by the screening procedures of the present invention may be used to formulate immunogenic compositions, particularly vaccines. The vaccines should be in a form that is capable of being administered to an animal. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition or disorder. Upon introduction into a host, the vaccine is able to provoke an immune response including, but not limited to, the production of antibodies and/or cytokines and/or the activation of cytotoxic T cells, antigen. presenting cells, helper T cells, dendritic cells and/or other cellular responses.

Optionally, the vaccine of the present invention additionally includes an adjuvant which can be present in either a minor or major proportion relative to the compound of the present invention. The term "adjuvant" as used herein refers to non-specific stimulators of the immune response or substances that allow generation of a depot in the host which when combined with the vaccine of the present invention provide for an even more enhanced immune response. A variety of adjuvants can be used. Examples include complete and incomplete Freund's adjuvant, aluminum hydroxide and modified muramyl dipeptide.

Optionally, the vaccine of the present invention additionally includes an adjuvant which can be present in either a minor or major proportion relative to the compound of the present invention.

Targeted Drug Delivery

Affinity selection can be used to identify peptides that bind specific cellular receptors, thus producing particles able to bind and enter (e.g. by endocytosis) a targeted cell. The MS2 VLP is a hollow sphere with an internal diameter on the order of 20 nm. In a particular embodiment, the VLP comprises the drug, e.g., a protein toxin to be delivered and optionally a ligand that binds to cell-type specific receptors. The internal composition of such a particle may be controlled by specifically loading it, for example, with a protein toxin like ricin, or by coupling it to a synthetic translational operator mimic. By conferring the ability to bind cell type-specific receptors to the outer surface of such particles, it is possible to target delivery of the toxin (or other drug) to selected cell types. In a related aspect, the VLP comprising the coat polypeptide dimer may actually encapsidate a heterologous substance such as a bacterial toxin, adjuvant or immunostimulatory nucleic acid.

Biomedical Imaging Agents

In the same way that drugs can be targeted to specific cell types, so could contrast agents for magnetic resonance imaging be delivered to specific cells or tissues, potentially increasing enormously the diagnostic power of an MRI. In fact, MS2 particles have already been labeled with gadolinium to greatly increase MRI contrast (Anderson et al., 2006, Nano Letters 6(6), 1160-1164). Thus, in a particular embodiment, such particles could be targeted to specific sites by displaying appropriate receptor-specific peptides on their surfaces. In a related aspect, the VLP comprising the coat polypeptide dimer may actually encapsidate the imaging agent.

Self-Assembling Nano-Devices

The VLPs of the present invention may comprise peptides with affinity for either terminus of a filamentous phage particle that displays metal binding proteins. A VLP with affinity for either terminus of a filamentous phage particle would create the possibility of connecting these spheres (and whatever they contain) to the ends of filamentous phage nanowires. Alternatively, the VLPs may display metal-binding peptides (e.g. gold and zinc) so that arrays with unusual electrical and optical properties may be obtained. Alternatively, VLPs with improved ability to self-assemble into these arrays may be produced by displaying peptides with affinity for a particular surface, or that alter the self-association properties of the VLPs themselves.

Experimental Overview

Two plasmid vectors that facilitate the construction of random-sequence peptide libraries on virus-like particles (VLPs) of bacteriophage MS2 are described. The first, pDSP1, was constructed for convenient cloning of PCR-generated—or other double-stranded DNA—fragments into the AB-loop of the downstream copy of a coat protein single chain dimer. The second is called pDSP62 and was constructed specifically for introduction of peptide sequences at virtually any position in the single-chain dimer (usually the AB-loop) by the site-directed mutagenesis method of Kunkel et al. [16]. The general features of the plasmids are presented below.

Example 1 pDSP1

A Plasmid Expressing a Single-Chain Dimer with Convenient Cloning Sites for Insertion in the AB-Loop The plasmid pDSP1 (see FIGS. 5a and 7a) contains the T7 transcription signals of pET3d and the kanamycin resistance and replication origin of pET9d. (Information regarding pET3d and pET9d may be found at the New England Biolabs vector database, available on the world wide web at lablife.org/ct?f=v&a=listvecinfo). It expresses the coding sequence of the MS2 single-chain coat protein dimer (6), modified to contain unique SalI and KpnI restriction sites. This facilitates simple cloning of foreign sequences into the AB-loop. To make these sites unique, it was necessary to destroy other SalI and KpnI sites in the vector and in the upstream coat sequence.

The MS2 coat sequence in the vicinity of the AB-loop insertion site for pDSP1 is shown below—SEQ ID NO:16 for the amino acid sequence and—SEQ ID NO:17 for the nucleotide sequence. Note the presence of SalI and KpnI sites.

```
... 6  7  8  9 10 11 12 13 14 15 16 17 18 19 20 21 22...

...GlnPheValLeuValAspAsnGlyGlyThrGlyAspValThrValAlaPro...

...CAGTTCGTTCTCGTCGACAATGGCGGTACCGGCGACGTGACTGTCGCCCA...
              SalI       KpnI
```

Shown below is an example of a random 7-mer library in pDSP1, with the random sequence inserted in the so-called 13/16 mode. SEQ ID NO:18 for the amino acid sequence and SEQ ID NO:19 for the nucleotide sequence.

```
... 6  7  8  9 10 11 12 13                16 17 18 19 20 21 22...

...GlnPheValLeuValAspAsnGly x  x  x  x  x  x  x GlyAspValThrValAlaPro...

...CAGTTCGTTCTCGTCGACAATGGCNNSNNSNNSNNSNNSNNSNNSGGCGACGTGACTGTCGCCCCA...
              SalI
```

Figure 5:
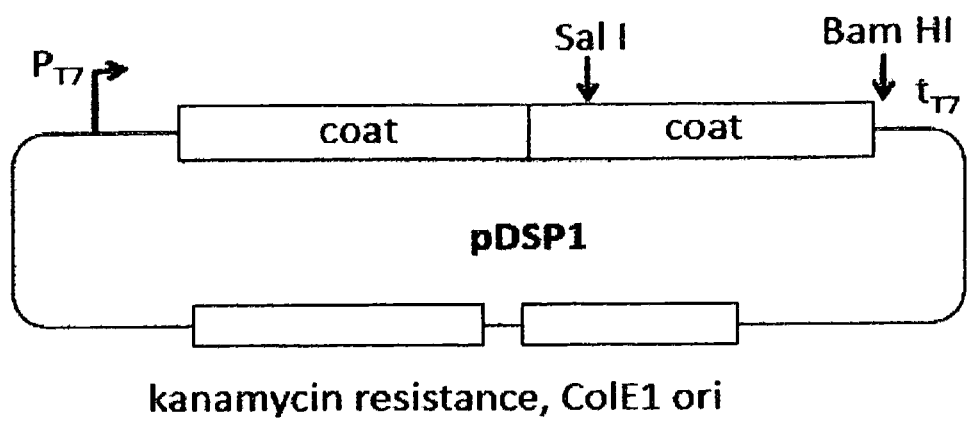
FIG. 5 shows plasmid pDSP1 with convenient cloning sites for insertion in the AB-loop. pDSP1 expresses the coding sequence of the single-chain dimer, modified to contain for example, unique SalI and KpnI restriction sites. This dimer facilitates simple cloning of foreign sequences into the AB-loop. To make these sites unique, it was necessary to destroy a number of SalI and KpnI sites in the vector and in the upstream coat sequence.

The presence of unique restriction sites in or near the sequences encoding the AB-loop makes is possible to simply insert foreign sequences when they are flanked with sites whose cleavage generates compatible "sticky ends". However, it is sometimes more convenient to attach the foreign sequence using a combination of PCR and recombinant DNA methods as shown in FIG. 5b. For example the 5'-PCR primer shown below could be used with a 3' primer, which anneals to plasmid vector sequences downstream of a Bam HI site, to generate a fragment of the coat protein coding sequence with the random sequence inserted between amino acids 13 and 16. N=A, C, G, or T and S=G or C. After digestion with SalI and BamHI, the fragment would be inserted between SalI and BamHI of pDSP1. Shown below is an example of a 5'-primer that could be used to generate such a library—SEQ ID NO:15:

```
5'-CGCGTCGACAATGGC(NNS)₇GGCGACGTGACTGTCGCCCCA-3'
```

With pDSP1, random-sequence peptide libraries are usually constructed by cloning into the AB-loop a PCR fragment generated using a monomeric coat protein sequence as template (e.g. pMCT). A synthetic oligonucleotide 5'-primer is designed to attach a SalI (or KpnI) site and a sequence of random codons (e.g. 6-10 copies of NNY) to a site just upstream of the AB-loop. A 3'-primer anneals to sequences in the plasmid vector just downstream of BamHI. The resulting PCR product is digested with SalI (or KpnI) and BamHI and cloned at the corresponding sites of pDSP1. This results in insertion of peptides into the AB-loop, the exact site of insertion depending on the specific design of the 5'-primer. For most insertions use of the SalI site is preferred as it affords more flexibility that KpnI in selection of the insertion site. With these methods it is relatively straightforward to produce peptide VLP libraries with up to $10^8$-$10^9$ individual members.

To introduce a means for control of peptide display valency a derivative of pDSP1 (called pDSP1(am) was constructed by introduction of a nonsense codon at the junction between the halves of the single-chain dimer. When expressed in the presence of a nonsense suppressor tRNA, such as that produced by pNMsupA, a small amount of the single-chain dimer (with its foreign peptide) is produced. Most of the coat protein produced from pDSP1(am), however, is synthesized in the form of the wild-type, unit length protein. The two forms of coat protein co-assemble into a hybrid particle that displays on average only about 3 peptides. The average level of display valency can be adjusted upward or downward by altering the expression level of the suppressor tRNA, or by employing suppressors exhibiting greater or lesser suppression efficiencies.

Example 2 pDSP62

A Plasmid Suitable for Library Construction Using Efficient Site-Directed Mutagenesis Methods Introduction of an M13 Origin of Replication.

Methods for library production like that described above for pDSP1, are difficult to scale up, because it is inconvenient to purify DNA restriction fragments in the necessary quantities. Moreover, during ligation reactions some of the DNA is inevitably diverted into useless side-products, reducing the yield of the desired plasmid. The construction of complex libraries would be facilitated by methods that efficiently produce larger yields of the correct recombinant DNA than are found in a typical ligation reaction. Specifically, a variation of an old method for site-directed mutagenesis is preferred to be used, which was already by others to produce peptide libraries on filamentous phage in the 10" complexity range (2, 6). The method is applied to single-stranded circular DNAs produced from a particular kind of plasmid (also know as a phagemid) that contains an M13 origin of replication. Infection with an M13 helper phage (e.g. M13K07) of a dut⁻, ung⁻ strain (e.g. BW313) containing the plasmid results in facile production of dUTP-substituted single-stranded DNA. In the actual mutagenesis reaction, a mismatched oligonucleotide primer is annealed to the single-stranded DNA template and is elongated using a DNA polymerase (e.g. that of T7 phage). The DNA is ligated to produce closed circular DNA, and introduced by transformation into and ung⁺ strain, where the mutant strand is preferentially replicated. Previous experience in the production of peptide-VLP libraries indicates that typically about 90% of the transformants contain the desired peptide insertions. The primer extension mutagenesis reaction can be conducted on relatively large quantities of DNA (e.g. 20 ug), enough to readily generate on the order of $10^{11}$ individual recombinants by electroporation.

To facilitate the production of single-stranded DNA, an M13 origin of replication was introduced into pDSP1. To do this, the M13 origin found in pUC119 was amplified by PCR and cloned at a unique AlwNI site in pDSP1. This plasmid, called pDSP1-IG, is the progenitor to pDSP62. Because it is only an intermediate in the construction of pDSP62 I, its sequence is not shown.

Targeting Insertions to Only One Half of the Single-Chain Dimer Through the Use of a Synthetic "Codon-Juggled" Coat Gene.

The desire to use primer-extension mutagenesis for efficient peptide library construction introduced a new complication. The present display method relies on the ability to specifically introduce foreign peptides into only one of the two AB-loops of the single-chain dimer. Using the single-chain dimer sequence present in pDSP1, the mutagenic primer would anneal to sequences in both halves, resulting in double insertions, but it is already known that insertions in both AB-loops result in a high frequency of protein folding failures. Moreover, even if the insertions were tolerated, an site-directed mutagenesis that failed to target only one half of the single-chain dimer would result in the display of two different peptides on each VLPs.

Figure 6:
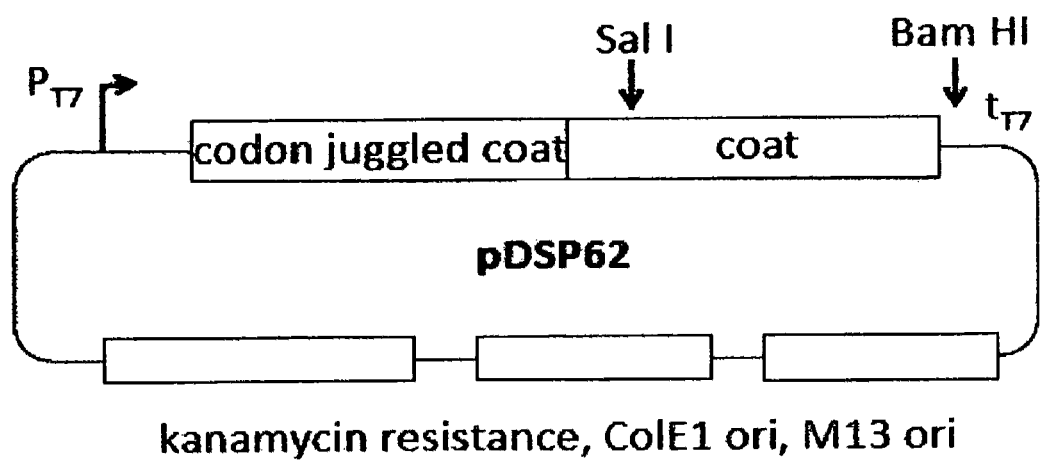
FIG. 6 shows the plasmid pDSP62. To facilitate the production of single-stranded DNA, an M13 origin of replication was introduced into the plasmid and identified as pDSP61 and pDSP62, depending on the orientation of the M13 origin. This plasmid also contains a so-called "codon juggled" coat sequence in the upstream half of the single-chain dimer. The codon-juggled half encodes the same amino acid sequence as the downstream half, but differs from it by containing the maximum possible number of silent substitutions, making the two halves distinguishable for purposes of annealing of oligonucleotides.

For these reasons, a "codon-juggled" version of coat protein was synthesized and exchanged for the normal upstream half of the single-chain dimer. The codon-juggled sequence contains the maximum possible number of silent nucleotide substitutions, and thus produces a polypeptide having the wild-type coat protein amino acid sequence. However, the presence of numerous mutations makes the juggled sequence incapable of efficiently annealing to the mutagenic oligonucleotide, and therefore the mutagenic primer is specifically directed to the downstream AB-loop sequence. Plasmid pDSP62 is shown in FIG. 6 and its sequence is provided in FIG. 7b.

A Chloramphenicol-Resistant M13 Helper Phage for Single-Strand pDSP62 Production.

Plasmid pDSP62 confers resistance to kanamycin. The helper phages (e.g. M13KO7) usually used for production of single stranded phagemid DNA also confer kanamycin resistance, and are therefore unsuitable for use with the plasmids described here. For this reason, M13CM1 was constructed, a chloramphenicol resistant derivative of M13KO7. The chloramphenicol resistance gene of pACYC184 (7) was amplified by PCR using primers that attached recognition sequences for XhoI and SacI, and the fragment was inserted into M13KO7 in place of its kanamycin resistance gene, taking advantage of XhoI and SacI sites that roughly flank the kanamycin resistance determinant. In the presence of kanamycin (selects for pDSP62 maintenance) and chloramphenicol (selects for helper phage), cells produce large quantities of single-stranded plasmid DNA after infection with M13 CM1. Using these single-stranded templates and the method of Kunkel et al. (2), random sequence peptide libraries have been readily produced that contain more than $10^{10}$ individual members for $[NNS]_6$, $[NNS]_7$, $[NNS]_8$ and $[NNS]_{10}$. Significantly higher complexities are possible with scale-up.

To introduce a means for control of peptide display valency a derivative of pDSP62 (called pDSP62(am)) was constructed by introduction of a nonsense codon at the junction between the halves of the single-chain dimer. When expressed in the presence of a nonsense suppressor tRNA, such as that produced by pNMsupA, a small amount of the single-chain dimer (with its foreign peptide) is produced. Most of the coat protein produced from pDSP1(am), however, is synthesized in the form of the wild-type, unit length protein. The two forms of coat protein co-assemble into a hybrid particle that displays on average only about 3 peptides. The average level of display valency can be adjusted upward or downward by altering the expression level of the suppressor tRNA, or by employing suppressors exhibiting greater or lesser suppression efficiencies.

As described above, virus-like particles of bacteriophage MS2 were used for peptide display, and it was established that MS2 coat protein single-chain dimers are highly tolerant of peptide insertions and that they produce correctly assembled VLPs that specifically encapsidate the mRNA encoding their synthesis [2]). But MS2 is only one member of a large family of viruses whose individual members share similar molecular biology. The plasmids and methods described above represent refinements to the MS2 VLP display system described previously, in which the inventors had demonstrated the insertion tolerance of the MS2 coat protein single-chain dimer and the ability of the MS2 VLP to encapsidate the mRNA that directs its synthesis [2]. The examples that follow document similar results recently obtained for PP7 VLPs [1], showing specifically that the folding and assembly of the PP7 single-chain coat protein dimer also exhibits high tolerance to foreign peptide insertion and that the VLPs thus obtained contain, in the form of mRNA, the genetic information for their synthesis.

Here, then, is described the engineering of VLPs of PP7, a bacteriophage phage of *Pseudomonas aeruginosa*, for purposes of peptide display.

PP7 VLPs offer several potential advantages and improvements over the MS2 VLP. First, the particles are dramatically more stable thermodynamically, because of the presence of stabilizing inter-subunit disulfide bonds (8). For many practical applications, including vaccines, increased stability is a desirable trait. Second, PP7 VLPs are not cross-reactive immunologically with those of MS2 (9). This could be important in vaccine or targeted drug delivery applications where serial administration of VLPs may be necessary. Third, it is anticipated that the correct folding and assembly of the PP7 VLP might be more resistant to the destabilizing effects of peptide insertion, or that it might at least show tolerance of some peptides not tolerated in MS2 VLPs.

Example 3

Design of a PP7 Peptide Display Vector

Two general kinds of plasmid were constructed for the synthesis of PP7 coat protein in *E coli* (see FIGS. 9 and 13).

The first expresses coat protein from the lac promoter and is used (in combination with pRZP7—see below) to assay for coat protein's tolerance of peptide insertions using translational repressor and VLP assembly assays. The second plasmid type expresses the protein from the T7 promoter and transcription terminator. These plasmids produce large amounts of coat protein that assembles correctly into a VLP. They also produce coat-specific mRNA with discrete 5'- and 3'-termini for encapsidation into VLPs.

Design of the Peptide Insertion Site.

The three-dimensional structure of the PP7 capsid shows that it is comprised of a coat protein whose tertiary structure closely mimics that of MS2, even though the amino acid sequences of the two proteins show only about 12% sequence identity (10)[17]. The PP7 protein possesses an AB-loop into which peptides may be inserted following a scheme similar to the one previously described for MS2 [2]. As in the MS2 case, this began by mutating the PP7 coat sequence to contain a site for the restriction endonuclease KpnI, thus facilitating insertion of foreign sequences in the plasmid called pP7K (FIG. 9a). This modification resulted in the amino acid substitution (E11T) shown in FIG. 10. This substitution was well tolerated, since the mutant coat protein represses translation and assembles correctly into a VLP. Again following the MS2 example, it was assumed that the folding of a single chain dimer version of PP7 coat protein would be more resistant to AB-loop insertions than the conventional dimer. Its construction was described previously (8), but here it is described for the first time, for use for peptide display. The single-chain dimer was modified to contain a KpnI site only in the downstream copy of the coding sequence, producing p2P7K32 (FIG. 9b). In this design, peptides were inserted at amino acid 11, but it should be noted that other specific insertion sites are could be used, possibly anywhere within the AB-loop. In fact, below tests are described of two alternative insertion modes (FIGS. 10 and 11). The first is called the 11/11 mode because the 11$^{th}$ amino acid appears twice—as thr on the N-terminal side of the inserted peptide, and as the wild-type glu11 on the C-terminal side. In the so-called 11/12 mode, the insertion is flanked by thr11 on one side and ala12 on the other.

To test the general tolerance of PP7 coat protein to AB-loop insertions, libraries of random sequence peptides inserted in the AB-loop of PP7 coat protein were created using the scheme shown in FIG. 11. The random sequences consisted of 6, 8 or 10 copies of the sequence NNY (where N is any nucleotide and Y is pyrimidine). Such libraries contain 15 of the 20 possible amino acids, and are therefore capable of substantial diversity. However, by avoiding the possibility of stop codons subsequent analysis is greatly facilitated.

Example 4

Methods to Test Individual Members of Random-Sequence Peptide Libraries for Retention of Coat Protein Function Like MS2 coat protein, PP7 coat is a translational repressor. The construction of pRZP7, a plasmid that fuses the PP7 translational operator to the *E. coli* lacZ gene, was previously described, placing β-galactosidase synthesis under control of the coat protein's translational repressor activity (11). Because it confers resistance to a different antibiotic (chloramphenicol), and because it comes from a different incompatibility group (i.e. it uses the p15A replication origin), it can easily be maintained in the same *E. coli* strain as either pP7K or p2P7K32, both of which confer resistance to ampicillin and use a colE1 origin. Both of these plasmids are derived from pUC119 and express coat protein at relatively low levels from the lac promoter. The expression of PP7 coat protein from pP7K or p2P7K32 represses translation of β-galactosidase expressed from pRZP7. This makes it easy to determine whether a given peptide insertion has interfered with the ability of coat protein to correctly fold, since defective coat proteins give blue colonies on plates containing the β-galactosidase chromogenic substrate known as "xgal", whereas a properly functioning coat protein yields white colonies.

A more rigorous test of maintenance of function is to directly assay for the presence of VLPs in lysates of cells expressing a peptide-coat protein recombinant. This is accomplished by electrophoresis on agarose gel of cells lysed by sonication. Ethidium bromide staining detects the RNA-containing VLP, whose presence is then confirmed by western blot analysis using anti-PP7 serum.

The idea then is to test the peptide insertion tolerance of PP7 coat protein and assembly by creating random-sequence peptide libraries and determining the fraction of clones that retain translational repressor function (i.e. produce white colonies) and produce a VLP. Note that a similar test of the peptide insertion tolerance of the MS2 coat protein single-chain dimer was previously reported by these inventors [2].

Example 5

PP7 Coat Protein Folding and Assembly Tolerate Most Random 6-Mer, 8-Mer, and 10-Mer Peptide Insertions The $(NNY)_8$ libraries were constructed in pP7K and p2P7K32 and introduced into *E. coli* strain CSH41F-/pRZP7 by transformation. Transformants were plated on solid medium containing xgal. The vast majority were bona fide recombinants, since control ligations without insert fragment gave 1000× fewer colonies. Only a small number of the pP7K recombinants were tested, but it was found that all were defective for protein folding and failed to make VLPs. This confirms the expectation from prior experiments with MS2 [21] that the conventional dimer is normally destabilized by peptide insertions in the AB-loop. In the single-chain dimer of p2P7K32, however, nearly 100% of colonies were white. Twenty-four white colonies from each of the libraries were transferred to duplicate 1 ml cultures. From one culture set, crude cell lysates were prepared for agarose gel analysis of VLPs. From the other set, plasmids were isolated and subjected to restriction enzyme digestion and gel electrophoresis, verifying that all contained an insertion of the expected length. Plasmids from the few blue colonies were also isolated.

All turned out to contain plasmids resulting from aberrant ligation events, and generally did not contain an intact coat sequence. Virtually 100% of peptide insertions were compatible with the translational repressor function of coat protein. That is, they produce sufficient properly folded coat protein to repress translation like the wild-type protein. This result was obtained with all the NNY libraries—6-mer, 8-mer and 10-mer—independent of whether they were cloned in the 11/11 or 11/12 modes.

To test directly for the presence of VLPs, crude cell lysates were prepared from each of the duplicate cultures and subjected to agarose gel electrophoresis. Gels were stained with ethidium bromide and a duplicate was blotted nitrocellulose and probed with mouse anti-PP7 serum and a horseradish peroxidase labeled second antibody. A clone is regarded as positive for VLP synthesis when it contains a band in both the stained gel and western blot. The results are shown in FIG. 13, demonstrating that nearly all of the 6-mer clones produce a VLP at some level, although a few show reduced yields. This was true for both the 11/11 and 11/12 insertions modes. The vast majority of 8-mer clones also produce a readily identifiable VLP. However, the efficiency seems to drop somewhat as insertion length increases to 10-mers, but still a clear majority of the clones produce a VLP. Note that the mobilities of the individual particles are variable, consistent with the expectation that some peptides alter the surface charge of the VLP by incorporating charged amino acids.

Example 6

The PP7 VLP Encapsidates Coat-Specific mRNA

For high-level expression and RNA encapsidation tests, the PP7 coat sequences of pP7K and p2P7K32 were cloned into a plasmid containing the T7 promoter and transcription terminator, producing the plasmids called pETP7K and pET2P7K32. The plasmids, in *E. coli* strain BL21(DE3), synthesized large amounts of coat protein. The resulting VLPs were purified by chromatography on Sepharose CL4B as described previously (11, 12). RNA was purified from VLPs by phenol/chloroform extraction and subjected to electrophoresis in duplicate agarose gels containing formaldehyde. One gel was stained with ethidium bromide and the other was blotted to nitrocellulose (Northern blot) where PP7 sequences were detected using a labeled synthetic oligonucleotide specific for the coat sense-strand. RNAs produced by transcription in vitro of pETP7K and pET2P7K32 with T7 RNA polymerase were utilized as standards. Each VLP contains a predominant species whose mobility is identical to that of the in vitro transcription product, and which hybridizes specifically with the PP7 coat-specific probe. It was determined that PP7 VLPs encapsidate their mRNAs, establishing the genotype-phenotype linkage necessary for affinity selection. Note that similar tests of MS2 coat protein's ability to encapsidate its mRNA were reported previously by these inventors.

Example 7

Peptides Displayed on PP7 VLPs are Displayed to the Immune System and are Immunogenic PP7 VLPs displaying the specific peptide sequences shown in FIGS. 10 and 15 were constructed. These included the so-called Flag peptide and sequences derived from the minor capsid protein L2 of human Papillomavirus type 16 (HPV16), the V3 loop of HIV-1 gp120, and *Bacillus anthracis* protective antigen. To demonstrate that these inserted peptides were indeed displayed on the surface of VLPs, the ability of a monoclonal antibody against HPV16 L2 (called RG-1) to bind to PP7 L2-VLPs was assessed by ELISA. As shown in FIG. 16, RG-1 bound to L2-VLPs, but not to PP7 VLPs that displayed the V3 peptide. To demonstrate the immunogenicity of the VLPs, mice were immunized with V3-VLPs by intramuscular injection as described previously [2]. As shown in FIG. 17, sera from the mice were tested by ELISA and shown to have high titer IgG antibodies that specifically react with a synthetic version of the V3 peptide. Note that similar tests of the immunogenicity of peptides displayed on MS2 VLPs were previously reported by these inventors.

Example 8

The plasmids pET2P7K32 and pDSP7 are the PP7 analogs of the MS2 coat protein producers pDSP1 and pDSP62 described above. For control of peptide display valency on PP7 VLPs the pET2P7K32(am) and pDSP7(am) were also constructed. They are analogs of pDSP1(am) and pDSP7 (am), respectively:

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. Any inconsistency between the material incorporated by reference and the material set for in the specification as originally filed shall be resolved in favor of the specification as originally filed. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

LITERATURE CITED

First Set of References

1. Peabody, D S, Jordan, S K, Caldeira, J C, Manifold-Wheeler, B, Medford, A and Chackerian, B (2007) Immunogenic display of diverse peptides on virus-like particles of RNA phage MS2. *J. Mol. Biol.* 380: 252-263.
2. Kunkel T A, Bebenek, McClary J. (1991) Efficient Site-Directed Mutagenesis Using Uracil-Containing DNA. Methods Enzymol. 204:125-139.
3. Sidhu S S, Lowman H B, Cunningham B C, Wells J A. (2000) Phage display for selection of novel binding peptides. Methods Enzymol. 328:333-363.
4. Kleina L G, Masson J-M, Normanly J, Abelson J, and Miller J H. (1990) Construction of *Escherichia coli* Amber Suppressor tRNA Genes. J. Mol. Biol. 213: 705-717.
5. Lee S K and Deasling J D. (2005) A propionate-inducible expression system for enteric bacteria. Appl. Env. Microbiol. 71:6856-6862.
6. Peabody, D. S., and Lim, F. (1996) *Nucleic Acids Res* 24, 2352-2359.
7. Chang, A. C., and Cohen, S. N. (1978) *J Bacteriol* 134, 1141-1156.
8. Caldeira, J. C., and Peabody, D. S. (2007) *J Nanobiotechnology* 5, 10
9. Olsthoorn, R. C., Garde, G., Dayhuff, T., Atkins, J. F., and Van Duin, J. (1995) *Virology* 206, 611-625.
10. Tars K, F. K., Bundule M, Liljas L. (2000) *Virology* 272, 331-337
11. Lim, F., Downey, T. D., and Peabody, D. S. (2001) *Journal of Biological Chemistry* 276, 22507-22512.
12. Peabody, D. S. (1990) *J Biol Chem* 265, 5684-5689.

LITERATURE CITED

Second Set of References

1. Caldeira Jdo C, Medford A, Kines R C, Lino C A, Schiller J T, Chackerian B, Peabody D S: Immunogenic display of diverse peptides, including a broadly cross-type neutralizing human papillomavirus L2 epitope, on virus-like particles of the RNA bacteriophage PP7. *Vaccine*, 28(27): 4384-4393.
2. Peabody D S, Manifold-Wheeler B, Medford A, Jordan S K, do Canso Caldeira J. Chackerian B: Immunogenic display of diverse peptides on virus-like particles of RNA phage MS2. *J Mol Biol* 2008, 380(1):252-263.
3. Lowman H B, Bass S H, Simpson N, Wells J A: Selecting high-affinity binding proteins by monovalent phage display. *Biochemistry* 1991, 30(45):10832-10838.
4. Sidhu S S, Lowman H B, Cunningham B C, Wells J A: Phage display for selection of novel binding peptides. *Methods in Ezymology* 2000, 328:333-363.
5. Wells J A: Hormone mimicry. *Science* 1996, 273(5274): 449-450.
6. Peabody D S: Subunit fusion confers tolerance to peptide insertions in a virus coat protein. *Arch Biochem Biophys* 1997, 347(1):85-92.
7. Peabody D S, Chakerian A: Asymmetric contributions to RNA binding by the Thr(45) residues of the MS2 coat protein dimer. *J Biol Chem* 1999, 274(36):25403-25410.
8. Lim F, Peabody D S: RNA recognition site of PP7 coat protein. *Nucleic Acids Res* 2002, 30(19):4138-4144.
9. Lim F, Downey T P, Peabody D S: Translational repression and specific RNA binding by the coat protein of the *Pseudomonas* phage PP7. *J Biol Chem* 2001, 276(25): 22507-22513.
10. Kunkel T A, Bebenek K, Mcclary J: Efficient Site-Directed Mutagenesis Using Uracil-Containing DNA. *Methods in Enzymology* 1991, 204:125-139.
11. Tars K F K, Bundule M, Liljas L: The Three-Dimensional Structure of Bacteriophage PP7 from *Pseudomonas aeruginosa* at 3.7 A Resolution. *Virology* 2000, 272:331-337.
12. Kleina L G, Masson J M, Normanly J, Abelson J, Miller J H: Construction of *Escherichia coli* amber suppressor tRNA genes. II. Synthesis of additional tRNA genes and improvement of suppressor efficiency. *J Mol Biol* 1990, 213(4):705-717.
13 Normanly J, Kleina L G, Masson J M, Abelson L Miller J H: Construction of *Escherichia coli* amber suppressor tRNA genes. III. Determination of tRNA specificity. *J Mol Biol* 1990, 213(0:719-726.
14. Kunkel T A: Rapid and efficient site-specific mutagenesis without phenotypic selection. *Proc Natl Acad Sci USA* 1985, 82(2):488-492.
15. Maruyama I N, Maruyama H I, Brenner S: Lambda foo: a lambda phage vector for the expression of foreign proteins. *Proc Natl Acad Sci USA* 1994, 91(17):8273-8277.
16. Mikawa Y G, Maruyama I N, Brenner S: Surface display of proteins on bacteriophage lambda heads. *J Mol Biol* 1996, 262(1):21-30.
17. Dunn I S: Assembly of functional bacteriophage lambda virions incorporating C-terminal peptide or protein fusions with the major tail protein. *J Mol Biol* 1995, 248(3):497-506.

---

The invention claimed is:

1. A nucleic acid construct comprising:
    (a) a bacterial or bacteriophage promoter operably associated with a coding sequence of an RNA bacteriophage single chain coat polypeptide dimer, the RNA bacteriophage single chain coat polypeptide dimer comprising (i) a first upstream coat polypeptide coding sequence, (ii) a second downstream coat polypeptide coding sequence comprising a nucleic acid sequence insert encoding a heterologous peptide, and (iii) a translation stop codon between the upstream and downstream coat polypeptide encoding sequences;
    (b) a replication origin for replication in a prokaryote; and
    (c) an antibiotic resistance gene.

2. A nucleic acid construct according to claim 1 wherein the nucleic acid segment encoding the upstream or downstream coat polypeptide comprises multiple silent nucleotide substitutions.

3. A nucleic acid construct according to claim 1 wherein the RNA bacteriophage single chain coat polypeptide dimer encodes a MS2 or PP7 single chain coat polypeptide dimer.

4. A nucleic acid construct according to claim 1 wherein the translational stop codon is TAG or UAG.

5. A nucleic acid construct according to claim 1 wherein said bacterial or bacteriophage promoter is a T7 or lac promoter.

6. A nucleic acid construct according to claim 1 wherein said antibiotic resistance gene is a kanamycin, ampicillin or chloramphenicol resistance gene.

7. A nucleic acid construct according to claim 1 further comprising a nucleic acid encoding a tRNA able to at least partially suppress translation termination at said translation stop codon.

8. A nucleic acid construct according to claim 1 wherein said heterologous peptide is inserted in the AB loop at the carboxy-terminus or at the amino-terminus of the downstream RNA bacteriophage coat polypeptide.

9. The nucleic acid construct according to claim 1 wherein said heterologous peptide is selected from the group consisting of a self-antigen, a receptor, a ligand which binds to a cell surface receptor, a peptide with affinity for either end of a filamentous phage particle specific peptide, an HIV peptide, a Flag peptide, an amino acid sequence derived from the minor capsid protein L2 of human Papillomavirus type 16 (HPV 16), the V3 loop of HIV-1 gp120, *Bacillus anthracis* protective antigen, a metal binding peptide or a peptide with affinity for the surface of MS2 or PP7.

10. A prokaryote transformed by the nucleic acid construct according to claim 1.

11. The prokaryote according to claim 10 wherein the prokaryote is *E. coli*.

12. A virus-like particle expressed by a prokaryote of claim 10.

13. A population of virus like particles comprising virus-like particles according to claim 12.

* * * * *